US010358660B2

(12) United States Patent
Ashby et al.

(10) Patent No.: US 10,358,660 B2
(45) Date of Patent: Jul. 23, 2019

(54) COMPOSITIONS AND METHODS FOR IDENTIFYING AND MODIFYING CARBONACEOUS COMPOSITIONS

(71) Applicant: TAXON BIOSCIENCES, INC., Tiburon, CA (US)

(72) Inventors: Matthew Ashby, Mill Valley, CA (US); Ladonna Wood, Mill Valley, CA (US); Ulrika Lidstrom, San Francisco, CA (US); Christine Clarke, Tiburon, CA (US); Alison Gould, Ann Arbor, MI (US); Dariusz Strapoc, Houston, TX (US); Adewale J. Lambo, Brookshire, TX (US); Bradley James Huizinga, Houston, TX (US)

(73) Assignee: TAXON BIOSCIENCES, INC., Tiburon, CA (US)

( * ) Notice: Subject to any disclaimer, the term of this patent is extended or adjusted under 35 U.S.C. 154(b) by 0 days.

(21) Appl. No.: 15/861,252

(22) Filed: Jan. 3, 2018

(65) Prior Publication Data
US 2018/0163234 A1    Jun. 14, 2018

Related U.S. Application Data

(60) Continuation of application No. 14/920,165, filed on Oct. 22, 2015, now abandoned, which is a division of application No. 13/504,120, filed as application No. PCT/US2011/040742 on Jun. 16, 2011, now Pat. No. 9,206,680.

(60) Provisional application No. 61/495,815, filed on Jun. 10, 2011, provisional application No. 61/355,488, filed on Jun. 16, 2010.

(51) Int. Cl.
*C12P 5/02*      (2006.01)
*C12N 1/20*      (2006.01)
*C12Q 1/04*      (2006.01)
*E21B 43/16*     (2006.01)
*E21B 43/295*    (2006.01)
*C09K 8/582*     (2006.01)

(52) U.S. Cl.
CPC .............. *C12P 5/023* (2013.01); *C09K 8/582* (2013.01); *C12N 1/20* (2013.01); *C12Q 1/04* (2013.01); *E21B 43/16* (2013.01); *E21B 43/295* (2013.01); *Y02E 50/343* (2013.01); *Y02P 20/128* (2015.11)

(58) Field of Classification Search
CPC .......................... C12P 5/023; C09K 8/582
USPC ........................................................ 506/7
See application file for complete search history.

(56) References Cited

U.S. PATENT DOCUMENTS

| | | | |
|---|---|---|---|
| 4,826,769 | A | 5/1989 | Menger |
| 5,055,397 | A | 10/1991 | Michaels et al. |
| 5,093,236 | A | 3/1992 | Gonzales-Prevatt et al. |
| 5,424,195 | A | 6/1995 | Volkwein |
| 5,670,345 | A | 9/1997 | Srivastava et al. |
| 5,695,937 | A | 12/1997 | Kinzler et al. |
| 5,845,032 | A | 12/1998 | Konda et al. |
| 5,866,330 | A | 2/1999 | Kinzler et al. |
| 5,981,190 | A | 11/1999 | Israel |
| 6,543,535 | B2 | 4/2003 | Converse et al. |
| 6,613,520 | B2 | 9/2003 | Ashby |
| 7,426,960 | B2 | 9/2008 | Pfeiffer et al. |
| 7,696,132 | B2 | 4/2010 | Pfeiffer et al. |
| 7,832,475 | B2 | 11/2010 | Jin et al. |
| 8,071,295 | B2 | 12/2011 | Ashby |
| 8,476,016 | B2 | 7/2013 | Ashby |
| 2001/0045279 | A1 | 11/2001 | Converse et al. |
| 2002/0065609 | A1 | 5/2002 | Ashby |
| 2004/0033557 | A1 | 2/2004 | Scott et al. |
| 2004/0110183 | A1 | 6/2004 | Ashby |
| 2006/0223159 | A1 | 10/2006 | Pfeiffer et al. |
| 2007/0161077 | A1 | 7/2007 | Pfeiffer et al. |
| 2007/0248531 | A1 | 10/2007 | Debryun et al. |
| 2007/0251146 | A1 | 11/2007 | Larter et al. |
| 2008/0277338 | A1 | 11/2008 | Whiteman |

(Continued)

FOREIGN PATENT DOCUMENTS

| | | |
|---|---|---|
| CN | 101705199 A | 5/2010 |
| WO | WO-2005115649 A1 | 12/2005 |

(Continued)

OTHER PUBLICATIONS

Alon U., et al., "Broad Patterns of Gene Expression Revealed by Clustering Analysis of Tumor and Normal Colon Tissues Probed by Oligonucleotide Arrays," Proceedings of the National Academy of Sciences, vol. 96(12), Jun. 1999, pp. 6745-6750.

(Continued)

*Primary Examiner* — Karla A Dines
(74) *Attorney, Agent, or Firm* — Bookoff McAndrews, PLLC

(57) ABSTRACT

This invention generally relates to natural gas and methylotrophic energy generation, bio-generated fuels and microbiology. In alternative embodiments, the invention provides nutrient amendments and microbial compositions, e.g., consortia, that are both specifically optimized to stimulate methanogenesis, or for "methylotrophic" or other conversions. In alternative embodiments, the invention provides methods to develop nutrient amendments and microbial compositions that are both specifically optimized to stimulate methanogenesis in a given reservoir. The invention also provides methods for the evaluation of potentially damaging biomass formation and scale precipitation resulting from the addition of nutrient amendments. In other embodiments, the invention provides methods for simulating biogas in subsurface conditions using a computational model.

26 Claims, 26 Drawing Sheets
Specification includes a Sequence Listing.

(56) References Cited

U.S. PATENT DOCUMENTS

| | | |
|---|---|---|
| 2008/0318303 A1 | 12/2008 | Lorah et al. |
| 2010/0047793 A1 | 2/2010 | Toledo et al. |
| 2010/0081184 A1 | 4/2010 | Downey et al. |
| 2010/0093049 A1 | 4/2010 | Datta et al. |
| 2011/0251983 A1 | 10/2011 | Ashby |
| 2011/0308790 A1 | 12/2011 | Strapoc et al. |
| 2013/0030712 A1 | 1/2013 | Ashby |
| 2013/0030714 A1 | 1/2013 | Ashby |

FOREIGN PATENT DOCUMENTS

| | | |
|---|---|---|
| WO | WO-2007022122 A2 | 2/2007 |
| WO | WO-2009140313 A1 | 11/2009 |
| WO | WO-2010012093 A1 | 2/2010 |
| WO | WO-2011159919 A2 | 12/2011 |

OTHER PUBLICATIONS

Altschul S.F., et al., "Gapped BLAST and PSI-BLAST: A New Generation of Protein Database Search Programs," Nucleic Acids Research, Sep. 1, 1997, vol. 25(17), pp. 3389-3402.
Anthony, C., "The Biochemistry of Methylotrophs," Academic Press, 1982, New York, pp. 2.
Ashby M. N., et al., "Serial Analysis of rRNA Genes and the Unexpected Dominance of Rare Members of Microbial Communities," Applied and Environmental Microbiology, vol. 73 (14), May 25, 2007, pp. 4532-4542, XP055145488, ISSN: 0099-2240, DOI: 10.1128/AEM.02956-06.
Bader J., et al., Journal of Applied Microbiology, vol. 109(2), Dec. 19, 2009, pp. 372-387.
Bäckhed F., et al., "Host-bacterial Mutualism in the Human Intestine," Science, The Inner Tube of Life, vol. 307(5717), Mar. 25, 2005, pp. 1915-1920.
Brooks A.G., et al., "Controls on Methane Production in a Tidal Freshwater Estuary and a Peatland: Methane Production via Acetate Fermentation and CO2 Reduction," Biogeochemistry, Jan. 2003, vol. 62 (1), pp. 19-37.
Budwill, "Microbial Methanogenesis and its Role in Enhancing Coalbed Methane Recovery," Canadian Society of Exploration Geophysicists Recorder, Oct. 2003, pp. 41-46.
Cartier N., et al., "Hematopoietic Stem Cell Gene Therapy with a Lentiviral Vector in X-linked Adrenoleukodystrophy," Science, vol. 326(5954), Nov. 6, 2009, pp. 818-823.
Chang W., et al., "Molecular Characterization of Anaerobic Microbial Communities from Benzene-Degrading Sediments under Methanogenic Conditions," Biotechnology Progress, vol. 21(6), Dec. 2, 2005, pp. 1789-1794, XP055145354, ISSN: 8756-7938, DOI: 10.1021/bp050250p.
Cho I., et al., "The Human Microbiome: At the Interface of Health and Disease," Nature Reviews Genetics, vol. 13(4), Apr. 2012, pp. 260-270.
Clarke S. D., et al., "Nutritional Control of Rat Liver Fatty Acid Synthase and S14 mRNA Abundance," Journal of Nutrition, vol. 120(2), Feb. 1990, pp. 218-224.
Colbert S.F., et al., "Use of an Exotic Carbon Source to Selectively Increase Metabolic Activity and Growth of Pseudomonas Putida in Soil," Applied and Environmental Microbiology, vol. 59(7), Jul. 1993, pp. 2056-2063.
Connon S.A., et al., "High-Throughput Methods for Culturing Microorganisms in Very-Low-Nutrient Media Yield Diverse New Marine Isolates," Applied and Environmental Microbiology, Aug. 2002, vol. 68(8), pp. 3878-3885.
Coutinho M., et al., "The Relationship between Glucose and Incident Cardiovascular Events. A Metaregression Analysis of Published Data from 20 Studies of 95,783 Individuals Followed for 12.4 years," Diabetes Care, vol. 22(2), Feb. 1999, pp. 233-240.
Crump B.C., et al., "Microbial Biogeography Along an Estuarine Salinity Gradient: Combined Influences of Bacterial Growth and Residence Time," Applied and Environmental Microbiology, vol. 70(3), Mar. 2004, pp. 1494-1505.
Database WPI, Week 201036, Thomas Scientific, London, XP-002662111, Oct. 31, 2011, 3 pages.
Davis J.B., et al., "Areal Contrasts in the Abundance of Hydrocarbon Oxidizing Microbes in Soils," Journal of Applied Microbiology, vol. 7(3), May 1959, pp. 156-165.
Devereux R., et al., "A Phylogenetic Tree of 16S rRNA Sequences from Sulfate-reducing Bacteria in a Sandy Marine Sediment," Applied and Environmental Microbiology, vol. 60(9), Sep. 1994, pp. 3437-3439.
Doerfert S.N., et al., "*Methanolobus zinderi* sp. Nov., a Methylotrophic Methanogen Isolated from a Deep Subsurface Coal Seam," Systematic and Evolutionary Microbiology, May 2009, vol. 59(Pt 5), pp. 1064-1069.
Dolfing J., et al., "Thermodynamic Constraints on Methanogenic Crude Oil Biodegradation," ISME Journal, Apr. 2008, vol. 2(4), pp. 442-452.
Duhamel M., et al., "Microbial composition of Chlorinated Ethene-Degrading Cultures Dominated by Dehalococcoides," FEMS Microbiology Ecology, vol. 58 (3), Dec. 1, 2006, pp. 538-549, XP055150707, ISSN: 0168-6496, DOI: 10.1111jj.1574-6941.2006.00191.x.
Dunbar J., et al., "Empirical and Theoretical Bacterial Diversity in Four Arizona Soils," Applied and Environmental Microbiology, vol. 68(6), Jun. 2002, pp. 3035-3045.
Elbing K., et al., Current Protocols in Molecular Biology, 2002, pp. 1.3.3-1.3.6.
Extended European Search Report dated Mar. 25, 2015 for European Application No. 11796451.0 filed on Jun. 16, 2011, 14 pages.
Faiz and Hendry, "Microbial Activity in Australian CBM Reservoirs," Search and Discovery Article #80033 (2009).
Farrelly V., et al., "Effect of Genome Size and rrn Gene Copy Number on PCR Amplification of 16S rRNA Genes from a Mixture of Bacterial Species," Applied and Environmental Microbiology, vol. 61(7), Jul. 1995, pp. 2798-2801.
Felske A., et al., "Phylogeny of the Main Bacterial 16S rRNA Sequences in Drentse A Grassland Soils (The Netherlands)," Applied and Environmental Microbiology, vol. 64 (3), Mar. 1998, pp. 871-879.
Fierer et al., Ecology, vol. 276, 2001, pp. 19937-19944.
GenBank, NCBI Nucleotide DB, see 16S rRNA sequence data of Acetobacterium carbinolicum, Accession No. AB546239.1, Feb. 16, 2010.
Grandin, U., Journal of Vegetation Science, vol. 17, 2006, pp. 843-844.
Green M.S., et al., "Characterization of a Methanogenic Consortium Enriched From a Coalbed Methane Well in the Powder River Basin, U.S.A.," Coal Geology, Oct. 2, 2008, vol. 76 (1-2), pp. 34-45.
Grosskopf R., et al., "Diversity and Structure of the Methanogenic Community in Anoxic Rice Paddy Soil Microcosms as Examined by Cultivation and Direct 16S rRNA Gene Sequence Retrieval," Applied and Environmental Microbiology, vol. 64(3), Mar. 1998, pp. 960-969.
Hofle, M.G., "Bacterioplankton Community Structure and Dynamics after Large-scale Release of Nonindigenous Bacteria as Revealed by Low-molecular-weight-RNA Analysis," Applied and Environmental Microbiology, vol. 58(10), Oct. 1992, pp. 3387-3394.
Hood M. A., et al., "Microbial Indicators of Oil-Rich Salt Marsh Sediments," Journal of Applied Microbiology, vol. 30(6), 1975, pp. 982-987.
Hugenholtz P., et al., "Impact of Culture-Independent Studies on the Emerging Phylogenetic View of Bacterial Diversity," Journal of Bacterial, vol. 180(18), Sep. 1998, pp. 4765-4774.
Hunt D. E., et al., "Evaluation of 23S rRNA PCR Primers for Use in Phylogenetic Studies of Bacterial Diversity," Applied and Environmental Microbiology, vol. 72(3), Mar. 2006, pp. 2221-2225.
International Preliminary Report on Patentability dated Dec. 19, 2012 for International Application No. PCT/US2011/040730, 9 pages.
International Preliminary Report on Patentability dated Dec. 19, 2012 for International Application No. PCT/US2011/040742, 7 pages.

(56) References Cited

OTHER PUBLICATIONS

International Search Report and Written Opinion for International Application No. PCT/US2011/040730, dated Jan. 11, 2012, 16 pages.
International Search Report and Written Opinion for International Application No. PCT/US2011/040742, dated Feb. 23, 2012, 12 pages.
Janssen P. H., "Identifying the Dominant Soil Bacterial Taxa in Libraries of 16S rRNA and 16S rRNA Genes," Applied and Environmental Microbiology, vol. 72(3), Mar. 1, 2006, pp. 1719-1728. XP055145462, ISSN: 0099-2240, DOI: 10.1128/AEM.72.3.1719-1728.2006.
Keeling et al., Forest Ecology and Management, vol. 237, 2006, pp. 418-428.
Kleinsteuber S., et al., "Population Dynamics within a Microbial Consortium during Growth on Diesel Fuel in Saline Environments," Applied and Environmental Microbiology, vol. 72(5), May 1, 2006, pp. 3531-3542, XP055145457, ISSN: 0099-2240, DOI: 10.1128/AEM.72.5.3531-3542.2006.
Land J.P., et al., "Nonseismic Methods can Provide Many Views of a Drillsite," Oil & Gas Journal, vol. 94, 1996, pp. 69-73.
Larsen N., et al., "The Ribosomal Database Project," Nucleic Acids Research, vol. 21 (13), Jul. 1, 1993, pp. 3021-3023.
Legendre et al., Ecological Monographs, vol. 69(1), Feb. 1999, pp. 1-24.
Leu J. Y., et al., "Identification and Phylogenetic Analysis of Thermophilic Sulfate-Reducing Bacteria in Oil Field Samples by 16S Rona Gene Cloning and Sequencing," Anaerobe, vol. 4, 1998, pp. 165-174.
Liu W.T., et al., "Characterization of Microbial Diversity by Determining Terminal Restriction Fragment Length Polymorphisms of Genes Encoding 16S rRNA," Applied and Environmental Microbiology, vol. 63, 1997, pp. 4516-4522.
Long A. D., et al., "Improved Statistical Inference from DNA Microarray Data Using Analysis of Variance and A Bayesian Statistical Framework Analysis of Global Gene Expression in *Escherichia coli*k12," Journal Biological Chemistry, vol. 276, 2001, pp. 19937-19944.
Marguiles E.H., et al., "eSAGE: Managing and Analyzing Data generated with Serial Analysis of Gene Expression (SAGE)," Bioinformatics, vol. 16 (7), 2000, pp. 650-651.
Margulies M., et al., "Genome Sequencing in Microfabricated High-Density Picolitre Reactors," Nature, Sep. 15, 2005, vol. 437 (7057), pp. 376-380.
Martiny J.B. et al., "Microbial Biogeography: Putting Microorganisms on the Map," Nature Reviews Microbiology, vol. 4(2), Feb. 2006, pp. 102-112.
Matsuki T., et al., "Distribution of Bifidobacterial Species in Human Intestinal Microflora Examined with 16S rRNA-gene-targeted Species-specific Primers," Applied and Environmental Microbiology, vol. 65 (10), Oct. 1999, pp. 4506-4512.
Mcinerney M.J., et al., "Syntrophy in Anaerobic Global Carbon Cycles," Current Opinions Biotechnology, vol. 20(6), Dec. 2009, pp. 623-632.
Mochimaru H., et al., "Methanogen Diversity in Deep Subsurface Gas-Associated Water at the Minami-Kanto Gas Field in Japan," Geomicrobiology, Apr. 11, 2007, vol. 24 (2), pp. 93-100.
Muyzer G., et al., "Profiling of Complex Microbial Populations by Denaturing Gradient Gel Electrophoresis Analysis of Polymerase Chain Reaction-Amplified Genes Coding for 16S rRNA," Applied and Environmental Microbiology, vol. 59(3), 1993, pp. 695-700.
NCBI Nucleotide DB, NCBI Reference sequence No. NR_026327.1 (Jan. 9, 2009)—see 16S rRNA sequence data of Acetobacterium paludosum.
Noble P.A., et al., "Natural Microbial Community Compositions Compared by a Back-Propagating Neutral Network and Cluster Analysis of 5s rRNA," Applied and Environmental Microbiology, vol. 63, 1997, pp. 1762-1770.
Non-final office action dated Jul. 1, 2013, for U.S. Appl. No. 13/566,945, filed Aug. 3, 2012, 23 pages.
Non-final office action dated Sep. 19, 2013, for U.S. Appl. No. 13/566,940, filed Aug. 3, 2012, 16 pages.
O'Malley M. A., "The Nineteenth Century Roots of Everything is Everywhere," Nature Reviews Microbiology, vol. 5, Aug. 2007, pp. 647-651.
Pace N.R., "A Molecular View of Microbial Diversity and the Biosphere," Science, vol. 276 (5313), 1997, pp. 734-740.
Partial Supplementary European Search Report dated Nov. 18, 2014 for European Application No. 11796451.0 filed on Jun. 16, 2011, 8 pages.
Penner T. J., et al., "Microbial Diversity of Western Canadian Subsurface Coal Beds and Methanogenic Coal Enrichment Cultures," International Journal of Coal Geology, vol. 82(1-2), 2010, pp. 81-93.
Relman D.A., "Detection and Identification of Previously Unrecognized Microbial Pathogens", Emerging Infectious Diseases Journal, vol. 4 (3), 1998, pp. 382-389.
Response mailed on Nov. 20, 2013, for Non-final office action dated Jul. 1, 2013 for U.S. Appl. No. 13/566,945, filed Aug. 3, 2012, 25 pages.
Response mailed on Nov. 20, 2013, for Non-final office action dated Sep. 19, 2013 for U.S. Appl. No. 13/566,940, filed Aug. 3, 2012, 23 pages.
Roh Y., et al., "Metal Reduction and Iron Biomineralization by a Psychrotolerant Fe(III)-reducing bacterium, *Shewanella* sp. Strain PV-4," Applied and Environmental Microbiology, May 2006, vol. 72 (5), pp. 3236-3244.
Sait M., et al., "Cultivation of Globally Distributed Soil Bacteria from Phylogenetic Lineages Previously Only Detected in Cultivation-Independent Surveys," Environmental Microbiology, Nov. 2002, vol. 4 (11), pp. 654-666.
Schink B, "Energetics of Syntrophic Cooperation in Methanogenic Degradation," Microbiology and Molecular Biology Reviews, Jun. 1997, vol. 61 (2), pp. 262-280.
Sealey J., "A Geomicrobiological Method of Prospecting for Petroleum," The Oil and Gas Journal, Apr. 1974, pp. 142-146.
Shelton D.R., et al., "General Method for Determining Anaerobic Biodegradation Potential," Applied and Environmental Microbiology, Apr. 1984 , vol. 47 (4), pp. 850-857.
Strapoc D., et al., "Methane-Producing Microbial Community in a Coal Bed of the Illinois Basin," Applied and Environmental Microbiology, Apr. 2008, vol. 74 (8), pp. 2424-2432.
Strebelle S., et al., "Using Multiple-Point Statistics to Build Geologically Realistic Reservoir Models: The MPS/FDM Workflow," The Future of Geological Modeling in Hydrocarbon Development, The Geological Society, London, Dec. 15, 2008, vol. 309, pp. 67-74.
Sugano A., et al., "Succession of Methanogenic Archaea in Rice Straw Incorporated into a Japanese Rice Field: Estimation by PCR-DGGE and Sequence Analyses," Archaea, vol. 1(6), Dec. 2005, pp. 391-397.
Telang A.J., et al., "Characterization of the Diversity of Sulfate-reducing Bacteria in Soil and Mining Waste Water Environments by Nucleic acid Hybridization Techniques," Canadian Journal of Microbiology, vol. 40 (11), Nov. 1994, pp. 955-964.
Thomas E.J., et al., "Sensitive and Specific Detection of Listeria Monocytogenes in Milk and Ground Beef with the Polymerase Chain Reaction," Applied and Environmental Microbiology, vol. 57(9), 1991, pp. 2576-2580.
Torsvik V., et al., "High Diversity in DNA of Soil Bacteria," Applied and Environmental Microbiology, vol. 56(3), Mar. 1990, pp. 782-787.
Tucker J., et al., "Detailed Microbial Surveys Help Improve Reservoir Characterization," Oil & Gas Journal, vol. 92, 1994, pp. 65-69.
Unrau P., et al., "Non-cloning Amplification of Specific DNA Fragments from Whole Genomic DNA digest using DNA Indexers," Gene, vol. 145(2), Aug. 1994, pp. 163-169.
Vandecasteele, et al., Genetic and Evolutionary Computational Conference, Late-Breaking Papers, 2003, pp. 1-4.
Velculescu V.E., et al., "Serial Analysis of Gene Expression," Science, vol. 270(5235), 1995, pp. 484-487.
Venter J.C., et al., "Environmental Genome Shotgun Sequencing of the Sargasso Sea," Science, Apr. 2, 2004, vol. 304 (5667), pp. 66-74.

(56) References Cited

OTHER PUBLICATIONS

Vinga S., et al., "Alignment-free Sequence Comparison—a Review," Bioinformatics, vol. 19(4), 2003, pp. 513-523.

Von Wintzingerode F., et al., "Determination of Microbial Diversity in Environmental Samples: Pitfalls of PCR-based rRNA Analysis," FEMS Microbiology Reviews, vol. 21(3), 1997, pp. 213-229.

Voordouw G., et al., "Characterization of 16S rRNA Genes from Oil Field Microbial Communities Indicates the Presence of a Variety of Sulfate-Reducing, Fermentative, and Sulfide-Oxidizing Bacteria," Applied and Environmental Microbiology, vol. 62, 1996, pp. 1623-1629.

Wang G.C., et al., "Frequency of Formation of Chimeric Molecules as a Consequence of PCR Coamplification of 16S rRNA Genes from Mixed Bacterial Genomes," Applied and Environmental Microbiology, vol. 63(12), 1997, pp. 4645-4650.

Whiticar M.J., et al., "Biogenic Methane Formation in Marine and Freshwater Environments: CO2 Reduction vs. Acetate Fermentation-Isotope Evidence," Geochimica et Cosmochimica Acta, May 1986, vol. 50 (5), pp. 693-709.

Wiksrom P., et al., "DNA Recovery and PCR Quantification of Catechol 2, 3-dioxygenase Genes from Different Soil Types," Journal of Biotechnology, vol. 52, 1996, pp. 107-120.

Wu J-Y., et al., "Effects of Polymerase, Template Dilution and Cycle Number on PCR Based 16S rRNA Diversity Analysis using the Deep Sequencing Method," Microbiology, vol. 10(255), 2010, pp. 1-7.

Zhang L., et al., "Gene Expression Profiles in Normal and Cancer Cells," Science, vol. 276(5316), 1997, pp. 1268-1272.

Zinder, Methanogens. In: Techniques in Microbial Ecology, Burlage, et al., Eds. J. Oxford University Press, 1998, pp. 113-136.

SEQUENCE LISTING

<160> NUMBER OF SEQ ID NOS: 12

<210> SEQ ID NO 1
<211> LENGTH: 242
<212> TYPE: DNA
<213> ORGANISM: acetobacterium

<400> SEQUENCE: 1
cacgccgtaa acgatgagtg ctaggtgttg gggagactca gtgccgcagc taacgcaata     60
agcactccgc ctggggagta cgaccgcaag gttgaaactc aaaggaattg acggggaccc    120
gcacaagcag cggagcatgt ggtttaattc gaagcaacgc gaagaacctt accaggtctt    180
gacatcctct gacaatctga gagatcagac tttcccttcg gggacagaga gacaggtggt    240
gc                                                                  242

<210> SEQ ID NO 2
<211> LENGTH: 242
<212> TYPE: DNA
<213> ORGANISM: Acetobacterium

<400> SEQUENCE: 2
cacgccgtaa acgatgagtg ctaggtgttg gggagactca gtgccgcagc taacgcaata     60
agcactccgc ctggggagta cgaccgcaag gttgaaactc aaaggaattg acggggaccc    120
gcacaagcag cggagcatgt ggtttaattc gaagcaacgc gaagaacctt accaggtctt    180
gacatcctct gacaacccaa gagattgggc tttcccttcg gggacagaga gacaggtggt    240
gc                                                                  242

<210> SEQ ID NO 3
<211> LENGTH: 242
<212> TYPE: DNA
<213> ORGANISM: Acetobacterium

<400> SEQUENCE: 3
cacgccgtaa acgatgagtg ctaggtgttg gggagactca gtgccgcagc taacgcaata     60
agcactccgc ctggggagta cgaccgcaag gttgaaactc aaaggaattg acggggaccc    120
gcacaagcag cggagcatgt ggtttaattc gaagcaacgc gaagaacctt accaggtctt    180
gacatcctct gacaatctga gagatcagac ttttccttcg ggaacagaga gacaggtggt    240
gc                                                                  242

<210> SEQ ID NO 4
<211> LENGTH: 242
<212> TYPE: DNA
<213> ORGANISM: Acetobacterium

<400> SEQUENCE: 4
cacgccgtaa acgatgagtg ctaggtgttg gggagactca gtgccgcagc taacgcaata     60
agcactccgc ctggggagta cgaccgcaag gttgaaactc aaaggaattg acggggaccc    120
gcacaagcag cggagcatgt ggtttaattc gaagcaacgc gaagaacctt accaggtctt    180
gacatcctct gaccatctga gagatcagac ttttccttcg ggaacagaga gacaggtggt    240
gc                                                                  242

<210> SEQ ID NO 5
<211> LENGTH: 242
<212> TYPE: DNA
<213> ORGANISM: Acetobacterium

<400> SEQUENCE: 5

```
cacgccgtaa acgatgagtg ctaggtgttg gggagactca gtgccgcagc taacgcaata    60
agcactccgc ctggggagta cgaccgcaag gttgaaactc aaaggaattg acggggaccc   120
gcacaagcag cggagcatgt ggtttaattc gaagcaacgc gaagaacctt accaggtctt   180
gacatcctct gaccatctga gagatcagac tttcccttcg ggacagaga dacaggtggt   240
gc                                                                  242
```

<210> SEQ ID NO 6
<211> LENGTH: 242
<212> TYPE: DNA
<213> ORGANISM: Acetobacterium

<400> SEQUENCE: 6

```
cacgccgtaa acgatgagtg ctaggtgttg gggagactca gtgccgcagc taacgcaata    60
agcactccgc ctggggagta cgaccgcaag gttgaaactc aaaggaattg acggggaccc   120
gcacaagcag cggagcatgt ggtttaattc gaagcaacgc gaagaacctt accaggtctt   180
gacatcctct gaccacccaa gagattgggc tttcccttcg ggacagaga dacaggtggt   240
gc                                                                  242
```

<210> SEQ ID NO 7
<211> LENGTH: 242
<212> TYPE: DNA
<213> ORGANISM: Acetobacterium

<400> SEQUENCE: 7

```
cacgccgtaa acgatgagtg ctaggtgttg gggagactca gtgccgcagc taacgcaata    60
agcactccgc ctggggagta cgaccgcaag gttgaaactc aaaggaattg acggggaccc   120
gcacaagcag cggagcatgt ggtttaattc gaagcaacgc gaagaacctt accaggtctt   180
gacatcctct gacaatccaa gagattgggc tttcccttcg ggacagaga dacaggtggt   240
gc                                                                  242
```

<210> SEQ ID NO 8
<211> LENGTH: 245
<212> TYPE: DNA
<213> ORGANISM: Bacteroides

<400> SEQUENCE: 8

```
cacgcagtaa acgatgatta ctagctgttt gcgatacaat gtaagcggct gagcgaaagc    60
gttaagtaat ccacctgggg agtacgttcg caagaatgaa actcaaagga attgacgggg   120
gcccgcacaa gcggaggaac atgtggttta attcgatgat acgcgaggaa ccttacccgg   180
gcttgaaatg catctgaccg gccttgaaag aggttttccc ttcggggcag atgtgtaggt   240
gctgc                                                               245
```

<210> SEQ ID NO 9
<211> LENGTH: 246
<212> TYPE: DNA
<213> ORGANISM: Spirochaetes

<400> SEQUENCE: 9

```
cgcacagtaa acgatgtgca ccaggtggcg ggggtagaac ccccggtacc gtagcaaacg    60
cattaagtgc accgcctggg gagtatgctc gcaagggtga aactcaaagg aattgacggg   120
```

```
ggcccgcaca agcggtggag catgtggttt aattcgatgg tacgcgagaa accttaccag      180
ggcttgacat acaccggaag cgccgtgaaa gcggcgtgcc gcttgcggcc ggtgaacagg      240
tgctgc                                                                246

<210> SEQ ID NO 10
<211> LENGTH: 243
<212> TYPE: DNA
<213> ORGANISM: Bacteroides

<400> SEQUENCE: 10
cacacagtaa acgatgaata ctcgctgttt gcgatataca gtaagcggcc aagcgaaagc       60
attaagtatt ccacctgggg agtacgccgg caacggtgaa actcaaagga attgacgggg      120
gcccgcacaa gcggaggaac atgtggttta attcgatgat acgcgaggaa ccttacccgg      180
gcttgaattg cagaggaaca tagttgaaag attatggccg caaggtctct gtgaaggtgc      240
tgc                                                                   243

<210> SEQ ID NO 11
<211> LENGTH: 243
<212> TYPE: DNA
<213> ORGANISM: Bacteroides

<400> SEQUENCE: 11
cacacagtaa acgatgaata ctcgctgttt gcgatataca gtaagcggcc aagcgaaagc       60
attaagtatt ccacctgggg agtacgccgg caacggtgaa actcaaagga attgacgggg      120
gcccgcacaa gcggaggaac atgtggttta attcgatgat acgcgaggaa ccttacccgg      180
gcttgaattg cagaggaata tagttgaaag attatcgccg caaggtctct gtgaaggtgc      240
tgc                                                                   243

<210> SEQ ID NO 12
<211> LENGTH: 243
<212> TYPE: DNA
<213> ORGANISM: Bacteroides

<400> SEQUENCE: 12
cacacagtaa acgatgaata ctcgctgttt gcgatataca gtaagcggcc aagcgaaagc       60
attaagtatt ccacctgggg agtacgccgg caacggtgaa actcaaagga attgacgggg      120
gcccgcacaa gcggaggaac atgtggttta attcgatgat acgcgaggaa ccttacccgg      180
gcttgaattg cagaggaata tagttgaaag attatagccg caaggtctct gtgaaggtgc      240
tgc                                                                   243
```

COMPOSITIONS AND METHODS FOR IDENTIFYING AND MODIFYING CARBONACEOUS COMPOSITIONS

RELATED APPLICATIONS

This application is a continuation of U.S. patent application Ser. No. 14/920,165, filed Oct. 22, 2015, which is a divisional of U.S. 371(c) patent application Ser. No. 13/504,120 filed Jun. 18, 2012 (now U.S. Pat. No. 9,206,680), which is a National Stage Entry of International (PCT) Patent Application No. PCT/US2011/040742 filed Jun. 16, 2011, which claims benefit of priority to U.S. Provisional Patent Application Nos. 61/355,488 filed Jun. 16, 2010, and 61/495,815 filed Jun. 10, 2011, all of which are expressly incorporated by reference herein in their entireties for all purposes.

SEQUENCE LISTING

This application contains a sequence listing, submitted electronically in ASCII format under the filename Sequence_Listing.txt, which is incorporated by reference herein in its entirety. The ASCII copy of the sequence listing was created on Dec. 29, 2017, and is 6,012 bytes in size.

FIELD OF THE INVENTION

This invention generally relates to natural gas and methylotrophic energy generation, bio-generated fuels and microbiology. In alternative embodiments, the invention provides compositions and methods for methanol-utilizing methanogenesis, or "methylotrophic"-conversion, including utilizing methylamines and other methyl-containing intermediates. In alternative embodiments, the invention provides nutrient amendments and microbial compositions that are both specifically optimized to stimulate methanogenesis from coal or other subsurface carbonaceous materials. In alternative embodiments, the invention provides methods to develop nutrient amendments and microbial compositions that are both specifically optimized to stimulate methanogenesis in a given reservoir.

BACKGROUND OF THE INVENTION

The methanogenic degradation of subsurface carbonaceous material is of significant commercial interest for a variety of reasons including production of natural gas (including methane). Methane is a predominant end-product of anaerobic microbially-mediated organic-matter decomposition following a variety of carbon-pathways and intermediate steps.

Recent technological advances have enabled characterization of microbial communities and the biogeochemical processes that take place in the subsurface. These processes generally occur under non-ideal conditions due to limiting nutrients and sub-optimal microbial community structure. Under normal sub-surface conditions, microbial gas formed in these natural "bioreactors" is generated at very slow rates due to limited nutrients and/or other environmental conditions, e.g., suboptimal water chemistry, pH, salinity and the like.

SUMMARY

In alternative embodiments, the invention provides compositions, bioreactors, reservoirs, products of manufacture, fluids or muds, or synthetic consortiums (e.g., manufactured groups of organisms) comprising a plurality of microorganism strains, wherein the microorganism strains comprise:

(a) at least two, three, four, five, six, seven, eight, nine, ten or eleven or all twelve of the microorganism strains of Consort-ABS1; or (b) a group (or "consortium") of different microorganism strains comprising at least two, three, four, five, six, seven, eight, nine, ten, eleven or twelve different microorganism strains, each strain comprising at least one 16S rRNA gene or nucleic acid sequence selected from the group consisting of a nucleic acid having at least about 90%, 91%, 92%, 93%, 94%, 95%, 96%, 97%, 98%, 99% or 100% (complete) sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:8, SEQ ID NO:10, SEQ ID NO:11 and SEQ ID NO:12, or (c) a group (or "consortium") of different microorganism strains consisting of at least two, three, four, five, six, seven, eight, nine, ten, eleven or twelve different microorganism strains, each strain comprising at least one 16S rRNA gene or nucleic acid sequence selected from the group consisting of a nucleic acid having at least about 90%, 91%, 92%, 93%, 94%, 95%, 96%, 97%, 98%, 99% or 100% (complete) sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:8, SEQ ID NO:10, SEQ ID NO:11 and SEQ ID NO:12, wherein optionally each member of the group (or "consortium") of different microorganism strains is a different microorganism strain, or each member of the group (or "consortium") of different microorganism strains has a different 16S rRNA gene or nucleic acid sequence, and optionally the at least one 16S rRNA gene or nucleic acid sequence comprises a subsequence (a portion) of a 16S rRNA sequence that optionally includes (comprises) the fifth and sixth variable (V5 and V6) regions of a 16S rRNA gene, and optionally the reservoir is an in situ subsurface reservoir, a surface reservoir, a synthetic reservoir or an excavated reservoir.

In alternative embodiments of the compositions, bioreactors, reservoirs, products of manufacture, fluids, muds and/or synthetic consortiums:

(i) at least 1, 2, 3, 4, 5, 6, 7, 8, 9, 10, 11 or all 12 of the microorganism strains comprise a member of the genus *Acetobacterium*, a member of the genus *Bacteroidetes* and/or a member of the genus *Spirochaetes*; or (ii) at least 1, 2, 3, 4, 5, 6, 7, 8, 9 or 10 of the microorganism strains comprise a member of the genus *Acetobacterium*, a member of the genus *Bacteroidetes* and a member of the genus *Spirochaetes*.

In alternative embodiments, the invention provides methods of identifying and/or characterizing one or more microbes in a subsurface methanogenic microbial community, or identifying and/or characterizing a nutrient composition that is customized for a specific subsurface methanogenic microbial community, comprising:

(a) obtaining or providing one or a set of samples from a subsurface carbonaceous formation or formations, wherein optionally the samples comprise a production water, or the samples are taken from a core, cuttings or outcrop sample and optionally the subsurface carbonaceous formation or formations comprises a coal formation, or a peat, or a lignite, or a bituminous coal, or an anthracite coal, or a volcanic ash, or a lignite or a lignin or lignin-comprising composition, a coal or a coal analogue(s) or a precursor(s) thereof, heavy oil, asphaltenes, and/or an organic debris;

(b) determining and/or characterizing the microbial composition, or the methanogenic strains (e.g., a phylogenetic analysis) of the sample or samples, wherein optionally all or substantially most of the microbes in the sample or samples are characterized or identified, or optionally all or substantially most of the methanogenic microbes (the methanogens, or methanogenic strains) in the sample or samples are characterized or identified; and (c) (i) identifying and/or characterizing one or more microbes in the sample or samples that are the most (or relatively more) methanogenic, identifying and/or characterizing one or more microbes in the sample or samples that are the most abundant methanogens, identifying and/or characterizing one or more microbes in the sample or samples whose distributions are (or distribution is) correlated with that of most other methanogens in the sample, or whose distributions are (or distribution is) correlated with the highest level of methanogenesis in the sample, and/or identifying unfavorable endemic microbes or conditions showing negative correlation to biogas formation; or (ii) applying to the sample or samples a plurality of (a variety of) nutrients mixes and determining a consensus and/or optimal (optimal for methanogenesis) nutrient mix, wherein optionally the consensus and/or optimal nutrient mix is at least initially based upon known requirements of methanogenic microbes, or organisms associated with methanogenic microbes, and/or field observations of subsurface methanogenic environments, and optionally the sample or samples comprise a subset of the microbial composition of the sample or samples of step (b), or a subset of the methanogenic organisms identified or characterized in step (b), or a set of methanogenic organisms identified or characterized in step (c), and optionally the consensus and/or optimal nutrient mix is also designed to decrease the amount of other (non-methanogenic) bacterial processes affecting biogas formation, or to provide an environment unfavorable to endemic microbes or conditions that show a negative correlation to biogas (e.g., methane) formation.

In alternative embodiments, the methods further comprise introducing the consensus or optimal nutrient mix of 3(c)(ii) to a methanogenic microbial community; wherein optionally the methanogenic microbial community is in situ in subsurface methanogenic microbial community.

In alternative embodiments, the microbial composition of step 3(b) is determined and or characterized by nucleic acid (e.g., DNA, RNA) sequencing all or a portion of an rRNA gene; or a 16S rRNA gene. In alternative embodiments, the microbial composition of step 3(b) is determined by a chemical, microbiological or any analytical method.

In alternative embodiments, the chemical or microbiological analytical method comprises a fatty acid methyl ester analysis, a membrane lipid analysis and/or a cultivation-dependent method.

In alternative embodiments, the methanogenic organisms (methanogenic strains) comprise one or more members of the Archaea family, or are anaerobic organisms, or are autotrophs or chemoheterotrophs; or the methanogenic organisms comprise one or more members of a genus selected from the group consisting of *Methanolobus, Methanobacterium, Methanothermobacter, Methanogenium, Methanogenium, Methanofollis, Methanoculleus, Methanocorpusculum, Methanococcus, Methanocalculus, Methanobrevibacter* and *Methanosarcina*; or the methanogenic organisms (methanogenic strains) comprise or consist of at least one synthetic consortium of the invention, or one or more members selected from the group consisting of:

*Methanolobus bornbayensis*
*Methanolobus taylorii*
*Methanolobus profundi*
*Methanolobus zinderi*
*Methanobacterium bryantii*
*Methanobacterium formicum*
*Methanobrevibacter arboriphilicus*
*Methanobrevibacter gottschalkii*
*Methanobrevibacter ruminantium*
*Methanobrevibacter smithii*
*Methanocalculus chunghsingensis*
*Methanococcoides burtonii*
*Methanococcus aeolicus*
*Methanococcus deltae*
*Methanococcus jannaschii*
*Methanococcus maripaludis*
*Methanococcus vannielii*
*Methanocorpusculum labreanum*
*Methanoculleus bourgensis* (*Methanogenium olentangyi* & *Methanogenium bourgense*)
*Methanoculleus marisnigri*
*Methanofollis liminatans*
*Methanogenium cariaci*
*Methanogenium frigidum*
*Methanogenium organophilum*
*Methanogenium wolfei*
*Methanomicrobium mobile*
*Methanopyrus kandleri*
*Methanoregula boonei*
*Methanosaeta concilii*
*Methanosaeta thermophila*
*Methanosarcina acetivorans*
*Methanosarcina barkeri*
*Methanosarcina mazei*
*Methanosphaera stadtmanae*
*Methanospirillium hungatei*
*Methanothermobacter defluvii* (*Methanobacterium defluvii*)
*Methanothermobacter thermautotrophicus* (*Methanobacterium thermoautotrophicum*)
*Methanothermobacter thermoflexus* (*Methanobacterium thermoflexum*)
*Methanothermobacter wolfei* (*Methanobacterium wolfei*), and
*Methanothrix sochngenii*

In alternative embodiments, the invention provides methods of determining a nutrient composition that is customized or optimal for a specific subsurface methanogenic microbial community comprising the following steps:

a. obtaining a sample or a set of samples from one or more subsurface carbonaceous formation(s) of interest, wherein optionally the subsurface carbonaceous formation or formations comprises a coal formation, or a peat, or a lignite, or a bituminous coal, or an anthracite coal, or a coal analogue(s) or a precursor(s) thereof, a heavy oil, asphaltenes, and/or an organic debris;

b. determining or characterizing the microbial composition of the methanogenic microbial community of the sample or samples; and c. growing or culturing one or more enrichment cultures of all or a subset of the microbial composition on a carbonaceous substrate, a chemical analog, a methanogenic substrate or a combination thereof, wherein optionally the enrichment cultures are designed to distinguish different methanogenic pathways, and (i) identifying and/or characterizing one or more methanogens grown or cultured in the enrichment culture or cultures whose distribution strongly correlates with a high methanogenesis rate; and/or (ii) identifying one or more microbes present in the sample or samples whose distribution correlates with that of a methanogen in the sample, or whose distribution correlates with that of a methanogen(s) identified in step (c)(i).

In alternative embodiments the methods further comprise designing a nutrient mix for optimizing growth of the methanogen(s) and/or optimizing methanogenic activity, wherein optionally the nutrient mix is at least initially based on one or more requirements, or a range of requirements, of methanogenic microbes or microbes associated with methanogens as identified through literature searches, field observations of subsurface methanogenic environments and/or cultivation experiments, and optionally the nutrient mix is also designed to decrease the amount of other (non-methanogenic) bacterial processes negatively affecting biogas formation.

In alternative embodiments the methods further evaluating the effect of nutrient concentration variations on methanogenesis rates in test cultures using endemic carbonaceous substrates. In alternative embodiments the methods further comprise introducing the nutrient mix to a methanogenic microbial community, wherein optionally the methanogenic microbial community is in situ in a subsurface carbonaceous formation.

In alternative embodiments, the samples comprise a production water, or the samples are taken from a core sample.

In alternative embodiments, the invention provides methods for improving methylotrophic biogas formation in situ in a subsurface carbonaceous formation comprising:

(a) administering one or more methanogenic organisms identified in a method of the invention, or at least one synthetic consortium of the invention, to the subsurface carbonaceous formation or formations, or (b) administering one or more methanogenic organisms, wherein optionally the methanogenic organisms comprise one or more members of the Archaea family, or are anaerobic organisms, or are autotrophs or chemoheterotrophs, and optionally the methanogenic organisms comprise one or more members of a genus selected from the group consisting of *Methanolobus, Methanobacterium, Methanothermobacter, Methanogenium, Methanogenium, Methanofollis, Methanoculleus, Methanocorpusculum, Methanococcus, Methanocalculus, Methanobrevibacter* and *Methanosarcina,* and optionally the methanogenic organisms comprise: at least one synthetic consortium of the invention, or one or more members selected from the group consisting of:

*Methanolobus bornbayensis*
*Methanolobus taylorii*
*Methanolobus profundi*
*Methanolobus zinderi*
*Methanobacterium bryantii*
*Methanobacterium formicum*
*Methanobrevibacter arboriphilicus*
*Methanobrevibacter gottschalkii*
*Methanobrevibacter ruminantium*
*Methanobrevibacter smithii*
*Methanocalculus chunghsingensis*
*Methanococcoides burtonii*
*Methanococcus aeolicus*
*Methanococcus deltae*
*Methanococcus jannaschii*
*Methanococcus maripaludis*
*Methanococcus vannielii*
*Methanocorpusculum labreanum*
*Methanoculleus bourgensis* (*Methanogenium olentangyi* & *Methanogenium bourgense*)
*Methanoculleus marisnigri*
*Methanofollis liminatans*
*Methanogenium cariaci*
*Methanogenium frigidum*
*Methanogenium organophilum*
*Methanogenium wolfei*
*Methanomicrobium mobile*
*Methanopyrus kandleri*
*Methanoregula boonei*
*Methanosaeta concilii*
*Methanosaeta thermophila*
*Methanosarcina acetivorans*
*Methanosarcina barkeri*
*Methanosarcina mazei*
*Methanosphaera stadtmanae*
*Methanospirillium hungatei*
*Methanothermobacter defluvii* (*Methanobacterium defluvii*)
*Methanothermobacter thermautotrophicus* (*Methanobacterium thermoautotrophicum*)
*Methanothermobacter thermoflexus* (*Methanobacterium thermoflexum*)
*Methanothermobacter wolfei* (*Methanobacterium wolfei*), and
*Methanothrix sochngenii* wherein optionally the one or more methanogenic organisms have been enriched using the consensus and/or optimal nutrient mix identified in a method of the invention, wherein optionally the subsurface carbonaceous formation is modified to have properties more like or similar to one or more properties of the optimal nutrient mix and optionally the subsurface carbonaceous formation or formations comprises a coal formation, or a peat, or a lignite, or a bituminous coal, or an anthracite coal, or a coal or a coal analogue(s) or a precursor(s) thereof, heavy oil, asphaltenes, and/or an organic debris.

In alternative embodiments, the invention provides methods for improving methylotrophic biogas formation in situ in a subsurface carbonaceous formation or formations comprising:

(a) (1) administering one or more methanogenic organisms identified in a method of the invention, or at least one synthetic consortium of the invention, to the subsurface carbonaceous formation or formations, wherein optionally the subsurface carbonaceous formation or formations comprises a coal formation, or a peat, or a lignite, or a bituminous coal, or an anthracite coal, a coal or a coal analogue(s) or a precursor(s) thereof, heavy oil, asphaltenes, and/or an organic debris, or (2) administering one or more methanogenic organisms, wherein optionally the methanogenic organisms comprise one or more members of the Archaea family, or are anaerobic organisms, or are autotrophs or chemoheterotrophs, and optionally the methanogenic organisms comprise one or more members of a genus selected from the group consisting of *Methanolobus, Methanobacterium, Methanothermobacter, Methanogenium, Methanogenium, Methanofollis, Methanoculleus, Methanocorpusculum, Methanococ-*

*cus, Methanocalculus, Methanobrevibacter* and *Methanosarcina*, or the methanogenic organisms comprise: at least one synthetic consortium of the invention, or one or more members selected from the group consisting of:

*Methanolobus bornbayensis*
*Methanolobus taylorii*
*Methanolobus profundi*
*Methanolobus zinderi*
*Methanobacterium bryantii*
*Methanobacterium formicum*
*Methanobrevibacter arboriphilicus*
*Methanobrevibacter gottschalkii*
*Methanobrevibacter ruminantium*
*Methanobrevibacter smithii*
*Methanocalculus chunghsingensis*
*Methanococcoides burtonii*
*Methanococcus aeolicus*
*Methanococcus deltae*
*Methanococcus jannaschii*
*Methanococcus maripaludis*
*Methanococcus vannielii*
*Methanocorpusculum labreanum*
*Methanoculleus bourgensis (Methanogenium olentangyi & Methanogenium bourgense)*
*Methanoculleus marisnigri*
*Methanofollis liminatans*
*Methanogenium cariaci*
*Methanogenium frigidum*
*Methanogenium organophilum*
*Methanogenium wolfei*
*Methanomicrobium mobile*
*Methanopyrus kandleri*
*Methanoregula boonei*
*Methanosaeta concilii*
*Methanosaeta thermophila*
*Methanosarcina acetivorans*
*Methanosarcina barkeri*
*Methanosarcina mazei*
*Methanosphaera stadtmanae*
*Methanospirillium hungatei*
*Methanothermobacter defluvii (Methanobacterium defluvii)*
*Methanothermobacter thermautotrophicus (Methanobacterium thermoautotrophicum)*
*Methanothermobacter thermoflexus (Methanobacterium thermoflexum)*
*Methanothermobacter wolfei (Methanobacterium wolfei),* and
*Methanothrix sochngenii;* or (b) the method of (a), further comprising:
(i) applying (before, during and/or after administering the organisms) to the subsurface carbonaceous formation an optimal nutrient mix, or the optimal nutrient mix identified in any of claims 3 to 15;
(ii) modifying (before, during and/or after administering the organisms) the subsurface carbonaceous formation to have properties more like or similar to one or more properties of the optimal nutrient mix; or
(iii) a combination of both (i) and (ii).

In alternative embodiments of the methods, the methanogenic organisms and/or nutrient mix can (are designed to) decrease the amount of other (non-methanogenic) bacterial processes negatively affecting biogas formation, wherein optionally bacterial processes affecting sulfate-reduction and biohydrogen consumption via acetogenesis or non-methanogenic hydrogenotrophic pathways are reduced.

In alternative embodiments, the invention provides methods of enhancing methanogenic rates in subsurface carbonaceous reservoirs comprising injecting one or more methanogenic organisms into the subsurface carbonaceous reservoir, wherein the one or more methanogenic organisms comprise: at least one synthetic consortium of the invention, one or more members of the Archaea family, or are anaerobic organisms, or are autotrophs or chemoheterotrophs, wherein optionally the subsurface carbonaceous reservoir comprises a coal formation, or a peat, or a lignite, or a bituminous coal, or an anthracite coal, a coal or a coal analogue(s) or a precursor(s) thereof, heavy oil, asphaltenes, and/or an organic debris.

In alternative embodiments of the methods, one or more methanogenic organisms comprise one or more members of a genus selected from the group consisting of *Methanolobus, Methanobacterium, Methanothermobacter, Methanogenium, Methanogenium, Methanofollis, Methanoculleus, Methanocorpusculum, Methanococcus, Methanocalculus, Methanobrevibacter* and *Methanosarcina*, or the one or more methanogenic organisms comprise: at least one synthetic consortium of the invention, or one or more members selected from the group consisting of:

*Methanolobus bornbayensis*
*Methanolobus taylorii*
*Methanolobus profundi*
*Methanolobus zinderi*
*Methanobacterium bryantii*
*Methanobacterium formicum*
*Methanobrevibacter arboriphilicus*
*Methanobrevibacter gottschalkii*
*Methanobrevibacter ruminantium*
*Methanobrevibacter smithii*
*Methanocalculus chunghsingensis*
*Methanococcoides burtonii*
*Methanococcus aeolicus*
*Methanococcus deltae*
*Methanococcus jannaschii*
*Methanococcus maripaludis*
*Methanococcus vannielii*
*Methanocorpusculum labreanum*
*Methanoculleus bourgensis (Methanogenium olentangyi & Methanogenium bourgense)*
*Methanoculleus marisnigri*
*Methanofollis liminatans*
*Methanogenium cariaci*
*Methanogenium frigidum*
*Methanogenium organophilum*
*Methanogenium wolfei*
*Methanomicrobium mobile*
*Methanopyrus kandleri*
*Methanoregula boonei*
*Methanosaeta concilii*
*Methanosaeta thermophila*
*Methanosarcina acetivorans*
*Methanosarcina barkeri*
*Methanosarcina mazei*
*Methanosphaera stadtmanae*
*Methanospirillium hungatei*
*Methanothermobacter defluvii (Methanobacterium defluvii)*
*Methanothermobacter thermautotrophicus (Methanobacterium thermoautotrophicum)*
*Methanothermobacter thermoflexus (Methanobacterium thermoflexum)*

*Methanothermobacter wolfei* (*Methanobacterium wolfei*), and

*Methanothrix sochngenii*

In alternative embodiments, the invention provides compositions, formulations, fluids, muds, or nutrient mixes for enhancing methanogenic rates in subsurface carbonaceous reservoirs comprising:

(i) one or more methanogenic organisms selected from the group consisting of a member of the Archaea family, an anaerobic organism, an autotroph, a chemoheterotroph or a combination thereof;

(ii) at least one synthetic consortium of the invention, or (iii) the one or more methanogenic organisms of (i) and a consensus and/or optimal nutrient mix identified in a method of the invention, wherein optionally the subsurface carbonaceous reservoir comprises a coal formation, or a peat, or a lignite, or a bituminous coal, or an anthracite coal, a coal or a coal analogue(s) or a precursor(s) thereof, heavy oil, asphaltenes, and/or an organic debris.

In alternative embodiments, the one or more methanogenic organisms comprise one or more members of a genus selected from the group consisting of *Methanolobus, Methanobacterium, Methanothermobacter, Methanogenium, Methanogenium, Methanofollis, Methanoculleus, Methanocorpusculum, Methanococcus, Methanocalculus, Methanobrevibacter* and *Methanosarcina*, or the one or more methanogenic organisms comprise one or more members selected from the group consisting of:

*Methanolobus bornbayensis*
*Methanolobus taylorii*
*Methanolobus profundi*
*Methanolobus zinderi*
*Methanobacterium bryantii*
*Methanobacterium formicum*
*Methanobrevibacter arboriphilicus*
*Methanobrevibacter gottschalkii*
*Methanobrevibacter ruminantium*
*Methanobrevibacter smithii*
*Methanocalculus chunghsingensis*
*Methanococcoides burtonii*
*Methanococcus aeolicus*
*Methanococcus deltae*
*Methanococcus jannaschii*
*Methanococcus maripaludis*
*Methanococcus vannielii*
*Methanocorpusculum labreanum*
*Methanoculleus bourgensis* (*Methanogenium olentangyi* & *Methanogenium bourgense*)
*Methanoculleus marisnigri*
*Methanofollis liminatans*
*Methanogenium cariaci*
*Methanogenium frigidum*
*Methanogenium organophilum*
*Methanogenium wolfei*
*Methanomicrobium mobile*
*Methanopyrus kandleri*
*Methanoregula boonei*
*Methanosaeta concilii*
*Methanosaeta thermophila*
*Methanosarcina acetivorans*
*Methanosarcina barkeri*
*Methanosarcina mazei*
*Methanosphaera stadtmanae*
*Methanospirillium hungatei*
*Methanothermobacter defluvii* (*Methanobacterium defluvii*)
*Methanothermobacter thermautotrophicus* (*Methanobacterium thermoautotrophicum*)
*Methanothermobacter thermoflexus* (*Methanobacterium thermoflexum*)
*Methanothermobacter wolfei* (*Methanobacterium wolfei*), and
*Methanothrix sochngenii*

In alternative embodiments, the invention provides methods of creating a microbial composition to enhance methanogenic degradation of carbonaceous substrates comprising the following steps:

a. obtaining a sample from a subsurface carbonaceous formation(s) of interest, wherein optionally the sample comprises a water sample, or a production water sample;

and optionally the subsurface carbonaceous formation(s) comprises a coal formation, or a peat, or a lignite, or a bituminous coal, or an anthracite coal, or a coal or a coal analogue(s) or a precursor(s) thereof, heavy oil, asphaltenes, and/or an organic debris, b. using the sample to inoculate an enrichment culture comprising a carbonaceous material of interest, and/or a chemical analogue thereof, as carbon source;

c. incubating the enrichment culture until growth of an organism is detected, wherein optionally the organism is a member of a methanogenic community; and d. introducing the cells detected in (c) into a subsurface formation, wherein optionally the cells are introduced by a method comprising injection at a well head.

In alternative embodiments, the enrichment culture is passaged into fresh medium at least one time. In alternative embodiments, the cells are co-injected into the subsurface formation with an optimized nutrient mix.

In alternative embodiments, the invention provides products of manufacture, fluids, muds, bioreactors or surface or subsurface reservoirs, for generating a biogas comprising: (a) production water, (b) a carbonaceous material of interest and/or a chemical analogue thereof as a carbon source; and (c) a composition or a composition, formulation, fluid or nutrient mix of the invention, or at least one synthetic consortium of the invention. In alternative embodiments, the carbonaceous material or carbon source comprises or further comprises a coal, a bituminous coal, an anthracite coal, a volcanic ash, or a lignite or a lignin or lignin-comprising composition, a coal or a coal analogues or a precursors thereof, heavy oil, asphaltenes, and/or an organic debris.

In alternative embodiments, the product of manufacture, fluid, mud, reservoir or bioreactor is contained in situ in a subsurface excavation or is contained in an artificial structure, or the product of manufacture or bioreactor is placed in or contained in a landfill or a subsurface carbonaceous reservoir or source. In alternative embodiments, the product of manufacture or bioreactor is a sand-pack bioreactor or a coal bioreactor.

In alternative embodiments, the biogas comprises methane, or the biogas mainly (or substantially) comprises methane.

In alternative embodiments, the following parameters are controlled and/or modified in the product of manufacture or bioreactor: i) type of organic matter (plant vs algae derived), ii) thermal maturity of organic matter (level of aromaticity and hence recalcitrance), iii) formation water chemistry (i.e. salinity, pH, inorganic and organic water chemistry), iv) temperature, and v) presence of appropriate syntrophic bacterial community able to provide specific methanogenic substrates.

In alternative embodiments, nutrients to enhance biogas formation are provided to the product of manufacture or bioreactor. In alternative embodiments, the nutrients to enhance biogas formation comprise metal salts of compounds found in methylotrophic/bacterial enzymes, non-inhibitory level of alternate electron acceptors such as iron, manganese, or other nutrients and trace elements identified by correlating nutrient abundance to microbial growth/methane production.

In alternative embodiments, the environmental parameters in the bioreactor are modified to enhance biogas formation. In alternative embodiments, the environmental parameters comprise formation or composition of water, pH of water (e.g., higher pH to the optimal range of the microbial association from culture experiments at the reservoir temperature).

In alternative embodiments, the microbial populations and/or the environmental parameters in the bioreactor are manipulated or shifted towards more efficient coal/kerogen biodegrading, or more efficient Cook Inlet methanol/methyl-generating, or for increasing the methanogenesis rates.

In alternative embodiments, the products of manufacture, fluids, muds, reservoirs, bioreactors or surface or subsurface reservoirs comprise use of methylotrophic (methanol and other methyl-providing) substrates under neutral to slightly alkaline conditions to enhance biogas formation, wherein optionally the slightly alkaline conditions comprise conditions of between about pH 7.5 to 9, or at least about pH 7.5, pH 8, pH 8.5, or pH 9.

In alternative embodiments, the products of manufacture, fluids, muds, reservoirs, bioreactors or surface or subsurface reservoirs comprise use of compositions and/or fluids to prevent or slow build up of volatile fatty acids such as propionic acid and/or to prevent or slow a pH drop that would inhibit methanogenesis.

In alternative embodiments, a nutrient mixture or composition, or the compositions and/or fluids, are introduced into a product of manufacture, fluid or bioreactor or a bioreactor reservoir through injection of a single bolus or through a continuous process. In alternative embodiments, newly generated biogas is monitored and/or traced from gas isotopes, using $^{14}$C-, $^{13}$C-, $^{2}$H- or $^{3}$H-enriched methanogenic substrates, and optionally the methanogenic substrates comprise bicarbonate, lignin and/or aromatic monomers.

In alternative embodiments, the invention provides methods for improving methylotrophic biogas formation in situ in a subsurface source or formation or an isolated, mined or excavated carbonaceous source or formation, comprising:

(a) administering to or contacting the subsurface source or formation or isolated, mined or excavated carbonaceous source or formation: at least one synthetic consortium of the invention, or one or more methanogenic organisms identified in a method of the invention, or (b) administering to or contacting the subsurface source or formation or isolated, mined or excavated carbonaceous source or formation: one or more methanogenic organisms, wherein optionally the methanogenic organisms comprise one or more members of the Archaea family, or are anaerobic organisms, or are autotrophs or chemoheterotrophs, and optionally the methanogenic organisms comprise one or more members of a genus selected from the group consisting of *Methanolobus, Methanobacterium, Methanothermobacter, Methanogenium, Methanogenium, Methanofollis, Methanoculleus, Methanocorpusculum, Methanococcus, Methanocalculus, Methanobrevibacter* and *Methanosarcina*, or the methanogenic organisms comprise one or more members selected from the group consisting of:

*Methanolobus bornbayensis*
*Methanolobus taylorii*
*Methanolobus profundi*
*Methanolobus zinderi*
*Methanobacterium bryantii*
*Methanobacterium formicum*
*Methanobrevibacter arboriphilicus*
*Methanobrevibacter gottschalkii*
*Methanobrevibacter ruminantium*
*Methanobrevibacter smithii*
*Methanocalculus chunghsingensis*
*Methanococcoides burtonii*
*Methanococcus aeolicus*
*Methanococcus deltae*
*Methanococcus jannaschii*
*Methanococcus maripaludis*
*Methanococcus vannielii*
*Methanocorpusculum labreanum*
*Methanoculleus bourgensis* (*Methanogenium olentangyi* & *Methanogenium bourgense*)
*Methanoculleus marisnigri*
*Methanofollis liminatans*
*Methanogenium cariaci*
*Methanogenium frigidum*
*Methanogenium organophilum*
*Methanogenium wolfei*
*Methanomicrobium mobile*
*Methanopyrus kandleri*
*Methanoregula boonei*
*Methanosaeta concilii*
*Methanosaeta thermophila*
*Methanosarcina acetivorans*
*Methanosarcina barkeri*
*Methanosarcina mazei*
*Methanosphaera stadtmanae*
*Methanospirillium hungatei*
*Methanothermobacter defluvii* (*Methanobacterium defluvii*)
*Methanothermobacter thermautotrophicus* (*Methanobacterium thermoautotrophicum*)
*Methanothermobacter thermoflexus* (*Methanobacterium thermoflexum*)
*Methanothermobacter wolfei* (*Methanobacterium wolfei*), and
*Methanothrix sochngenii* wherein optionally the one or more methanogenic organisms have been enriched using the consensus and/or optimal nutrient mix identified in any of claims 3 to 15, or the composition, formulation, fluid or nutrient mix of any of claims 22 to 24, wherein optionally the subsurface carbonaceous formation is modified to have properties more like or similar to one or more properties of the optimal nutrient mix and optionally the subsurface carbonaceous formation or formations comprises a coal formation, or a peat, or a lignite, or a bituminous coal, or an anthracite coal.

In alternative embodiments, the invention provides methods for processing a heavy oil, or decreasing the viscosity of a heavy oil by converting high molecular weight hydrocarbons into lower molecular weight hydrocarbons, or converting a heavy oil, a bitumen, a tar-sand, or equivalents, to a less viscous from, or to a gaseous light gas, gas and/or diesel product, wherein optionally the less viscous form of the heavy oil, bitumen, tar-sand or equivalents comprises substantially from C1 to about C24 hydrocarbons, comprising:

(a) injecting: at least one synthetic consortium of the invention, and/or one or more methanogenic organisms, into a subsurface carbonaceous reservoir comprising a heavy oil, a bitumen, a tars—and, or equivalents, or (b) contacting the heavy oil, a coal, a bitumen, a tars— and, or equivalent with: at least one synthetic consortium of the invention, or a composition comprising one or more methanogenic organisms, wherein optionally the contacting is in situ (e.g., in a ground formation or a subsurface carbonaceous reservoir), or a man-made reservoir or product of manufacture, or an excavated, mined, drilled or isolated heavy oil, bitumen, tar-sand, or equivalent, wherein the one or more methanogenic organisms comprise one or more members of the Archaea family, or are anaerobic organisms, or are autotrophs or chemoheterotrophs, wherein optionally the subsurface carbonaceous reservoir comprises a coal formation, or a peat, or a lignite, or a bituminous coal, or an anthracite coal.

In alternative embodiments of the methods, the one or more methanogenic organisms comprise one or more members of a genus selected from the group consisting of *Methanolobus, Methanobacterium, Methanothermobacter, Methanogenium, Methanogenium, Methanofollis, Methanoculleus, Methanocorpusculum, Methanococcus, Methanocalculus, Methanobrevibacter* and *Methanosarcina*, or the one or more methanogenic organisms comprise one or more members selected from the group consisting of:

*Methanolobus bornbayensis*
*Methanolobus taylorii*
*Methanolobus profundi*
*Methanolobus zinderi*
*Methanobacterium bryantii*
*Methanobacterium formicum*
*Methanobrevibacter arboriphilicus*
*Methanobrevibacter gottschalkii*
*Methanobrevibacter ruminantium*
*Methanobrevibacter smithii*
*Methanocalculus chunghsingensis*
*Methanococcoides burtonii*
*Methanococcus aeolicus*
*Methanococcus deltae*
*Methanococcus jannaschii*
*Methanococcus maripaludis*
*Methanococcus vannielii*
*Methanocorpusculum labreanum*
*Methanoculleus bourgensis (Methanogenium olentangyi & Methanogenium bourgense)*
*Methanoculleus marisnigri*
*Methanofollis liminatans*
*Methanogenium cariaci*
*Methanogenium frigidum*
*Methanogenium organophilum*
*Methanogenium wolfei*
*Methanomicrobium mobile*
*Methanopyrus kandleri*
*Methanoregula boonei*
*Methanosaeta concilii*
*Methanosaeta thermophila*
*Methanosarcina acetivorans*
*Methanosarcina barkeri*
*Methanosarcina mazei*
*Methanosphaera stadtmanae*
*Methanospirillium hungatei*
*Methanothermobacter defluvii (Methanobacterium defluvii)*
*Methanothermobacter thermautotrophicus (Methanobacterium thermoautotrophicum)*
*Methanothermobacter thermoflexus (Methanobacterium thermoflexum)*
*Methanothermobacter wolfei (Methanobacterium wolfei)*, and
*Methanothrix sochngenii*

In alternative embodiments, the invention provides methods comprising an integrated process for optimizing biogas generation from subsurface organic matter-rich formations (coal and/or other organic-containing rocks), comprising one or more, or all, the following steps:

(a) a microbial collection procedure conducive to acquiring both deep microbial community surveys (DNA/RNA analyses) and cultured isolates of key living microorganisms;

(b) identification of specific target microbial associations capable of rapidly transforming organic matter to biogas, using empirical correlation of the microbial profiling data (e.g., from 454-pyrosequencing) to key geochemical parameters using an integrated multi-disciplinary data-set;

(c) simultaneous identification of unfavorable endemic microbes or conditions showing negative correlation to biogas formation, as identified in 6b above;

(d) use of microbial evaluation tools, to further identify the specific active microbes critical to biogas growth (or inhibition) out of the empirically identified microbial targets;

(e) rock characterization of both indigenous organic carbon-rich substrates and inorganic mineralogy affecting the water-injectate recipe composition for enhanced biogas formation and selection of substrate rocks;

(f) further optimization of the proposed injectate-water chemistry from a matrix of laboratory enrichment experiments to promote subsurface biogas production without activating deleterious microbial effects at the reservoir temperature of the target field) and subsequent flow-through core experiments using the water-injectate recipe on targeted rock cores;

(g) geochemical modeling of the solution stability to account for undesired precipitation of minerals due to interactions between in-situ formation water, the injectate and in-situ mineral phases;

(h) modeling fluid transport within the reservoir structure and delivery mechanisms to successfully spread the water-soluble amendments and cultured microbes to the target formations;

(i) modeling of transport of the newly generated microbial methane within the reservoir towards the gas column and the producing wells;

(j) field implementation of the biogas production process; and/or (k) field monitoring of biogas production and collateral microbial/water changes.

In alternative embodiments, the invention provides methods of transforming a carbonaceous substrate, a carbonaceous material or a carbon source into a lower molecular weight (MW) compound using a synthetic microbial consortia comprising the steps of:

a. Providing a plurality of samples that comprise a carbonaceous substrate and microbial communities;
b. Determining the composition of the microbial community in each sample;
c. Identifying a consortium (a grouping) of microbes whose abundance correlates with transformation of the carbonaceous substrate;
d. Assembling a synthetic consortium by combining individual pure cultures in a strain collection;

e. Combining the synthetic consortium with a carbonaceous substrate to convert it to a higher value and lower molecular weight product;

and optionally the samples are enrichment cultures incubated with the carbonaceous substrate.

In alternative embodiments of the method, the carbonaceous substrate, carbonaceous material or carbon source comprises or further comprises a coal, a bituminous coal, an anthracite coal, a volcanic ash, or a lignite or a lignin or lignin-comprising composition, a coal or a coal analogues or a precursors thereof, heavy oil, asphaltenes, and/or an organic debris.

In alternative embodiments, the invention provides methods for increasing or stimulating a coal to methane conversion rate, comprising:

(a) injecting: at least one synthetic consortium of the invention, and/or one or more methanogenic organisms, into an isolated (e.g., out of ground, mined or excavated) or a subsurface carbonaceous or coal reservoir or a source comprising a coal, a bitumen, a tar-sand or an equivalent, or (b) contacting the isolated or subsurface carbonaceous or coal reservoir, or coal, bitumen, a tar-sand, or equivalent, with: at least one synthetic consortium of the invention, or a composition comprising one or more methanogenic organisms, wherein optionally the contacting is in situ (e.g., in a ground formation or a subsurface carbonaceous reservoir), or a man-made reservoir or product of manufacture, wherein the one or more methanogenic organisms comprise one or more members of the Archaea family, or are anaerobic organisms, or are autotrophs or chemoheterotrophs, wherein optionally the subsurface carbonaceous reservoir comprises a coal formation, or a peat, or a lignite, or a bituminous coal, or an anthracite coal.

In alternative embodiments, wherein the one or more methanogenic organisms comprise one or more members of a genus selected from the group consisting of *Methanolobus, Methanobacterium, Methanothermobacter, Methanogenium, Methanogenium, Methanofollis, Methanoculleus, Methanocorpusculum, Methanococcus, Methanocalculus, Methanobrevibacter* and *Methanosarcina*, or the one or more methanogenic organisms comprise one or more members selected from the group consisting of:

*Methanolobus bornbayensis*
*Methanolobus taylorii*
*Methanolobus profundi*
*Methanolobus zinderi*
*Methanobacterium bryantii*
*Methanobacterium formicum*
*Methanobrevibacter arboriphilicus*
*Methanobrevibacter gottschalkii*
*Methanobrevibacter ruminantium*
*Methanobrevibacter smithii*
*Methanocalculus chunghsingensis*
*Methanococcoides burtonii*
*Methanococcus aeolicus*
*Methanococcus deltae*
*Methanococcus jannaschii*
*Methanococcus maripaludis*
*Methanococcus vannielii*
*Methanocorpusculum labreanum*
*Methanoculleus bourgensis* (*Methanogenium olentangyi* & *Methanogenium bourgense*)
*Methanoculleus marisnigri*
*Methanofollis liminatans*
*Methanogenium cariaci*
*Methanogenium frigidum*
*Methanogenium organophilum*
*Methanogenium wolfei*
*Methanomicrobium mobile*
*Methanopyrus kandleri*
*Methanoregula boonei*
*Methanosaeta concilii*
*Methanosaeta thermophila*
*Methanosarcina acetivorans*
*Methanosarcina barkeri*
*Methanosarcina mazei*
*Methanosphaera stadtmanae*
*Methanospirillium hungatei*
*Methanothermobacter defluvii* (*Methanobacterium defluvii*)
*Methanothermobacter thermautotrophicus* (*Methanobacterium thermoautotrophicum*)
*Methanothermobacter thermoflexus* (*Methanobacterium thermoflexum*)
*Methanothermobacter wolfei* (*Methanobacterium wolfei*), and
*Methanothrix sochngenii*

The details of one or more embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

Nevertheless, it will be understood that various modifications may be made without departing from the spirit and scope of the invention. Other features, objects and advantages of the invention will be apparent from the description and drawings, and from the claims.

BRIEF DESCRIPTION OF THE DRAWINGS

The drawings set forth herein are illustrative of embodiments of the invention and are not meant to limit the scope of the invention as encompassed by the claims. Reference will now be made in detail to various exemplary embodiments of the invention, examples of which are illustrated in the accompanying drawings. The following detailed description is provided to give the reader a better understanding of certain details of aspects and embodiments of the invention, and should not be interpreted as a limitation on the scope of the invention. A more complete understanding of the present invention and benefits thereof may be acquired by referring to the follow description taken in conjunction with the accompanying drawings in which:

FIG. 9(a) addition of microbial consortium from the same well and grown on coal/lignin/lignin monomers mixture (well 40-3 had the highest rate, see FIG. 3, hence this consortium was used as inoculum) enhances the methanogenesis rate over tubes with optimized chemical recipe only, but no cell additions; FIG. 9(b) addition of coal/lignin/lignin monomers mixture-grown consortium to formation water from well that originally had very low methane production (FIG. 3). Note that adding coal/lignin/lignin monomers-grown consortia to production water from different basin (California) also successfully increases methane production from the same rock material. Each data point represents a triplicate set of sand pack tubes.

FIG. 12A is a representation of well injection system including existing injection water systems, concentrated nutrient storage tank, nutrient mixing tank, and injection line for injecting dilute nutrient mixture. FIG. 12B is one example of a Batch Mixing tank A and Storage tank B for storage and mixing of concentrated nutrient solutions up to 250 bbls per batch.

FIG. 14A, Level of biomass before treatment with 0.6% NaOCl solution at various oxygen levels and nutrient conditions; FIG. 14B, Level of biomass immediately after treatment with 0.6% NaOCl solution at various oxygen levels and nutrient conditions. CFU/mL=Colony-forming units per milliliter.

FIG. 15A. Biomass level over time in cultures incubated at 10° C. and 20° C. in 25× excess concentration nutrient recipe; FIG. 15B, Biomass level in cultures incubated at 25° C. in standard (1×) concentration of recipe. CFU/mL=Colony-forming units per milliliter.

DETAILED DESCRIPTION

Figure 1:
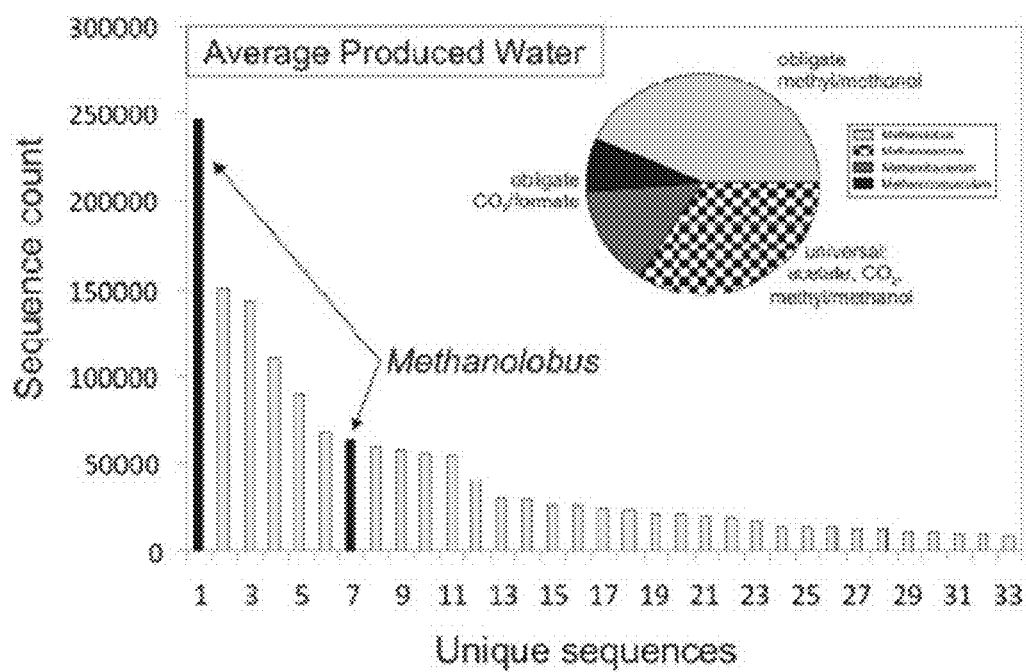
FIG. 1 graphically illustrates the Rank abundance plot of 16S rRNA gene sequences isolated from production water of gas wells from the Cook Inlet, Ak. DNA sequences belonging to the genus *Methanolobus* are shown as highlighted bars. The relative proportions of methanogens that utilize one or more of the three methanogenic pathways are indicated (inset).

Turning now to the detailed description of the arrangement or arrangements of the one or more embodiments of the invention, it should be understood that the inventive features and concepts may be manifested in other arrangements and that the scope of the invention is not limited to the embodiments described or illustrated. The scope of the invention is intended only to be limited by the scope of the claims that follow.

The invention provides compositions and methods for commercial biogas, e.g., methane, production. In alternative embodiments, the invention provides compositions and methods for methanol-utilizing methanogenesis, or "methylotrophic"-conversion, including utilizing methylamines and other methyl-containing intermediates.

The inventors have successfully demonstrated faster, commercial biogas (e.g., methane) production rates under highly favorable laboratory conditions by enhancing the microbial environment, e.g., by varying pH, microbe and nutrient supplementation of water. The inventors have demonstrated that biogenic gas fields in the Cook Inlet (Alaska) have a surprisingly significant contribution from a third, equally important and often disregarded pathway—methanol-utilizing methanogenesis, or "methylotrophic"-conversion, which also can include substrates such as methylamines and other methyl-containing intermediates. In alternative embodiments the invention provides compositions and methods comprising use of methanol-utilizing methanogenesis, which also can include use of substrates such as methyl amines and other methyl-containing intermediates.

In alternative embodiments the invention provides an integrated process for optimization of biogas (e.g., methane) generation in subsurface organic matter-rich formations (e.g., man made formations, such as landfills, or natural formations such as coal formations, shale, sandstone or limestone with organic debris or oil) via the methylotrophic pathway.

In alternative embodiments the ultimate goal of this biogas application is to extend the productive field-life of sub-surface biogenic-gas assets. In alternative embodiments, field implementation of biogas production is based on an integrated microbial-substrate characterization, including all or some of the following steps: (1) a microbial collection procedure conducive to both deep microbial community surveys (DNA/RNA analyses), culturing and isolation of living microorganisms; (2) identification of specific target microbial associations capable of rapid transformation of subsurface organic matter to biogas via e.g. the methylotrophic pathway, using empirical correlation of microbial profiling (in alternative embodiments using pyrosequencing) data to key geochemical parameters and targeted incubations (e.g. with lignin or other coal-analogues or precursors); (3) simultaneous identification of unfavorable endemic microbes or conditions showing negative correlation to biogas formation using the same information as in step #2; (4) formation characterization of both indigenous organic carbon-rich substrates and inorganic mineralogy affecting the water-injectate composition for biogas formation (including core-water-microbe experiments); (5) optimization of an injectate water chemistry (especially water pH and essential nutrients) and microbiology (selected isolates or pre-grown successful communities obtaining high methanogenesis rates with targeted coal and coal analogues) to promote subsurface biogas production at the reservoir temperature of the target field); (6) investigation and modeling of delivery mechanisms to successfully spread the water-soluble amendments and cultured microbes to the target formations; and (7) field implementation of any one or all of these steps in e.g., a biogas production process.

In alternative embodiments, the compositions and methods of the invention identify, mimic and/or manipulate the combination of parameters that result in the specificity of a methanogenic pathway in the subsurface, including e.g., any one or a combination of parameters, for example: i) type of organic matter (e.g., plant versus (vs) algae derived), ii) thermal maturity of organic matter (e.g., level of aromaticity and hence recalcitrance), iii) formation water chemistry (e.g., salinity, pH, inorganic and organic water chemistry), iv) temperature, and v) presence of appropriate syntrophic bacterial community able to provide specific methanogenic substrates.

In alternative embodiments, the invention provides compositions, e.g., nutrient mixes, and methods of enhancing biogenic methane production through the creation of customized nutrient amendments (e.g., supplements, mixes and the like), wherein the compositions and methods can be used to specifically stimulate (or inhibit, as appropriate) functionally important constituents of a microbial community responsible for biogas formation (or responsible for inhibition of optimal biogas production). In alternative embodiments, the invention provides microbial compositions (including bioreactors, which include subsurface reservoirs) to augment microorganisms involved in the methanogenic degradation of recalcitrant organic matter or to introduce new microbial functionalities into a reservoir to initiate or stimulate this process.

In alternative embodiments, the invention can identify a microbial community present in a subsurface carbonaceous reservoir, e.g., by nucleic acid (e.g., DNA, RNA) characterization, e.g., by nucleic acid sequencing, hybridization, PCR and the like, to determine or characterize the microbes present (optionally including their relative abundance); and in alternative embodiments a customized nutrient mixture of the invention comprises, or is based on: (1) published nutrient requirement values that are weighted toward the more abundant and important (relative to the targeted methanogenic pathway) organisms; and (2), field observations about specific reservoir conditions (e.g. water chemistry, well production, etc.). In alternative embodiments, the resulting customized nutrient composition of the invention is introduced to a reservoir through an injection process at the well head, or is used in a bioreactor of the invention. In alternative embodiments, a bioreactor of the invention includes any subsurface space or reservoir, such as a man-made subsurface reservoir.

Organisms that participate in a given biogeochemical process or pathway make up consortia and might be expected to be coordinately distributed in the environment. In other words, the members of a given consortium will tend to be found together. The degree to which these microbes are found together is expected to be a function of the obligate nature of their metabolic relationship. For example, two syntrophic organisms that only utilize a single carbon substrate and that were absolutely dependent upon each other to metabolize the substrate would display the strongest coordinated distribution since neither partner could exist or proliferate without the other (e.g., sulfate reducing bacteria with anaerobic methane oxidizers or potentially a methanol producing bacterium with obligate methylotrophic methanogen such as *Methanolobus*). In other cases where two syntrophic organisms had similar dependencies upon one another for a given substrate, but had additional substrates that they could utilize independently of the syntrophic partner, would display a much less tightly linked environmental distribution. The organisms of this latter example are expected to have a coordinated distribution among environments where syntrophy was necessary for metabolism of the prevailing substrates. An example of this situation is in subsurface accumulations of coal.

This tendency of members of a given consortium to be found together is an attribute that can be used to identify microbes that work together in a given biodegradative process such as the conversion of coal into methane (Ashby 2003). By identifying the key microbial players that perform a process of interest in a particular environment, they can be specifically re-introduced into an environment to enhance the rate and specificity of said process.

In alternative embodiments, a consortium is a group of two or more (a plurality of) microorganisms that participate in a common ecological or biosynthetic or biodegradative process, e.g., a biogeochemical process. During biogenic gas formation, microbes can participate in the same biogeochemical process or metabolic pathway. Oftentimes, these microbes are able to perform distinct steps of the same metabolic, biochemical or biodegradative pathway. In some embodiments, the term "consortium" defines a group of (a plurality of) microorganisms that participate in the same biogeochemical cycle, such as the conversion of a coal to a methane, or biodegradation of a heavy oil; and in alternative embodiment consortiums of the invention are used to convert a coal, or a coal analogue(s) or a precursor(s) and the like to a methane, or biodegrade an oil or a heavy oil and the like. In other embodiments, the term "consortium" is defined as a group of microorganisms that participate in a unified set of biochemical reactions, such as in biogeochemical cycles.

In alternative embodiments, species describes a taxonomic rank of an organism. In alternative embodiments species are classified based on traits such as similarity of DNA, morphology or ecological niche. In alternative embodiments species are grouped using statistical analysis of DNA sequences or markers to determine the relatedness of two or more bacterial or Archaeal microorganisms. In one embodiment, two or more organisms are classified as members of the same species when an alignment of the 16S rRNA gene sequences reveals about 5% or less difference (95% identity) at the nucleotide level, about 4% or less difference (96% identity) at the nucleotide level, about 3% or less difference (97% identity) at the nucleotide level, about 2% or less difference (98% identity) at the nucleotide level, or about 1% or less difference (99% identity) at the nucleotide level.

In alternative embodiments, synthetic consortium are a set of microbes where each one exists in pure culture and are combined to form a defined mixture or consortium of microbes that can perform a particular, useful function. In one embodiment, a synthetic consortium comprises two or more cultured species available from commercial and/or unique isolated cultures where the cultured species are selected to perform complementary processes in a geochemical or biogenic gas pathway. In one embodiment, a synthetic consortium of microbes comprises two or more uncultured species that are combined by physical means where the cultured species are selected to perform complementary processes in a geochemical or biogenic gas pathway.

In alternative embodiments, syntrophs are organisms that utilize products from another organism. In one embodiment, two or more microbes may be dependent upon each other to perform a biochemical reaction, generate an essential product, or produce a substrate or cofactor.

In alternative embodiments, biochemical and geochemical compositions undergo one or more chemical transformations. In one embodiment, a substrate is transformed when it undergoes a biochemical reaction through the action of enzymes produced by biological organisms, for example, by practicing a method of this invention. In another embodiment, the transformation involves one or more catabolic reactions where the result of the process or pathway is reduction in the molecular weight of the substrate.

In alternative embodiments, upgrading heavy oil as used herein describes the process of lowering the boiling point of a composition that may include heavy crude oil, bitumen, tars, and other high viscosity hydrocarbons. The viscosity of crude oil or tar usually by reducing the molecular weight of its constituents, increasing aromatic components, removing volatile fatty acids, increasing the gas to oil (GOR) ratio, addition of solvents, increasing the hydrogen content, and other processes where viscosity is decreased. In one embodiment the viscosity of the heavy oil is decreased by converting high molecular weight hydrocarbons into lower molecular weight hydrocarbons. In another embodiment, heavy oils, bitumens, tarsands and the like are converted to less viscous or gaseous light gas, gas and diesel range products from C1-C24 hydrocarbons.

Identifying Relevant Consortium and its Members

In one embodiment, the composition of microbial communities is determined or profiled from samples that have been in contact with coal or other carbonaceous material of interest. These samples will include environmental samples such as production water, formation water, core samples, drill cuttings, water, sediment or soil. Optimally, the samples would contain the same carbonaceous material that was the subject of investigation to find microbes capable of transforming into a higher value product. For example, samples would be chosen that contained coal that had a similar level of maturity as that in the target basin.

In another embodiment, the microbial communities present in these samples are used to inoculate cultures comprising a carbon source, essential nutrients (including vitamins, trace metals and a source of phosphorus, sulfur and nitrogen), and optionally including a buffer to maintain pH, a reducing agent (sodium sulfide, sodium dithionite, dithiothreitol, thioglycollate or cysteine), a redox indicator (e.g. resazurin or methylene blue) and a terminal electron acceptor (e.g. oxygen, nitrate, sulfate, Fe(III), Mn(IV), carbon dioxide, or anthraquinone disulfonate (AQDS)). Anaerobic culture conditions, enrichment methods and medium formulations are widely known to those skilled in the art and may be practiced in a variety of ways such as those described by Shelton and Tiedje (Shelton and Tiedje 1984). The carbon source for the enrichments would be of the same type such as coal or asphaltenes as described above.

In an alternative embodiment, the enrichment cultures are maintained in serum vials. At various time points in their incubation, the enrichment cultures would be tested for growth and metabolism. Cell growth is assayed by microscopic cell counts or by measuring optical density at 550 or 600 nm wavelength in a spectrophotometer. Metabolism is measured by gas production where the volume of gas produced is determined with a pressure transducer (Shelton and Tiedje 1984) and the type of gas (e.g. CH4, H2, or CO2) is determined by gas chromatography. The transfer of electrons to AQDS and the resulting color change from clear to orange, can also be used as a measure of metabolic activity. Additionally, consumption of the carbonaceous substrate can indicate metabolic activity.

In yet another embodiment, DNA is extracted from the enrichment cultures to characterize the microbial community at the beginning of incubation and after growth and/or metabolism is detected. This community analysis can be done repeatedly to characterize community changes during the period of incubation and can be tracked together with the geochemical changes of the medium and gaseous headspace. After the enrichment cultures exhaust nutrients as evidenced by a reduction in growth rate or metabolic activity, the cultures are optionally passaged into fresh medium using a dilution factor such as 1 ml of original culture diluted into 100 mls of fresh medium. The methods described above to determine growth and metabolism are repeated for subsequent passages. This exercise of repeated growth and transfer to fresh medium can also be performed in bioreactors, fermenters or chemostats and will have the effect of diluting away (washing out') members of the community that are not involved in metabolizing the target substrate. At the same time consortium members that are involved in metabolizing the substrate will become established if they are able to increase their cell numbers to offset their dilution during culture passaging or through the outflow of medium in a chemostat.

An exemplary method of the invention for determining the microbial community composition can comprise any of the methods known to those skilled in the art; such as, e.g., DNA sequencing of all or a portion of 16S rRNA genes, by hybridization of sample derived DNA to immobilized oligonucleotides or PCR generated probes (i.e. DNA microarrays), quantitative PCR (qPCR) analysis, separation of DNA fragments such as terminal restriction fragment length polymorphism (T-RFLP) analysis or by non-DNA-based methods such as fatty acid methyl ester (FAME) analysis. For DNA-based profiling methods, genomic DNA is isolated by any of a number of methods or commercially available kits that would result in the efficient recovery of DNA with a minimal level of introduced bias. For DNA sequence profiling of 16S rRNA genes, 'universal' primers can be utilized to PCR amplify a portion of the gene that includes variable regions. Limiting the number of PCR cycles can reduce biases and artifacts that might occur.

In one embodiment, the microbial community composition profile data determined through the use of culture independent, molecular surveys described above, optionally in the form of number of copies of each distinct 16S rRNA gene sequence detected from each sample, is then analyzed to detect the distribution patterns of microbes amongst the samples tested. As indicated above, microbes that participate in the same biodegradative or metabolic pathway and thus, members of a common microbial consortium will tend to be found together in the environment (including samples derived therefrom). This relationship can also be deduced from abundance data in culture independent surveys (Ashby 2003).

In one embodiment, to identify potential relationships that exist between environmental microbes as indicated by their tendency to be coordinately distributed in the environment, the data is first log transformed. Log transformation tends to make microbial distribution data more normally distributed which may result from the logarithmic nature of microbial growth. Log transformed microbial distribution data can then be compared between different 16S rRNA gene sequence detected using correlation analysis (e.g. Pearson). Operationally, a distance matrix is constructed where the distribution of every sequence is correlated with that of every other sequence. The results can then be graphically represented using hierarchical clustering algorithms such as Ward's method. Computer software programs are widely available to perform this analysis such as PC-ORD (Gleneden Beach, Oreg.). This exercise will reveal groups of sequences that tend to be found together (see example below). Comparison of the distribution of the group as a whole to the transformation or metabolic activity observed in the samples (or enrichment cultures) will provide further evidence as to the metabolic functional capability of the consortium.

In alternative embodiments, the members of a consortium are identified from microbial community surveys using distance metrics that include Euclidean distance, Chi square, city block, and ordination methods that include PCA, Bray-Curtis, and nonmetric multidimensional scaling (NMS or NMDS).

Utilizing Consortium to Enhance Transformation Rate of a Carbonaceous Substrate

In alternative embodiments, consortium of microbes to be utilized to enhance methanogenesis rates can be prepared by multiple strategies. One approach involves systematically isolating in pure culture all of the members of the consortium of interest. The individual consortium members are then combined into a synthetic consortium which can then be tested for metabolism of the substrate of interest and/or utilized for the commercial scale conversion of a carbonaceous substrate into a higher value-lower molecular weight product.

In alternative embodiments, methods and medium formulations for isolating environmental microbes in pure form comprise those known in the art. In alternative embodiments, for consortia that would ultimately be deployed in the subsurface where oxygen is absent, anaerobic cultivation methods are used. Samples or enrichment cultures that possess the microbes of interest are diluted and plated onto a variety of solid medium containing different nutrient combinations to obtain single colonies. At least one of the medium formulations should contain the carbonaceous substrate of interest. Parameters such as salt concentration and pH should be as consistent as possible with the original sample where the organisms of interest were present or adjusted to optimize growth of targeted microbes and enhancement of targeted metabolic process. Oftentimes environmental microbes are difficult, if not impossible, to cultivate and their isolation requires the use of alternative strategies such as dilute nutrients and different medium solidifying agents (e.g., see Connon and Giovannoni 2002; Sait, Hugenholtz et al. 2002).

In alternative embodiments, microbial colonies that appear on plates following incubation should be picked and re-streaked onto fresh medium at a low enough density to obtain new, well resolved colonies. This colony purification procedure can be repeated to reduce the risk of colonies being comprised of multiple species. The resulting colonies should display a uniform morphology consistent with a homogenous population of organisms. In alternative embodiments, a colony is picked and grown up either in liquid culture or as a patch on the same medium type. The resulting culture is then frozen at −80° C. and/or freeze dried for archival purposes. DNA from the cells from the same culture is extracted for identification by sequencing its 16S rRNA gene.

In alternative embodiments, a second approach is to utilize enrichment cultures as described above to select for a consortium with the properties of interest while at the same time selecting against microbes that do not participate in the process. This approach is utilized when some members of the consortium of interest cannot be cultivated in pure form. Organisms that are expected to fall into this category include obligate syntrophs which by definition cannot be grown in pure culture in the absence of their syntrophic partner. While this approach is not as preferable as the pure culture route that can produce a community of exactly the members desired, it can lead to a highly enriched culture for the organisms with the metabolic potential of interest. Such successful culture might be further tested to identify tightly bound syntrophic associations. Subsequent cultivation may allow isolation of these tight associations, their phylogenetic confirmation by DNA extraction, and their storage for further lab and commercial use.

In alternative embodiments, additional methods of assembling a synthetic consortium of the invention involve physically separating cells present in a sample using methods such as fluorescence activated cell sorting (FACS). The cells of interest can be specifically labeled with fluorescent labeled probes and fluorescent in situ hybridization (FISH) without using fixatives. Other methods to physically separate cells of interest include optical tweezers or through the use of antibodies that specifically recognize determinants on the cell of interests surface.

In alternative embodiments, synthetic consortium of the invention comprise a mixture of cells each derived from pure isolates or a highly enriched consortium, which optionally can be derived from a selective growth, and then optionally can then be introduced into a subsurface reservoir or other environment containing the carbonaceous substrate of interest, where optionally the consortium has been selected for growth and metabolic performance under the specific environmental conditions with the goal to convert the substrate to a higher value product.

One embodiment provides methods for increasing commercial biogas production in a sub-surface environment. In another embodiment the invention provides an integrated process for optimization of biogas generation including methane in subsurface organic matter-rich formations including man made formations, such as landfills, surface or subsurface bioreactors (in alternative embodiments, a bioreactor of the invention or a bioreactor used to practice the invention includes any subsurface space or reservoir, such as a man-made subsurface reservoir) and the like, or natural formations such as shale, coal, oil sands, bitumen, tar, oil, sandstone and limestone with organic debris or other hydrocarbon rich formations via the methylotrophic pathway. Methods for analysis and understanding of subsurface microbial communities responsible for conversion of coal and coal-like substrates into methane, and for controlling geochemical conditions are provided. Thus, in alternative embodiments, compositions and methods to stimulate subsurface methanogenesis pathways and to enhance the rates of biogas formation are provided.

In alternative embodiments, methods of the invention for increasing biogas production extend the productive field-life of sub-surface biogenic-gas assets. In alternative embodiments, field implementation of biogas production is based on an integrated microbial-substrate characterization, including all or some of the following steps: (1) a microbial collection procedure conducive to both deep microbial community surveys (DNA/RNA analyses), culturing and isolation of living microorganisms; (2) identification of specific target microbial associations capable of rapid transformation of subsurface organic matter to biogas via e.g. the methylotrophic pathway, using empirical correlation of microbial profiling (in alternative embodiments using pyrosequencing) data to key geochemical parameters and targeted incubations (e.g. with lignin or other coal-analogues or precursors); (3) simultaneous identification of unfavorable endemic microbes or conditions showing negative correlation to biogas formation using the same information as in step #2; (4) formation characterization of both indigenous organic carbon-rich substrates and inorganic mineralogy affecting the injectate-water composition for biogas formation (including core-water-microbe experiments); (5) optimization of an injectate water chemistry (especially water pH and essential nutrients) and microbiology (selected isolates or pre-grown successful communities obtaining high methanogenesis rates with targeted coal and coal analogues) to promote subsurface biogas production at the reservoir temperature of the target field); (6) investigation and modeling of delivery mechanisms to successfully spread the water-soluble amendments and cultured microbes to the target formations; and (7) field implementation of any one or all of these steps in e.g., a biogas production process. In other embodiments the invention may include, evaluation of the potential for biomass formation and scale precipitation associated with adding amendments and cultured microbes to existing field conditions; simulation of biogas in a subsurface reservoir using a computational model; monitoring injected fluids, biogas, and changes in the microbial community; or field implementation of any one or all of these steps in e.g., a biogas production process.

In alternative embodiments, the compositions and methods of the invention identify, mimic and/or manipulate a combination of parameters that result in the specificity of a methanogenic pathway in the sub-surface, including e.g., any one or a combination of parameters, for example: i) type of organic matter (e.g. plant vs algae derived), ii) thermal maturity of organic matter (level of aromaticity and hence recalcitrance), iii) formation water chemistry (i.e. salinity, pH, inorganic and organic water chemistry), iv) temperature, and v) presence of appropriate syntrophic bacterial community able to provide specific methanogenic substrates.

In alternative embodiments, the invention provides compositions, e.g., nutrient mixes, and methods of enhancing biogenic methane production through the creation of customized nutrient amendments (e.g., supplements, mixes and the like), wherein the compositions and methods can be used to specifically stimulate (or inhibit, as appropriate) functionally important constituents of a microbial community responsible for biogas formation (or responsible for inhibition of optimal biogas production). In alternative embodiments, the invention provides microbial compositions (including bioreactors) to augment microorganisms involved in the methanogenic degradation of recalcitrant organic matter or to introduce new microbial functionalities into a reservoir to initiate or stimulate this process.

In alternative embodiments, the invention can identify a microbial community present in a subsurface carbonaceous reservoir, e.g., by nucleic acid (e.g., DNA, RNA) characterization, e.g., by sequencing, hybridization, PCR and the like, to determine or characterize the microbes present (optionally including their relative abundance); and in alternative embodiments a customized nutrient mixture provided comprises, or is based on: (1) published nutrient requirement values that are weighted toward the more abundant and important (relative to the targeted methanogenic pathway) organisms; and (2), field observations about specific reservoir conditions (e.g. water chemistry, well production, etc.). In alternative embodiments, the resulting customized nutrient composition of the invention is introduced to a reservoir through an injection process at the well head, or is used in a bioreactor of the invention.

In alternative embodiments, the resulting customized nutrient composition is used in a bioreactor, optimized through a bioreactor-nutrient optimization test, and/or introduced to a reservoir through an injection process at the well head as required to optimize biogas production in the bioreactor and/or in the hydrocarbon formation.

In another embodiment, the invention characterizes, e.g., by sequencing, hybridization, PCR and the like, microbial communities present in a subsurface carbonaceous reservoir. In one embodiment, a customized nutrient mixture is determined based on published nutrient requirement values alone that is weighted toward the more abundant and important organisms. The resulting customized nutrient composition used in a bioreactor, optimized through a bioreactor-nutrient optimization test, and/or introduced to a reservoir through an injection process at the well head as required to optimize biogas production in a bioreactor and/or in a hydrocarbon formation.

In alternative embodiments, the invention characterizes, e.g., by nucleic acid sequencing, hybridization, PCR and the like, microbial communities present in a subsurface carbonaceous reservoir. The resulting customized nutrient mixture of the invention can be determined based on published nutrient requirement values.

In another embodiment, nutrient formulations that were developed for one reservoir are utilized for another reservoir with similar properties such as geological history, geochemistry, source of carbon and microbial community composition.

In alternative embodiments, the rate of methanogenesis in a subsurface reservoir harboring coal and other recalcitrant organic carbon sources is increased by introduction of one or more members of a genus selected from the group consisting of *Methanolobus*, *Methanobacterium*, *Methanothermobacter*, *Methanogenium*, *Methanogenium*, *Methanofollis*, *Methanoculleus*, *Methanocorpusculum*, *Methanococcus*, *Methanocalculus*, *Methanobrevibacter* and *Methanosarcina* (as pure or nearly pure culture, e.g., greater than about 70%, 80%, 90%, or 95% of cells, are from one particular genus) through injection at the well head. The cells may be provided as cultures, cell pellets (such as obtained through centrifugation or filtration), or lyophilized preparations that are reconstituted.

In alternative embodiments, *Methanolobus*, *Methanobacterium*, *Methanothermobacter*, *Methanogenium*, *Methanogenium*, *Methanofollis*, *Methanoculleus*, *Methanocorpusculum*, *Methanococcus*, *Methanocalculus*, *Methanobrevibacter* and/or *Methanosarcina* cells (e.g., as pure, substantially pure, or nearly pure culture, e.g., greater than about 50%, 60%, 70%, 75%, 80%, 85%, 90%, or 95% or more of cells in culture) (e.g., in a nutrient mix, a fluid, or composition, e.g., a mud) are introduced into a subsurface reservoir or deposit, or isolated, mined or excavated source, e.g., that has (comprises) gas, coal, oil, heavy oil, tar-sand, bitumen and the like.

In alternative embodiments, *Methanolobus*, *Methanobacterium*, *Methanothermobacter*, *Methanogenium*, *Methanogenium*, *Methanofollis*, *Methanoculleus*, *Methanocorpusculum*, *Methanococcus*, *Methanocalculus*, *Methanobrevibacter* and/or *Methanosarcina* cells (optionally e.g., as pure, substantially pure, or nearly pure culture, e.g., greater than about 50%, 60%, 70%, 75%, 80%, 85%, 90%, or 95% or more of cells in culture) are delivered to the subsurface reservoir or deposit, or isolated, mined or excavated source, through injection as enrichment cultures, where optionally they comprise a substantial or significant portion of the total number of cells, e.g., equivalent to at least about 1%, 5%, 10%, 15%, 20%, 25%, 30% or 35% or more by cell number.

In alternative embodiments, *Methanolobus*, *Methanobacterium*, *Methanothermobacter*, *Methanogenium*, *Methanogenium*, *Methanofollis*, *Methanoculleus*, *Methanocorpusculum*, *Methanococcus*, *Methanocalculus*, *Methanobrevibacter* and/or *Methanosarcina* cells (e.g., as pure, substantially pure, or nearly pure culture, e.g., greater than about 50%, 60%, 70%, 75%, 80%, 85%, 90%, or 95% or more of cells in culture) are used in a bioreactor, fluid, composition or product of manufacture of the invention.

In alternative embodiments, the invention also provides methods to enrich or select for endemic organisms capable of converting a carbonaceous material of interest that can then be re-injected into a formation to enhance methanogenesis rates, or inhibit or decrease endemic organisms that inhibit or decrease biogas formation. In one embodiment, this process of the invention is useful because it selects for the most important organisms required for the entire degradative methanogenic pathway from a pool of organisms that are already selected (e.g., through natural selection) for growth under reservoir conditions. These methods also can be used to enrich an environment of a bioreactor of the invention.

In alternative embodiments, cells present in production water are used to inoculate enrichment cultures containing defined medium (mineral salts, trace metals, vitamins), where the only carbon source (above trace levels) is provided as the reservoir carbonaceous material and/or chemical analogues thereof. Growth of the cultures is monitored by measuring changes in headspace pressure (e.g., as described by Shelton and Tiedje 1984) and methane production (e.g. using GC/FID as described by Strapoc et al., 2008) and in increased numbers of cells present that results in increased turbidity. Once a significant amount of growth is detected, the culture is passaged into fresh medium (e.g., about 1 to 100-fold dilution). This procedure can be repeated indefinitely. These procedures are well known to those skilled in the art and are described in detail in general microbiology textbooks (e.g. Manual of Environmental Microbiology, 3rd edn. Hurst, C. J., Crawford, R. L., Garland, J. L., Lipson, D. A., Mills, A. L., and Stetzenbach, L. D. Washington, D.C., USA: ASM Press, pp. 1063-1071.). Prior to injection into the reservoir the culture can be passaged into a large capacity fermenter to produce large number of cells. These methods also can be used to produce a bioreactor of the invention.

In alternative embodiments, cells present in production water are used to inoculate enrichment cultures containing defined medium (mineral salts, trace metals, vitamins), produced water, or nutrient-amended produced water, where the only carbon source provided is a chemical analogue or multiple analogues of the reservoir carbonaceous material. In this embodiment, use of tested chemical analogues allows faster biomass growth, e.g. prior injection into the reservoir, of the cultures than in cultures using only the reservoir carbonaceous material. In yet another embodiment, cells present in production water are used to inoculate enrichment cultures containing defined medium supplemented with a customized nutrient mix where the only carbon source (above trace levels) is provided as the reservoir carbonaceous material. The cells can be inoculated into enrichment cultures of a bioreactor of the invention.

In alternative embodiments, cells isolated from or microbial consortia found in other formations, basins or environments are used to inoculate enrichment cultures containing defined medium or target produced water supplemented with a customized nutrient mix where the only carbon source (above trace levels) is provided as the target reservoir carbonaceous material or analogue of thereof or carbonaceous material from other reservoir or basin. The cells can be inoculated into enrichment cultures of a bioreactor of the invention or the target reservoir or other reservoir or basin.

In alternative embodiments, the cells produced from the aforementioned enrichments or fermenter are lyophilized for storage and transport to the well site where they are mixed with water and customized nutrient formulations immediately prior to injection. The cells would be lyophilized in the presence of reducing agents to protect the methanogens and other obligate anaerobes from oxidation during storage and injection. These cells also can be inoculated into enrichment cultures of a bioreactor of the invention.

In alternative embodiments the invention provides methods for analysis and understanding of subsurface microbial communities responsible for conversion of coal and coal-like substrates into methane, and for controlling geochemical conditions. Thus, in alternative embodiments, the invention, compositions and methods of the invention are used to stimulate preferred subsurface methanogenesis pathways and to enhance the rates of biogas formation.

In alternative embodiments, compositions and methods of the invention supply deficient nutrients (e.g., enhanced metal salts of compounds found in methylotrophic/bacterial enzymes, non-inhibitory level of alternate electron acceptors such as iron, manganese, or other nutrients and trace elements identified by correlating nutrient abundance to microbial growth/methane production) and/or modifying some parameters of the formation water (e.g., higher pH to the optimal range of the microbial association from culture experiments at the reservoir temperature) can shift microbial populations of all wells towards more efficient coal/kerogen biodegrading (e.g., in Beluga methanol/methyl-generating) and increase the methanogenesis rates.

In alternative embodiments, compositions and methods of the invention comprise use of subsurface exploitation of methylotrophic (e.g., methanol and other methyl-containing) substrates under neutral to slightly alkaline conditions to enhanced biogas formation.

In alternative embodiments, methods of the invention identify: (a) key and fastest operating microbial pathway for subsurface biogas formation and (b) ranges of key environmental geochemical parameters that stimulate this pathway thus enabling a means to optimize subsurface biogas-production rates and generate a positive offset to the gas field's production decline. In alternative embodiments, careful stimulation of the subsurface bioreactor (by inspecting and adjusting chemistry and microbiology of co-produced and re-injected water) ensures potential long term stable methane production rate (10's of years), owing to vastness of accessible organic matter (organic debris and bedded coals) in the subsurface.

In alternative embodiments, the invention provides a specific integrated process for microbe discovery (including syntrophic associations between organic-matter degrading bacteria and gas-producing Archaea) and an optimization strategy for developing a supplemental water injectate promoting biogas growth and minimizing deleterious effects.

In alternative embodiments, the invention can assess the formation of carbon mass and characterize the geochemical bio-convertibility of organic matter, and follow-up enrichment experiments on indigenous formations required for potentially successful field implementation. Amendments can be extremely cost-effective.

In alternative embodiments, compositions and methods provided can be practiced to enhance and produce natural gases from certain Cook Inlet fields which contain biogenic methane almost exclusively. In alternative embodiments, compositions and methods provided can be used to enhance microbial communities that are still active at present day in both the Beluga and Sterling formations, degrading complex organic matter to simpler compounds that in turn can be biologically transformed to methane. Thin coals and dispersed organic debris in the sand-dominated fluvial system are easily accessible for microbial attack. Faster rates of biodegradation and methanogenesis can be achieved by selecting for specific microbial populations through adjusting the chemistry of formation waters (i.e. pH, Eh, as well as trace elements and nutrients such as Mo, Ni, phosphate, ammonia, etc.).

Several parameters of Cook Inlet microbial communities including 16S rRNA gene profiling, metagenomics analysis, cultivation screens and geochemical analysis were studied in the lab for potential future field implementation. Both the Beluga and Sterling formations are excellent candidates for a field pilot for enhancement of microbial methane generation. These formations have low reservoir temperatures, association of organic matter within and adjacent to highly porous and permeable sands with organic debris and nutritious volcanic ash, and reasonably good lateral connectivity within the Sterling formation reservoirs.

DNA, culturing, and geochemistry of Cook Inlet microbial associations were studied in the lab for potential future field implementation. Both the Beluga and Sterling formations are excellent candidates for a field pilot for enhancement of biogas. These formations have low reservoir temperatures, association of organic matter within and adjacent to highly porous and permeable sands with organic debris and nutritious volcanic ash, and reasonably good lateral connectivity within the Sterling formation reservoirs.

In alternative embodiments, the term "carbonaceous" is defined as any rock containing organic carbon (carbonaceous rocks such as coal, shale, sandstone or limestone with organic debris or oil) with a total organic carbon (TOC) content >0.5 weight % (wt. %).

In alternative embodiments, the term "coal" is defined as a readily combustible rock containing >50 wt. % TOC.

In alternative embodiments, the term "correlation" is defined as the relationship or degree of similarity between two variables. Correlation analyses may be performed by any method or calculation known in the art. Correlation analyses for R and $R_2$ may be performed as described by M. J. Schmidt in Understanding and Using Statistics, 1975 (D. C. Health and Company), pages 131-147. The degree of correlation for R is defined as follows:

| | |
|---|---|
| 1.0 | Perfect |
| 0.7-0.99 | High |
| 0.5-0.7 | Moderate |
| 0.3-0.5 | Low |
| 0.1-0.3 | Negligible |

In alternative embodiments, the term "field observation" is defined as the set of reservoir parameters that include: gas composition and isotopes, water chemistry, pH, salinity, Eh (redox potential), temperature, depth, production parameters and history, description and characterization of the formation, e.g. description, sampling or analyses of core, cuttings or outcrop rock material.

In alternative embodiments, the term "production water" is defined as water recovered co-produced with any petroleum or hydrocarbon products at the well head.

In alternative embodiments, the term "recalcitrant organic matter" is defined as any organic matter that is generally resistant to biodegradation by the action of microorganisms, e.g. highly aromatic coals.

In alternative embodiments, the term "chemical analogue" is defines as specific chemical compound or compounds of structure and bond types representative of the target carbonaceous material. Such chemically defined analogue has known chemical structure, is commercially available and can be used as a surrogate for faster growth of targeted consortium.

In alternative embodiments, biogenic gas formation is modeled in one or more subsurface formations. Biogenic gas formation modeling includes determining changes in the formation composition and gas formation as biogenic growth occurs. Modeling includes estimating changes in organic matter content in the formation, volume of gas generated during biogenic growth, and determination of potential gas flow paths through the formation and travel time of biogas from biogenesis to production, based on a geological characterization and model of the formation.

In alternative embodiments, careful sample collection of gases and the co-produced water at the well-head improved identification of microbial communities associated with potentially commercial geochemical processes and was facilitated by proper treatment of water samples to preserve microbes and water chemistry during transit to and storage at the laboratory. About 1 L of non-filtered water was collected for DNA extraction and 16S rRNA gene profiling using pyrosequencing. Additional water samples were collected in 160 mL serum bottles for enrichments (amended with resazurin and sodium sulfide with blue butyl stoppers). Another 1.5 L of water was filtered on-site using 0.22 µm pore size filters. Filtered water samples were split for variety of subsequent analyses including inorganic (cations—fixed with HCl, anions) and organic chemistry (volatile fatty acids—amended with benzalkonium chloride, alcohols). Well-head gas samples were taken for molecular and isotopic composition of the gas using e.g., ISOTUBES™ (IsoTech). In addition, the field pH, Eh, salinity, temperature of the waters, alkalinity (via titration), and/or other properties were measured as soon as possible after water collection. In alternative embodiments, an integrated (wide and deep) screening of both geochemical and microbiological environmental properties was used to characterize subsurface microbial environments; thus, providing an accurate background for the composition of the reservoir.

In another embodiment, genomic DNA is extracted from samples of a subsurface carbonaceous reservoir of interest. Genomic DNA may be extracted from the samples by any of a number of commercially available kits (e.g., POWERSOIL™ available from MoBio Laboratories Inc. (Carlsbad, Calif.) or FASTDNA™ kit by Q Biogene) or by methods ordinarily known by those skilled in the art of environmental microbiology. The microbial communities resident in the reservoir samples are profiled (or inventoried) by determining the DNA sequence of a portion of the 16S rRNA genes present. This gene is widely used as an indicator, or barcode for a given microbial species (Pace, 1997). The 16S rRNA genes are recovered from genomic DNA through PCR amplification using primers that are designed to conserved regions with the gene. Such primers are well known in the art. For example, the primers TX9 and 1391R (e.g., see Ashby, Rine et al. 2007, see list below) amplify an approximately 600 base-pair region of the 16S rRNA gene that includes the fifth through eighth variable (V5-V8) regions. The DNA sequence of the resulting 16S rRNA amplicon may be determined using any available technology including, but not limited to, Sanger, or 'next generation' technologies such as those available from Roche, ABI, Illumina, Ion Torrent or Pacific Biosciences. Determination of the number of times each sequence occurs in a sample provides an indication of the microbial community structure (e.g., see Ashby, Rine et al. 2007). The abundance of each sequence identified from a given sample can be compared with that of every other sequence to identify sequences that show significant correlations to one another. These sequences are likely to be members of the same consortium and participate in common biogeochemical process (Ashby 2003). The microbial communities may also be characterized by sequencing genes other than the 16S rRNA genes or even by random shotgun sequencing of genomic fragments by methods that are well known in the art, (Venter, Remington et al. 2004). The microbial communities may also be characterized by cultivation dependent approaches that are well known in the art. For example, this approach may identify organisms through metabolic capabilities, morphological considerations and Gram stains. Total count of microbial sequences in the Cook Inlet gas field was dominated by *Methanolobus* (FIG. 1).

Figure 2:
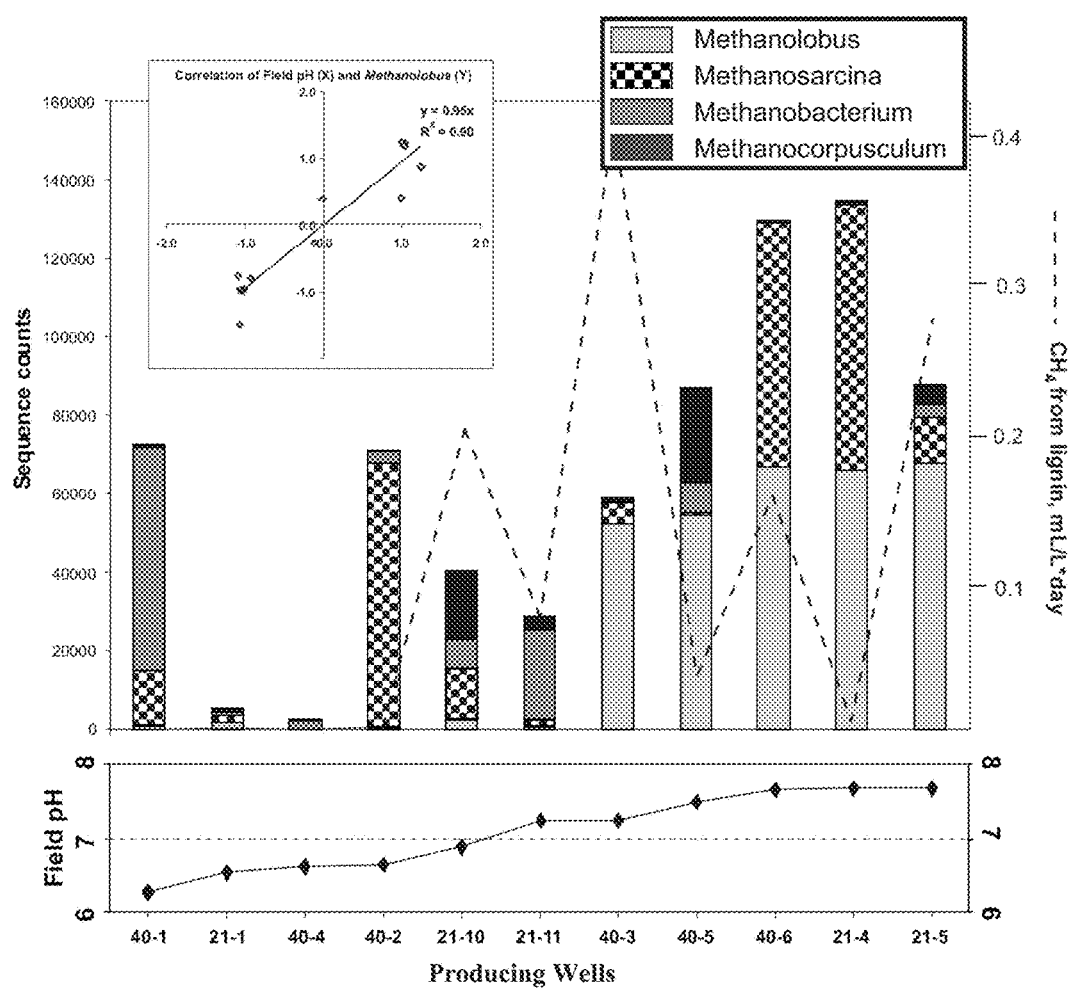
FIG. 2: graphically illustrates the Distribution of Archaeal populations along pH gradient (bottom panel) in the Cook Inlet wells. Note high pH and high methane production rates typically coincide with significant fraction of *Methanolobus*. High positive correlation between field-measured pH of formation water and *Methanolobus* population (data log transformed and Z-scored) is indicated in the inset.

In one embodiment, specific target microbial Bacteria-Archaea associations favorable for biogas production are identified through an integrated water and gas-sampling strategy that allowed for the search across biological and geochemical parameters for environmental correlations between microbe associations and key chemical processes with potential commercial value. For the purposes of high-grading enhanced biomethane production, the correlations have been based on two specific microbial enrichments of the Cook Inlet formation waters with: (a) common methanogenic substrates (combination of $CO_2/H_2$, acetate, methanol substrates) to gauge the general health of the endemic methanogenic community and (b) with lignin/lignin monomers-supplemented Cook Inlet coals/organic matter-rich sandstone enrichments to simulate further the bacterial breakdown of organic macromolecules to specific substrates vital to the growth of key Archaeal methanogens. Statistical correlation of geochemical data from the formation water and the microbial distribution data (expressed as Z score values of log-transformed 16S rRNA gene sequence occurrence data) has successfully identified microbial associations and potential syntrophies as well as their affiliation to specific ranges of geochemical parameters (i.e. pH, salinity, temperature, trace metals, gas isotopic composition). Sequence occurrence and geochemistry data from multiple wells and/or basins can be used. For the Cook Inlet gas fields, 16S rRNA gene pyrosequencing data integrated with these two biogas-production datasets clearly show that methanol and other methyl-containing species are the most efficient substrates for biogas formation via the methylotrophic pathway. The highest methane production rate corresponded to highest formation-water pH and was dominated by methanol/methyl utilizing genus *Methanolobus* (FIG. 2). The correlations of 16S rRNA sequence data achieved with new generation 454-sequencer also pointed out specific microbial associations and potential syntrophies between different microbial groups. For example, Family Methanosarcinaceae (Class Methanomicrobia) is capable of utilizing methyl-containing compounds (i.e. methylamines) as substrates for methanogenesis and the main Cook Inlet methanogens belong to this family: *Methanolobus* and *Methanosarcina*.

Lab experiments were able to determine the ability of microbial cultures or microbes present in produced water to convert different types of organic matter (OM) to methane: (a) subsurface OM (2 types of coal, (b) coal-mimicking substrates (i.e. lignin mix, 0.4 mL/L*d, yield up to 15% mass to mass), and (c) biowaste materials (i.e. refinery sludge, biocoals, up to 0.9 mL/L*d). Furthermore, molybdenum (Mo) (good correlation with methanogenesis rate), nickel (Ni), tungsten (W), phosphate and ammonia were considered as important nutrients.

Additionally, the methylotrophic biogas formation correlated with neutral to slightly alkaline conditions in the formation waters (FIG. 2, pH greater than 7.2 with an optimum approximately 7.5). Methanogenesis rate is measured using a pressure transducer and GC/FID. Alternatively, rates of intermediate steps can be measured, by inhibiting methanogens (i.e. with BESA) and analyzing the enrichment water chemistry including volatile fatty acids (VFA's), alcohols and the like. Similarly, substrate material (i.e. coal, oil-sands, bitumen, and the like) can be characterized before and after enrichment (i.e. conversion to methane) for chemical structure (i.e. NMR, FTIR). The bacterial break-down polymers of macromolecular subsurface OM (the rate limiting step) can be also enriched by using: (a) potential synthetic syntrophic microbial associations inferred from this research or (b) by amending an enrichment of indigenous microbial populations (i.e. on coal or coal analogues).

In another embodiment, unfavorable endemic bacteria or environmental conditions affecting biogas formation were identified. Endemic bacteria that did not produce methane, environment unfavorable to endemic microbes that did produce methane, or conditions that show a negative correlation to biogas (e.g., methane) formation were identified. The integrated data from microbial DNA, geochemistry, and biogas production via enrichment experiments are also used to find negative correlations, indicating possible specific microbes or environmental conditions deleterious to biogas formation. Negative correlation within DNA sequences and against geochemistry are also taken into account as potential microbial rivalry/inhibition and toxicity/unfavorable chemical conditions (i.e. high propionate concentration, large populations of nitrate or sulfate reducing bacteria, typically inhibiting methanogens), respectively. Potential risk of fouling of the bioreactor including production hydrogen sulfide and accumulation non-reactive acidic products is an important element of the targeted injectate-water recipe, such that biogas formation by the methylotrophic pathway is optimized for their essential growth substrates without impeding production due to other factors. For example, microbial populations derived from the Cook Inlet subsurface waters are also tested for the extent of microbial removal of individual VFAs and retardation of microbial pathways leading to potential VFA buildup (and lowered pH to unfavorable acidic conditions). Microbial populations from most of the wells were capable of stoichiometric conversion of butyrate and acetate to $CH_4$ within a few months. In contrast, propionate was not degraded in any of the samples and its buildup in a subsurface bioreactor has a likely deleterious impact on biogas production by the methylotrophic pathway. Therefore, in some embodiments, potential stimulation of propionate generation via supplemental injectate-water must be avoided. In addition, the introduction of certain anions such as sulfate and nitrate is to be avoided.

In one embodiment, injection zone placement and injectate water composition were determined based on formation characterization in organic carbon-rich formations and through inorganic mineralogy. The carbonaceous substrate is as important as the microbial community in achieving biogas formation at economically significant rates. Our work shows a relationship between biogas rate and substrate thermal maturity (measured by vitrinite reflectance or another geochemical parameter expressed in vitrinite-reflectance equivalence). Furthermore, the formations targeted for stimulated biogas growth must have sufficient organic mass, contain microbial enzyme-accessible chemical-bond types, and also allow for fluid injectability at sufficiently meaningful rates. Thus, in alternative embodiments, methods of the invention can comprise geochemical characterization of: (a) the mineralogy (e.g., content of the nutritious volcanic ash clays using XRD, their chemical composition and ion exchange potential using SEM/EDS, association with organic matter particles using thin sections and SEM), (b) organic matter (functional groups and bond type distribution using NMR, TOC, ROCK-EVAL™ pyrolysis, organic petrography including vitrinite reflectance and OM fluorescence), and (c) correlation of organic-content of core samples to well-logs for biogas resourcing, and formation-evaluation of fluid flow (porosity, permeability, swelling). In addition, clays and other minerals within the organic matter-rich formations can be studied for ion exchange. Potential interactions between any proposed injectate and indigenous formation water can be evaluated using advanced physical-chemical and transport modeling.

Figure 6:
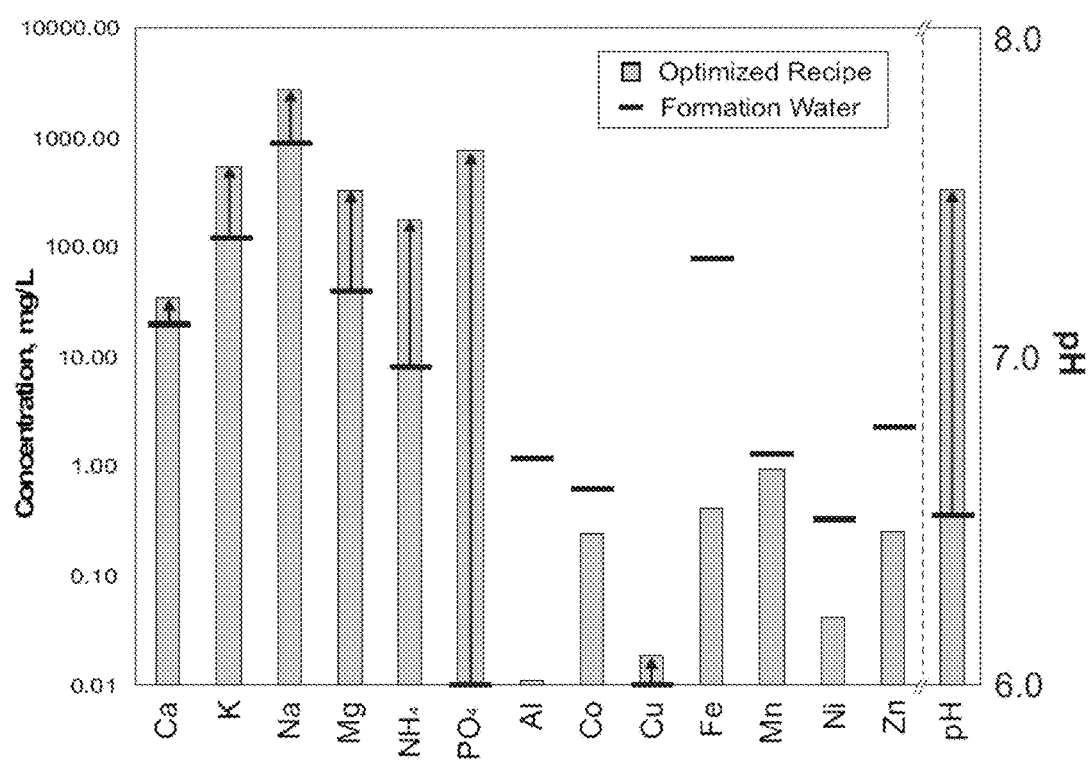
FIG. 6: graphically illustrates a Visual representation of formation water adjustment to the optimized recipe. Example formation water composition co-produced from one of the Cook Inlet gas wells. Required adjustment of parameters is represented by arrows.

In another embodiment, injectate water chemistry is optimized for biogas production enhancement. Methods of the invention comprise use of geochemical correlations with desired microbial associations to optimize biogas-formation rate/yield by chemistry adjustment; this information is used to make a injectate-water recipe used to practice this invention, including the use of pH buffers. The highest biogas-formation on an ideal substrate medium (combination of $CO_2/H_2$, acetate, methanol) and highest biogas production rate on a lignin/lignin monomers-supplemented Cook Inlet coal-lignin enrichment has been achieved by the methyl/methanol-pathway associated microbial community derived exclusively from wells with pH>7.23 (FIG. 2), strongly implying higher pH as an alternative condition (neutral-slightly alkaline) and an important basic makeup of injectate-water recipes of this invention. Thus, in another embodiment, compositions and methods comprise use of relatively alkaline (high) pH nutrients, injectate-water, liquid recipes and the like, and use of buffers biasing an alkaline (high) pH. In alternative embodiments, injectate water may also include supplementation with the best performing microbes on target substrate or its chemical analogue, even if derived from different environment (e.g. another oil or CBM basin), that performed well in the enrichments. For the targeted fields, the indigenous mineralogy, organic matter, porosity structure are likely to affect the growth of methanogenic microbes, and in some cases, microbial biofilm (e.g., via surface adhesion and mining nutritious mineralogy due to the presence of clays, volcanic ash, and/or organic debris) under the supplemented water conditions. Therefore, the targeted microbial community and favorable environment (e.g., optimized pH, supplemental macro- and micro-nutrients, vitamins) may be adjusted for interactions with the native organic-containing formations (FIG. 6). In addition, undesirable dissolution or precipitation of mineral phases potentially harmful to the microbes or the reservoir quality can be assessed; e.g. tested using chemical modeling, PHREEQC—mineral solubility changes caused by interactions of formation water and minerals with the injectate. A minimalistic approach can be used to favorably enhance the targeted biogas-forming bacterial-archaeal microbial association, while not promoting over-enhanced growth of other microbes not important to the biogas formation process (i.e., to avoid water injection delivery problems due to biofilm plugging around well injectors).

Figure 4:
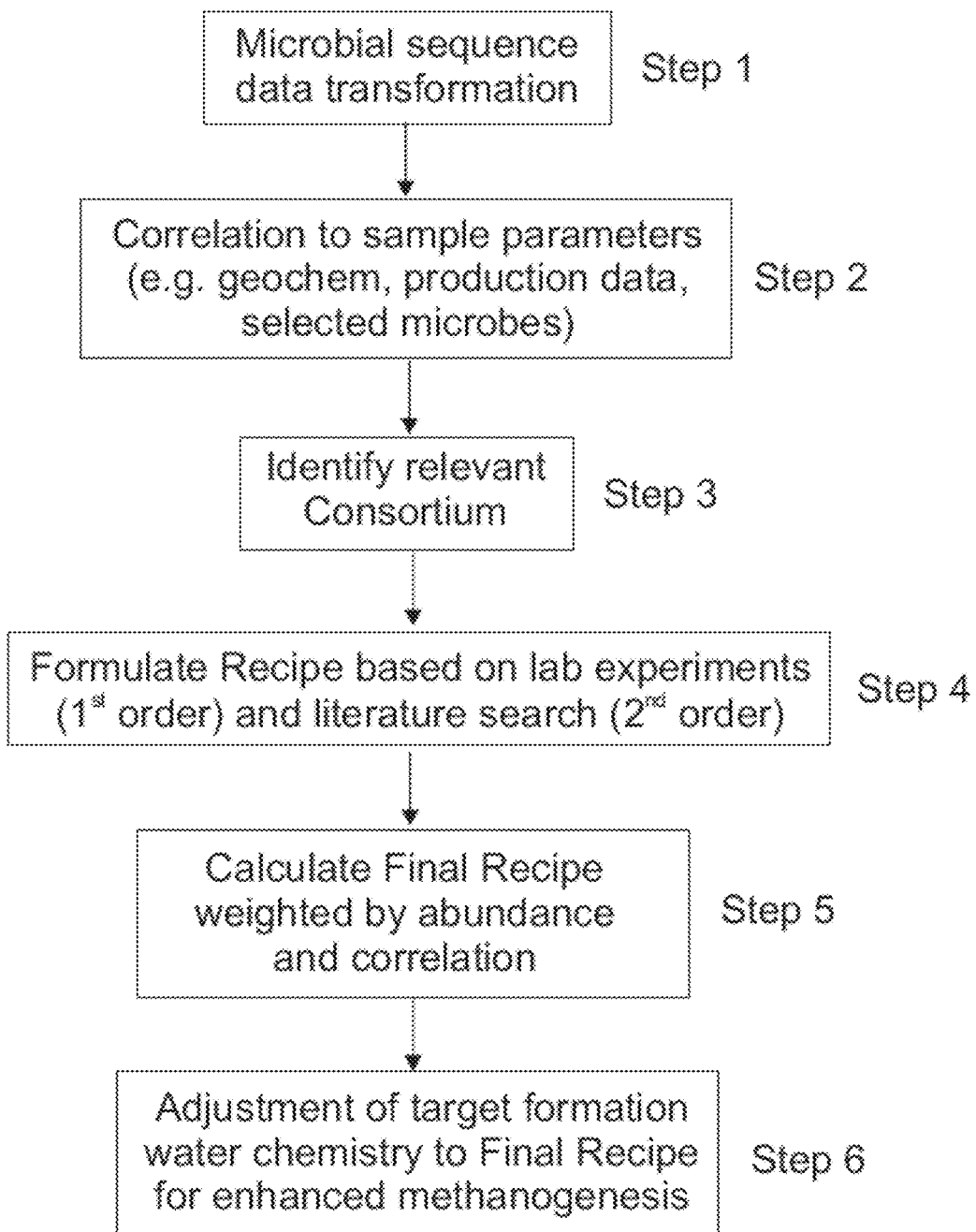
FIG. 4: is a Schematic of an exemplary process of this invention for creating optimized chemical recipe for enhanced microbial methanogenesis.

In one embodiment, customized nutrient amendments are provided. A nutrient mix customized for a specific microbial community, which e.g., can be developed by the following steps (FIGS. 4 and 5):

1. Transform microbial 16S rRNA gene sequence count data for all samples including: adding a small value to each sequence count (e.g. add ⅒th of the lowest value observed to every sequence count, thus avoiding taking log of zero; log 20 transform sequence counts and determine Z-scores (for a given sequence in a given well, by subtracting the mean value of the occurrence of a given sequence in all wells examined and dividing the resulting number by the standard deviation of the same array)

2. Determine correlation of the distribution of all sequences to distribution of target sequences, e.g. dominant methanogens responsible for leading methanogenic pathway (tested experimentally with coal/lignin/lignin monomers incubations, e.g. dominating *Methanolobus* sequence using transformed data) to obtain Pearson correlation coefficients Ra and Rb.

3. Sort sequences based on their R values. Select sequences with R higher than cut off value (e.g. 0.70). Subsequently, remove sequences with low counts (e.g. 300) with small contribution to the community and having the sequence count in a range of potential sequencing error.

4. Remaining sequences form so called Consortium, consisting of bacteria (b) and Archaea (a) related or similarly distributed to the selected dominant methanogen. Correlations to sum of several grouped sequences (e.g. syntrophic microorganisms) can be also used.

5. 16S rRNA gene sequences in the Consortium are identified by comparison to annotated DNA sequence database (e.g. NCBI).

6. Nutrient and growth condition (e.g. pH, Cl—, NH4+, etc.) requirements for of each of the selected microbial genus or microbial strains was determined using information from publicly available literatures and in certain cases using information from the German Resource Center for Biological Materials. From this, an optimal Recipe Concentration (CR) of each element (e.g. Mg) or condition (e.g. pH) X for each Consortium member (a or b) was obtained.

7. Final Recipe Concentration ($C_{FR}$) of given element or condition (X) for entire Consortium is obtained by using following equation (1):

$$C_{FR,X} = f_B \times \sum_n C_{R,X,bn} \times f_{bn} \times r_{bn} + f_A \times \sum_m C_{R,X,am} \times f_{am} r_{am} \quad (1)$$

Where $C_{FR,X}$ is the final recipe concentration of element X for a value or condition X, e.g. pH; $C_{R,X,bn}$ is a literature-based recipe concentration of element or condition X; $f_B$ and $f_A$ are optional weighting parameters for bacteria vs Archaea in a population of targeted well, formation, and/or incubation conditions; $f_{bn}$ is the fraction of bacterial sequence n out of total bacterial sequence count within the consortium; $f_{am}$ is the fraction of archaeal sequence m out of total archaeal sequence count within the consortium; $r_{bn}$ is the Pearson correlation coefficient of a bacterial sequence n to selected dominant sequence (e.g. main methanogen) or grouped sequences (e.g. syntrophic association); and $r_{am}$ is the Pearson correlation coefficient of an archaeal sequence m to selected dominant sequence (e.g. main methanogen) or grouped sequences (e.g. syntrophic association). If conditions for Archaea and bacteria are equal both $f_A$ and $f_B$ parameters are equal to 0.5. If however, Archaea or bacteria are dominant in a formation or injectate, or if Archaea or bacteria are more critical or rate limiting, $f_A$ or $f_B$ can be adjusted to account for differences in consortium population, overall activity, or other factors dependent upon the specific process or conditions in the targeted well, formation, and/or incubation.

8. Final calculated $C_{FR}$ values contribute to the final recipe (FR).

Figure 7:
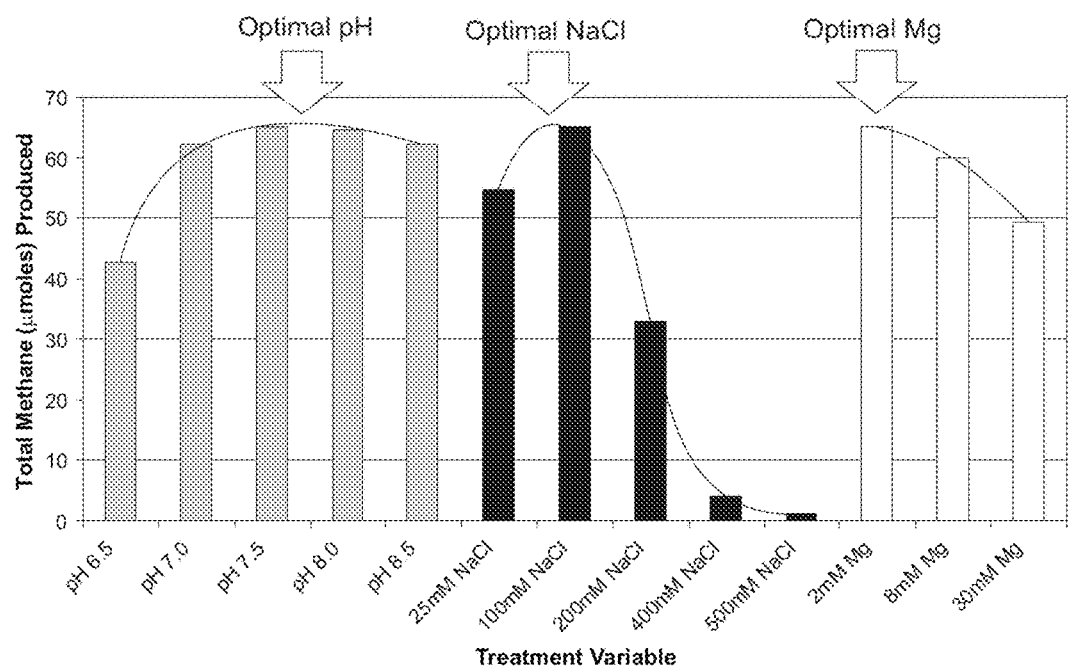
FIG. 7: graphically illustrates an Example of optimization methane production from Cook Inlet rock material by varying single parameter in sand-pack incubations (total methane produced after 6 weeks of incubation).

9. Additional minor adjustments of the calculated parameters are tested one parameter at a time while maintaining other parameters. In one embodiment changes are assessed in a sand-pack bioreactor (Table 1, FIG. 7).

10. Subtract all amendments (X) present in the formation water (FW) to obtain an adjusted final recipe (AFR) for the current well conditions (FIG. 6).

11. Small adjustments to the AFR may be made to accommodate charge balance, increase chemical stability, and ensure no precipitation occurs during mixing, storage, injection or under formation conditions. Chemical stability may be calculated using PHREEQC™, PHREEQCI™ or PHAST software from USGS and others, AQUACHEM™ from Waterloo, Inc., ROCKWARE™, as well as other programs are also available to analyze water salinity and precipitation under various conditions.

The nutrient composition may be introduced to the reservoir through injection of a single bolus, through a continuous (e.g., a bleed in) process, or a pulsed process. The AFR may be amended dependent upon the changes in the production water, methane production, and/or microbial composition over time. The same methods used to re-inject produced water into a well may be used to inject/re-inject a mixture of produced water and nutrient concentrate.

Figure 11:
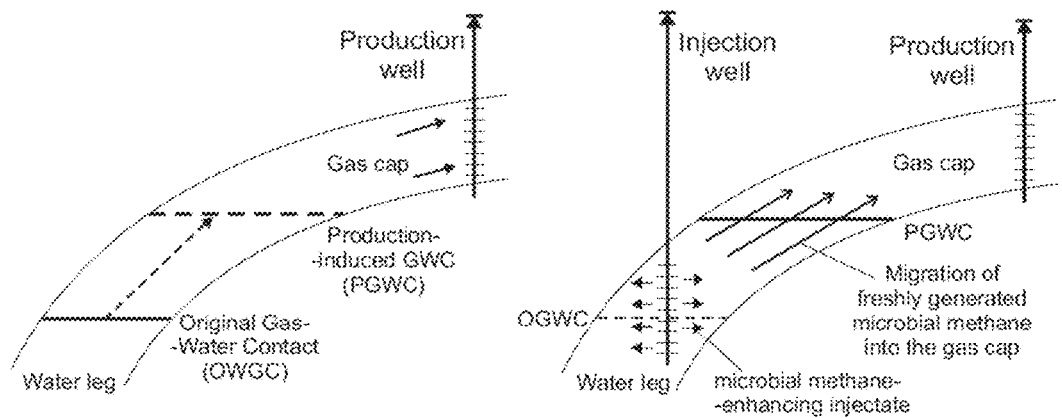
FIG. 11: schematically illustrates an exemplary mechanism or method of the invention for enhancement of biogas generation in a highly permeable formation with predominantly dispersed organic debris and thin bedded coals; in one embodiment, injection of nutrient-amended injectate into the water leg down dip and/or into production-induced water leg stimulates biogas generation and migration up-dip towards gas cap and production well.

In another embodiment, the final water injectate is delivered to the target formation to induce or increase biogas production. Field implementation, delivery of the designed injectate, may be improved where good well-to-well connectivity exists through highly permeable continuous formation intervals. Core description, geophysical logs, and permeability/porosity data may be used to identify target wells, optimize injection intervals, and improve biogenic gas production. For sandstones containing dispersed organic debris, injection of supplemented water may be applied to the: (a) near-water leg or (b) previously depleted gas-bearing zones, in the same formation down-dip from the free-gas zone (FIG. 11). Consequently, new microbial gas formed in the water leg migrates upwards to the gas column, supplementing the overall gas reserves. Nevertheless, converting these large resources of sub-surface organic matter require that the injectate-water supplement contact a large volume of the formation, without choking off injection around the well-bore due to biofilm growth. Therefore, an important consideration prior to implementation is investigation of the use of time-release substances or near-well toxic concentrations to prevent biofilm plugging, followed up by bench testing on target formations. In an alternative embodiment, the methods involve continuous injection of nutrients at final concentration (e.g. bleed in of concentrated nutrients into produced water-disposal well). Another option is delivery of nutrients with the fracturing fluids used often during completion or re-completion of gas producing wells.

In alternative embodiments, tracing injected water migration, biogas formation and changes in microbial communities are critical to benchmarking success. Water migration can be traced using water soluble geochemical tracers (i.e. stable or radio isotopically labeled ions such as $^{13}C$ or $^{14}C$ carbonate and $^{129}$iodine or $^{36}$chlorine, bromide). Newly generated biogas can be traced from gas isotopes, using $^{14}C$, $^{13}C$, $^{2}H$ or $^{3}H$ enriched methanogenic substrates, including bicarbonate, lignin and aromatic monomers. Additionally, production profile of nearby producing wells can be observed together with gas to water ratio, gas pressure, production rates, and gas dryness. Biomass tracers of newly grown microbes can be also used, including $^{14}C$, $^{13}C$, $^{2}H$ or $^{3}H$-labeled organic compounds (i.e. lignin monomers, DNA, amino acids, bacteriophage, or other coal analogues, i.e. aromatic substrates listed in Example 4), $^{14}N$-enriched ammonia. Monitoring will also include microbial community changes through RNA/DNA profiling, RNA/DNA yields.

Figure 3:
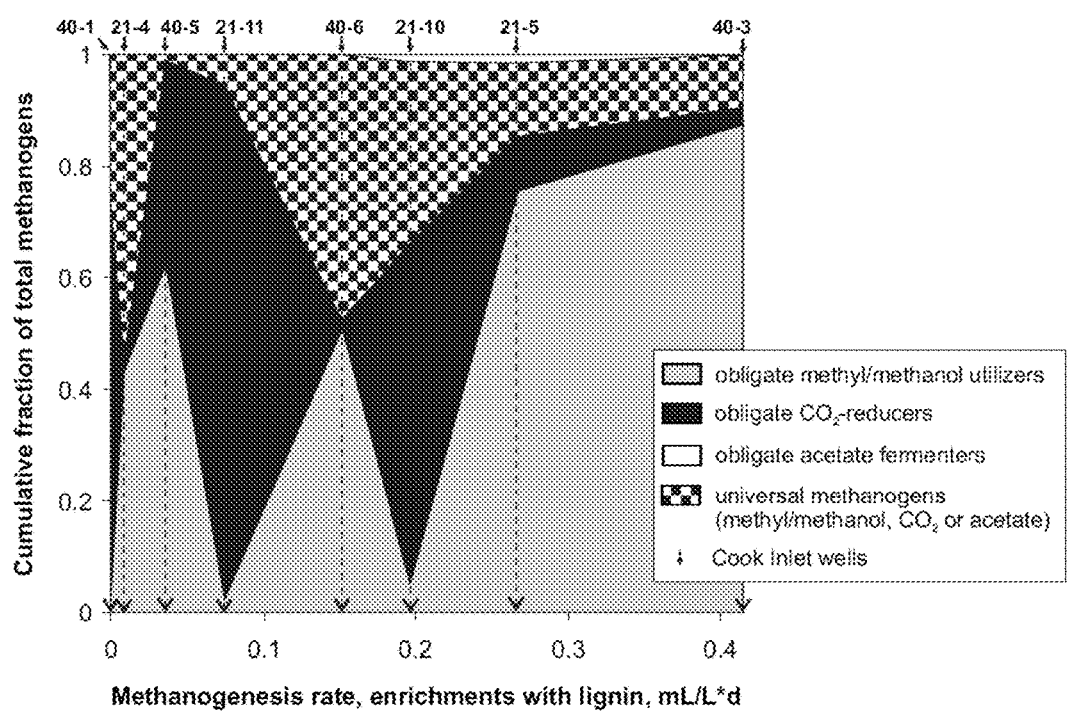
FIG. 3: graphically illustrates Methanogenesis rates from coal/lignin/lignin monomers and fractions of methanogens split into substrate-specific categories. Microbial populations from two wells with largest fraction of obligate methyl/methanol utilizers (40-3 and 21-5) obtained highest rates of methanogenesis expressed as mL of $CH_4$ per L of medium per day. Wells 21-1, 21-4, and 40-1 from FIG. 2 not shown due to little or no methane production.

In another embodiment, chemical analogs of subsurface organic matter-containing rocks allow for quick growth of biomass in microbial consortia that can be re-injected, e.g. when the optimized nutrient mix is identified. For low thermal maturity coals, a lignin monomer mixture has been used to benchmark high methane producing consortia capable of the critical depolymerization step (FIG. 3). Coal depolymerization is thought to be rate limiting in the coal biogasification process. For higher maturity coals (about 0.6 to 1.4% $R_O$) aromatic analogs are tested as surrogates for biogas formation, including biphenyl 4-methanol, methoxy biphenyl 1,1,-biphenyl, methyl, dimethyl, phenanthrene, and other compounds that mimic degraded coal monomers.

In one embodiment, a biogenic gas formation is assessed by developing a facies model, determining formation parameters and distributing these parameters for each facies in a geocellular model. This geocellular model can then be used to simulate and history match any previous gas/water production to validate the model, and then to simulate future biogenic gas production with nutrient optimization. As biogenic gas production continues, the initial model may be updated based on current production trends with optimized nutrient formulations. One or more geocellular models may be developed using numerous formation modeling techniques including ECLIPSE™, GEOFINDIQ™ from Schlumberger, MPS (Multiple-Point Statistics), FDM (Facies Distribution Modeling) and other geocellular modeling techniques and programs, including techniques and tools developed in house or by independent programmers. Formation parameters can include % TOC (total organic carbon), density, porosity, permeability, pressure distribution, saturation (gas, water, fluid, oil, etc.), conductivity, impedance, continuity, flow rate or velocity, volume, compressibility, thickness, fluid viscosity, and other properties. Formation parameters may be measured directly or indirectly through well logging, measured through core samples and analysis, or estimated based on various formation properties. Formation properties may be distributed by estimating from one sample well to the next, interpolating, or applied by simulation algorithms including Kriging, stochastic simulation, Markov Chain Monte Carlo distribution, and the like, as well as combinations of these methods. Biogenic gas production can be simulated using STARS™ from Computer Modeling Group, Ltd., JEWELSUITE™ from Baker Huges, BASINMOD™ from Platte River, or other reservoir simulation software as well as programs designed and developed in house or by independent programmers. Some software may incorporate both geocellular modeling and reservoir simulation.

In another embodiment, a geocellular model is developed as described above and used to test gas flow, travel time, and continuity of the reservoir against variabilities in key formation parameters, which may be the result of limited or conflicting geological data. Once these key parameter variabilities are identified, the reservoir analysis may be simplified. In one embodiment, the travel time for biogenic gas in the reservoir was determined by modeling the biogenic gas production rate as actual gas injection into an injection well. This allowed for multiple variations of the key parameters in the geocellular model to be simulated significantly faster than would be possible with a reservoir model which included the full biogenic gas production. This quick method helped to define the possible range in gas travel time based on variabilities in formation parameters and to identify which formation parameters are most influential on gas travel time and require further investigation to narrow their variability.

In another embodiment, risk analysis is used to identify potential risks, evaluate risk severity and probability, propose possible mitigation strategies, design tests for each risk, and test each risk and putative preventive action. Potential risks associated with biogenic gas production can be identified from product suppliers, through water acquisition, to nutrient injection, to microbe growth and biofilm formation. In one embodiment, potential risks include impurities in one or more of the nutrients, additives, treatments, water, or other feedstreams; contamination with oxygen, sulfur, or other compounds; contamination with one or more microbes; scaling in the injection line, wellbore and/or formation; biofilm formation in the mixing tank, storage tank, injection line, wellbore and/or formation; sludge formation in the mixing tank and/or storage tank; biocorrosion in the mixing tank, storage tank, and/or injection line; formation of hydrogen sulfide ($H_2S$); oxygen removal; biomass plugging; and the like, either individually or in conjunction with other risks. Some risks may contribute to or correlate with other risks, for example sludge formation in the storage tank and biofilm formation in the injection line may both be the related to increased biomass in the storage tank.

Additionally, in some embodiments, enrichment of bacterial cultures using analogues to target subsurface organic material including lignin and lignin monomers, soluble hydrocarbons, other soluble substrates that mimic the composition of the hydrocarbon formation are used to enhance microbial growth in vitro. Modeling components of the hydrocarbon formation using simple monomers identified in produced water and/or through decomposition of formation samples provides a ready source of soluble substrates for microbial growth and selection assays. This innovative approach to rapid microbial growth and selection allows development of chemical and microbial optimized amendments for the targeted methanogenic pathway and for enhanced methanogenesis rate. Amendments were tested under current field conditions developed to evaluate the potential for biomass formation and scale precipitation resulting from the addition of amendments, which could create operational problems in the gas production and water injection facilities in the field. Implementation of any enhanced biogas producing process must include the combined optimization of the reward (biogas formation) versus the risk factors (deleterious effects to overall gas production, corrosion/scaling, or gas quality).

The invention provides kits comprising compositions and methods of the invention, including instructions for use thereof. In alternative embodiments, the invention provides kits comprising a composition (e.g., a nutrient composition), product of manufacture (e.g., a bioreactor), or mixture (e.g., a nutrient mixture) or culture of cells of the invention; wherein optionally the kit further comprises instructions for practicing a method of the invention.

The following examples of certain embodiments of the invention are given. Each example is provided by way of explanation of the invention, one of many embodiments of the invention, and the following examples should not be read to limit, or define, the scope of the invention.

EXAMPLES

Example 1

Identification of *Methanolobus* Spp. for Methanogenic Degradation of Coal and Other Recalcitrant Organic Matter This Example describes the identification of *Methanolobus* spp. as major contributor to methanogenic degradation of coal and other recalcitrant organic matter in subsurface gas reservoirs.

Production water was collected from the separator unit at the well head from a number of gas wells from the Beluga River Unit on the Cook Inlet of Alaska. A portion of the water sample designated for microbiological analysis was maintained anaerobically in sterile containers supplemented with cysteine and resazurin (redox indicator) under an argon headspace. The samples were shipped cold to Taxon's facility in California by express delivery.

Genomic DNA was isolated from cell pellets obtained by centrifuging the production water at 4,000×g for 30 min at 4° C. The pellets were resuspended in phosphate buffer and transferred to bead beating tubes. Total genomic DNA was extracted by a bead beating procedure as described (Ashby, Rine et al. 2007). A portion of the 16S rRNA genes were PCR-amplified using the primers TX9/1391r, followed by agarose purification of the amplicons. The amplicons were amplified a second time using fusion primers to incorporate the A and B adapters in addition to barcodes that enabled multiplexing of samples into a single run.

The 16S rRNA gene amplicons were sequenced on a Roche 454™ sequencer using Titanium chemistry and standard shotgun sequencing kits following the manufacturer's protocol. Profiles were created by documenting the number of times each unique sequence occurred in each sample. Sequences corresponding to those of *Methanolobus* spp. were observed to be dominant members of the Cook Inlet subsurface communities (see FIG. 1). Annotation of the sequences was performed by BLAST comparisons (Altschul, Madden et al. 1997) to the Genbank database.

Example 2

Stimulation of Methanogenic Degradation of Coal and Recalcitrant Organic Matter in Model Sandpack Bioreactors by Adding Customized Nutrient Amendments of the Invention In order to create a culture condition that approximated the rock matrix found in the sub-surface gas reservoir, carbonaceous material recovered from core samples were mixed in the natural in situ ratios with sand in anaerobic tubes fitted with solid rubber stoppers that were crimp sealed.

Specifically, ASTM grade sand (17.8 g, U.S. Silica Company) was added into 15 ml polypropylene conical tubes which was followed by addition of carbonaceous materials (0.167 g each of coal, sandstone with organic debris, and volcanic ash, to represent Cook Inlet gas-bearing formation) that are derived from Miocene aged rocks (i.e. core samples) from the Beluga gas field in Alaska, U.S.A. Conical tubes representing control set-up was amended with 22.88 g of sand but without adding the carbonaceous materials. The mixture in the conical tubes was homogenized for 10 s with a vortex mixer, and all the materials above including several aliquot of sterile 3.5 g sands were transferred into an anaerobic chamber that has been equilibrated with an atmosphere of hydrogen, carbon dioxide and nitrogen (5:5:90% v/v, respectively). Then, the caps on the conical tubes were loosely opened in order to create anaerobic condition in the tubes. All experimental procedures from this point were carried out inside the anaerobic chamber.

After 24 h the mixture in the conical tubes that contained sand and carbonaceous materials was transferred into sterile glass tubes (15 mL) that was previously stored in the anaerobic chamber. This mixture of sand and carbonaceous materials was then overlaid with 3.5 g aliquot of sand to create a ~1 cm upper layer that is free of carbonaceous materials. The carbon-free mixture in the control conical tubes was also decanted into sterile test tubes but in this case it was not overlaid with another layer of sand. The orifice of each of the tube was capped with sterile stoppers and crimped-sealed with metal caps. All the tubes and its content were autoclaved for 20 min at 120.

Figure 5:
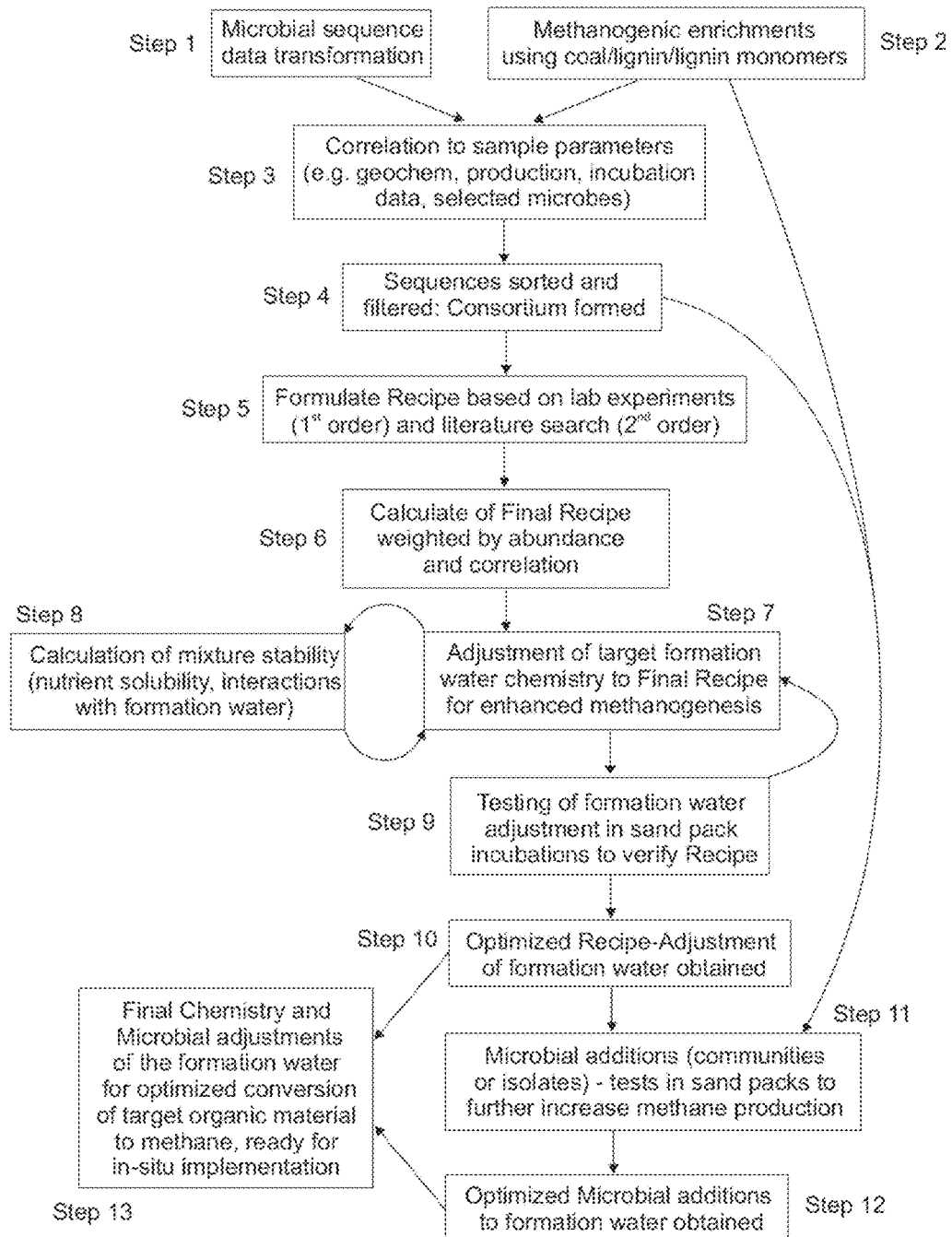
FIG. 5: is a Schematic of an exemplary process of this invention for creating optimized nutrient and microbial mixes or compositions, e.g., nutrient and microbial mixes or compositions of the invention.
Figure 8:
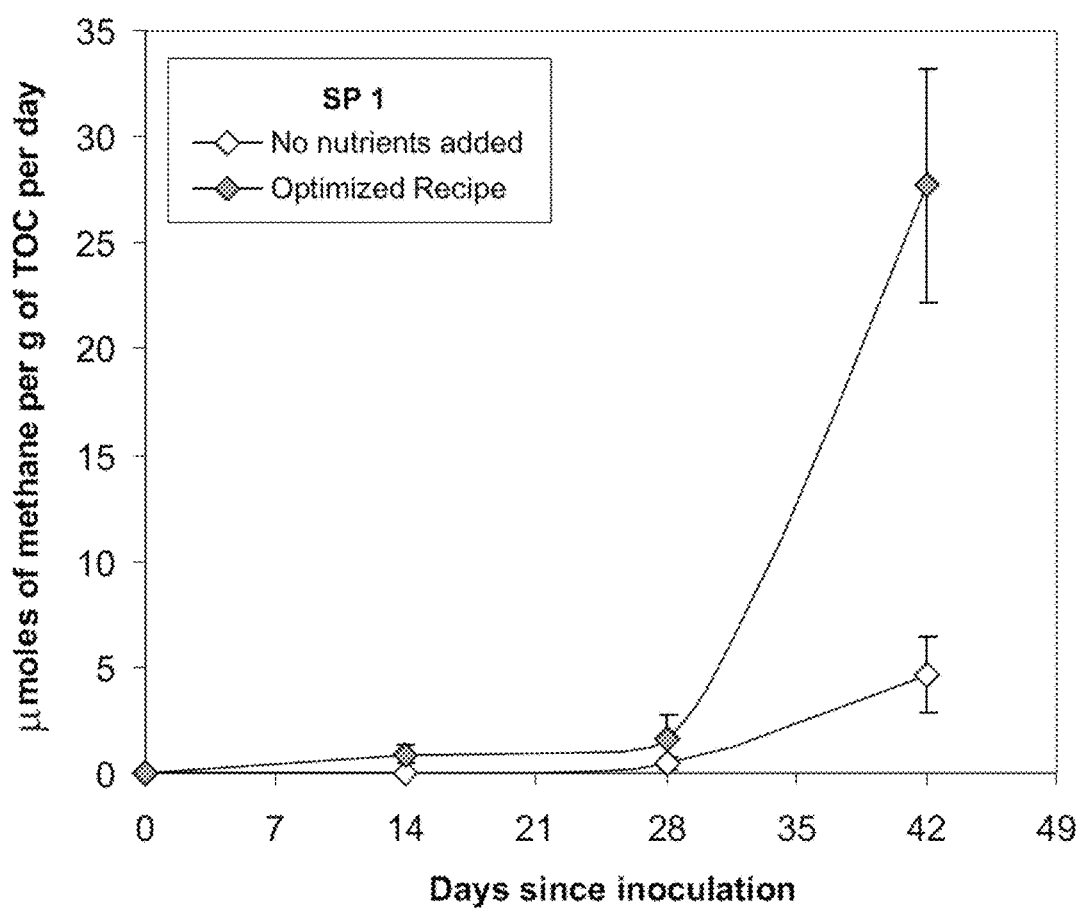
FIG. 8: graphically illustrates a Comparison of methane production rate from Cook Inlet rock material without and with optimized nutrient addition. Production water from 40-3 well. Production of methane without nutrient addition is significantly slower after 42 days of incubation. Each data point represents a triplicate set of sand pack tubes.
Figure 9:
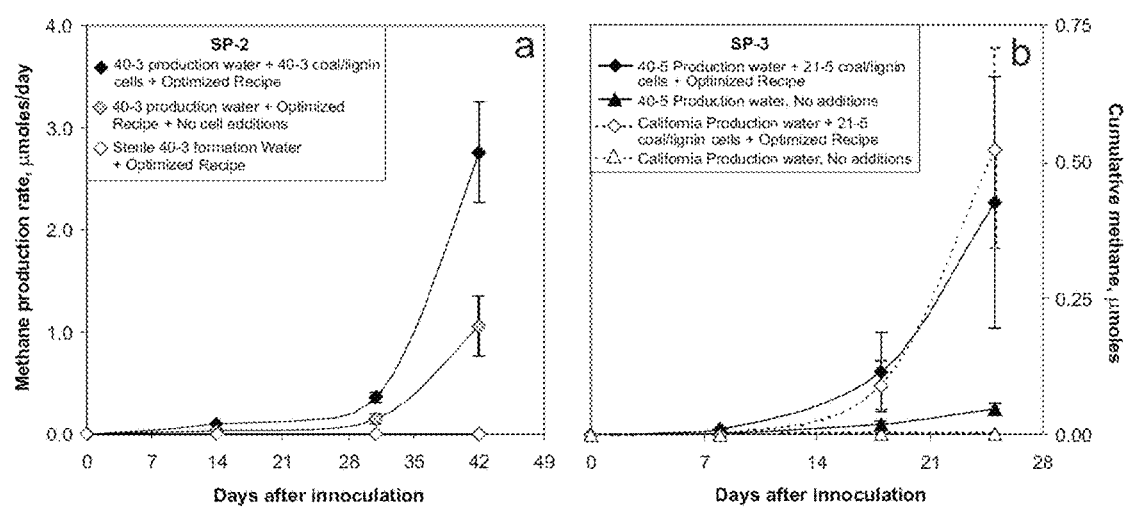
FIG. 9: graphically illustrates a Methane production from the Cook Inlet rock material; sand-pack incubations using cell additions of the Cook Inlet consortia grown on mixture of the Cook Inlet coal, lignin and lignin monomers.

The conditions for the experimental investigation are stated below:

i. Sand+unamended produced water from the targeted gas field ii. Sand/carbonaceous materials (organic rich rocks from targeted formations)+unamended produced water (FIG. 8)

iii. Sand/carbonaceous materials+standard nutrient amended produced water based on lab experiments (1st order) and literature search (2nd order) as shown in FIG. 5, Step 5 (results of sand pack experiments shown on FIG. 8)

iv. Sand/carbonaceous materials+standard nutrient amended produced water (FIG. 5, step 5) in which specific nutrient parameters were varied individually or in groups v. Sand/carbonaceous materials+coal/lignin-grown enrichments+optimized nutrient amended produced water (FIG. 5, Step 11);

TABLE 1

Stock solutions used to prepare media for sand pack experiments.

| Mineral nutrients (mg/l) | Trace Metal Solution$^a$ (mg/l) | Vitamins solution$^b$ (mg/l) |
|---|---|---|
| NaCl/KCl, 5844/7455 | Na-nitrilotriacetate, 1500 | p-Aminobenzoate, 50 |
| Na$_2$SO$_4$•10H$_2$O | FeCl$_2$•4H$_2$O, 200 | Biotin, 20 |
| NH$_4$Cl, 29.99 | MnCl$_2$•4H$_2$O, 100 | Cyanocobalamin, 5 |
| MgCl$_2$, 5.71 | NaWO$_4$•2H$_2$O, 20 | Folic, 20 |

TABLE 1-continued

Stock solutions used to prepare media for sand pack experiments.

| Mineral nutrients (mg/l) | Trace Metal Solution[a] (mg/l) | Vitamins solution[b] (mg/l) |
| --- | --- | --- |
| $Na_2HPO_4/NaH_2PO_4$, 55.36/46.79 | $CoCl_2 \cdot 6H_2O$, 100 | Lipoic acid, 50 |
|  | $ZnCl_2$, 50 | Nicotinic acid, 50 |
|  | $CuCl_2 \cdot 2H_2O$, 2 | Pyridoxine-HCl, 100 |
|  | $H_3BO_3$, 5 | Thiamine-HCl, 50 |
|  | $NaMoO_4 \cdot 2H_2O$, 10 | Riboflavin, 50 |
|  | $Na_2SeO_3$, 17 | Ca-Pantothenic |
|  | $NiCl_2 \cdot 6H_2O$, 24 | acid, 50 |

[a]Roh et al., 2006
[b]Zinder, S. H., Techniques in Microbial Ecology, p113-134

Stock solutions listed in Table 1 were used to prepare set of solutions for nutrient additions to the sand pack experiments with varying nutrient concentrations. The final optimized nutrient concentrations (mM) and the amount of other constituents in the standard optimized nutrient amended produced water (final pH 7.5) was: NaCl—KCl, 100 mM; $NH^{4+}$, 5.6 mM; $PO_4$, 7.8 mM; $Mg^{2+}$, 2 mM; $SO_4^{2-}$, 0; 1 ml Trace element solution, 1×; 1 ml vitamin solution, 1× (Table 1). The pH and concentration of NaCl—KCl, $NH^{4+}$, $PO_4$, $Mg^{2+}$, $SO_4^{2-}$, trace element solution, and vitamin solution, 1×. The tubes with produced water with lignin/coal-grown enrichment were separately prepared by addition of concentrated stock culture of cells, which were stored frozen at −80° C. and thawed prior to use.

The final volume of nutrient and/or cell amended produced water and the unamended produced water in all the tubes (i.e. tubes with sand and carbonaceous materials, and tubes with sand only) was 20 ml. All transfers into the tubes was done using a 20 gauge-6 inches BD spinal needle which allow the transfer of the mixtures at the bottom of the tube which allowed good distribution of the equilibrated mixture throughout the sand-packed tubes. All experimental and control sand-packed tubes were prepared in triplicates, and the tubes were capped with freshly prepared sterile 20 mm septum stopper which were crimped-sealed. The atmosphere in the headspace of all the tubes was replaced N2 (100% v/v) and they were immediately incubated at 20° C.

TABLE 2

Matrix of parameter variability

|  |  | BLANK | 0 | 1 | 2 | 3 | 4 | 5 |
| --- | --- | --- | --- | --- | --- | --- | --- | --- |
| 1 | pH | 7 |  | .5 |  | .5 |  | .5 |
| 2 | NaCl/KCl | 0 |  | 5 | 00 | 00 | 00 | 00 |
| 3 | $SO_4$ | 0 |  | .1 | .3 | .3 |  |  |
| 4 | $NH_4$ | 0 |  | .6 | 6.7 | 0 |  |  |
| 5 | $PO_4$ | 0 |  | .6 | .8 | 0 |  |  |
| 6 | Mg | 0 |  |  |  | 0 |  |  |
| 7 | Trace Metals | 0 |  | X | X | X |  |  |
| 8 | Vitamin Mix | 0 |  | X | X | X |  |  |

Recipe optimization used a matrix of parameter variability (Table 2: P1 to P8) to define eight variable parameters and v0 to v5 represent tested values of each parameter. Each tube was composed using the standard values of each parameter (highlighted) except for one which was varied. In this round of sand pack experiments included 23 tubes plus blanks (all in triplicates).

Initial methanogen cultivation tests of production water from the Beluga gas field revealed that *Methanolobus* had a salt optimum of 16 g/liter when grown on methanol and trimethylamine (TMA). Nevertheless, when the same production water was tested for salt optima using endemic coal as a substrate, the salt optimum was found to be 4 g/liter. This result revealed that the salt requirements of the entire degradative pathway must be considered when designing consensus nutrient mixes.

Example 3

Stimulation of Methanogenic Degradation of Coal and Recalcitrant Organic Matter in Model Sandpack Bioreactors by Adding *Methanolobus*

*Methanolobus* taylorii was added to sand pack tubes amended with target (Cook Inlet) coal/organic debris/volcanic ash, and optimized nutrient additions suspended in filter-sterilized, target production water. Rates of methane production were stimulated with addition of *M. taylorii* (FIG. 11).

Model sand pack bioreactors were set up as described in Example 2. Briefly, carbonaceous materials (0.167 g each of coal, sandstone with organic debris, and volcanic ash) from Cook Inlet core samples were mixed in the natural in situ ratios with 17.8 g of sand (U.S. Silica Company, ASTM grade) in Hungate tubes (18×150 mm) fitted with blue, butyl rubber stoppers. The components had been transferred into an anaerobic chamber, which is where assembly of the tubes and inoculations with microorganisms took place. The tubes containing carbonaceous material/sand were overlayed with pure sand, stoppered and crimped with aluminum caps, and then autoclaved for 20 minutes at 120° C.

Sterile sand pack tubes were brought back into the anaerobic chamber. Standard optimized nutrient conditions were used (see Example 2) and the final solutions, which also contained gas field production water amended with endogenous microorganisms+/−*M. taylorii*, were introduced into the tubes using a 20 gauge six inch spinal needle.

*Methanolobus taylorii* (#9005) was purchased from the Deutsche Sammlung von Mikroorganismen and Zellkulturen GmbH (DSMZ™), Braunschweig, Germany and grown in liquid culture using established techniques. The minimal essential medium (MEM-1) may be used as described by Zinder, S. H. in "Techniques in Microbial Ecology". The MEM-1 was supplemented with trimethylamine, 8 g/L sodium chloride, and mercaptoethane sulfonic acid (Coenzyme M), as well as the following antibiotics: vancomycin, streptomycin, kanamycin, penicillin G. *M. taylorii* was grown with a nitrogen headspace at room temperature, shaking, until turbid. Frozen stocks (−80° C.) of the organism were made by mixing turbid cultures with a 2× stock solution of freezing medium (final concentration 20% glycerol in MEM-1). For the sand pack inoculations, a concentrated frozen stock (1.8 mL) was thawed, added to reduced anaerobic mineral medium (RAMM), and washed once to remove glycerol and antibiotics. The cells were resuspended in production water plus nutrients before inoculation into sand pack tubes. The amount of cells added was indeterminate.

All experimental conditions were performed in triplicate. After inoculation, the atmosphere in the headspaces of all tubes was replaced with nitrogen, and the tubes were incubated at 20° C.

Example 4

Synthetic Consortia of the Invention

This example describes an exemplary method of making a composition of the invention, a synthetic consortia, and e.g., the so-called "Consort-ABS1" composition of the invention.

A collection of production water samples from a biogenic gas reservoir (Cook Inlet) was profiled and analyzed to test whether two-dimensional cluster analysis of 16S rRNA gene sequences would reveal the presence of a consortium of sequences (where the sequences serve as a proxy for the corresponding microbe) whose abundance distribution among the samples as a group corresponded to methanogenesis activity.

To isolate total genomic DNA, production water samples (250-500 mls) were filtered through a 47 mm 0.2 μm pore size Durapore membrane filter (Millipore, Billerica, Mass.). Using a sterile scalpel, filters were sliced into 96 equal sized portions and transferred equally into two 2.0 ml screw cap centrifuge tubes containing ceramic beads obtained from CeroGlass (Columbia, Tenn.). The bead-beating matrix consisted of one 4-mm glass bead (GSM-40), 0.75 g 1.4- to 1.6-mm zirconium silicate beads (SLZ-15), and 1.0 g 0.07- to 0.125-mm zirconium silicate beads (BSLZ-1) in 1 ml phosphate buffer (180 mM sodium phosphate, 18 mM EDTA, pH 8.0). Cells were disrupted in a Fastprep FP120 instrument as previously described (Ashby, Rine et al. 2007). Total genomic DNA was purified by centrifuging the lysed cells at 13,200×g for 5 min at 4° C. The supernatants were transferred to 1.5 ml centrifuge tubes and 250 μl of 2M potassium acetate pH 5.3 was added. The tubes were mixed by rotating end-over-end and were centrifuged as above. The resulting genomic DNA was purified on QIAprep Plasmid Spin columns (Qiagen, Valencia, Calif.) according to the manufacturer's instructions.

A portion of the 16S rRNA gene was amplified using the TX9/1391 primers as previously described (Ashby, Rine et al. 2007). Amplicons were agarose gel purified and quantitated using SYBR green (Invitrogen, Carlsbad, Calif.). A second round of PCR was performed using fusion primers that incorporated the 'A' and B' 454 pyrosequencing adapters onto the 5' ends of the TX9/1391 primers, respectively. The forward fusion primer also included variable length barcodes that enabled multiplexing multiple samples into a single 454 sequencing run. These amplicons were PAGE purified and quantitated prior to combining into one composite library. The resulting library was sequenced using the standard 454 Life Sciences Lib-L emulsion PCR protocol and Titanium chemistry sequencing (Margulies, Egholm et al. 2005). Sequences that passed the instrument QC filters were also subjected to additional filters that required all bases be Q20 or higher and the average of all bases in any read to be Q25 or greater. Furthermore, the TX9 primer was trimmed off of the 5' end and the sequences were trimmed on the 3' end at a conserved site distal to the V6 region (ca position 1067, *E. coli* numbering). The final sequences were approximately 250 bp in length and included the V5 and V6 regions.

Figure 23:
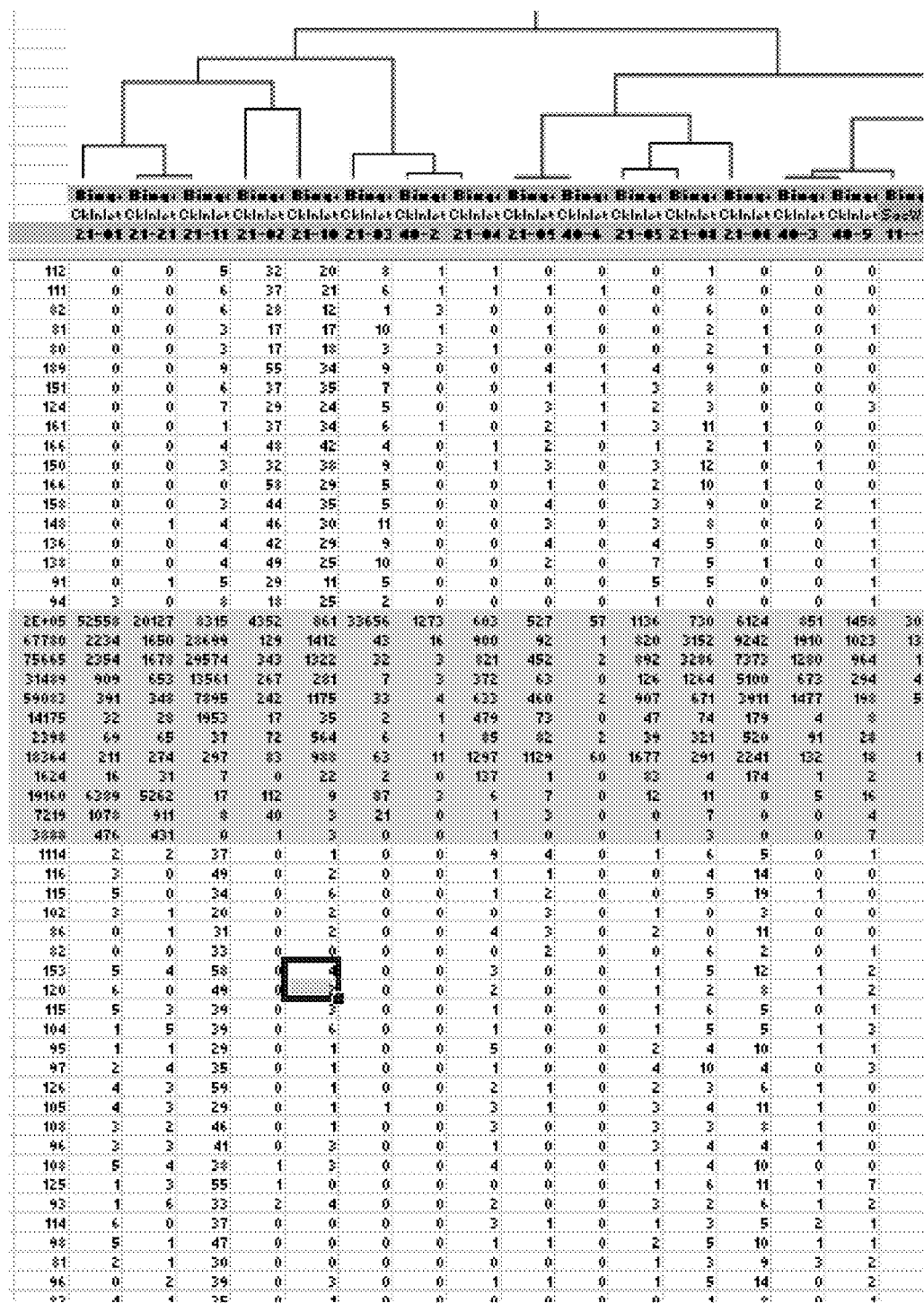
FIG. 23: illustrates a Two-dimensional cluster analysis of 16S rRNA genes from biogenic gas samples. The numerical values in each cell of the array represent the number of times a specific 16S rRNA gene sequence was identified in that sample. The values in the first column are the sum of the occurrences of each sequence in all samples (Note, this view is truncated and does not include all of the samples or all of the sequences identified). Each column in the array represents a single sample. Each row in the array is a unique 16S rRNA gene sequence which serves as a proxy for a unique microbe. The columns are rearranged (clustered) according to the microbial community present in that sample such that samples with similar microbial communities are grouped together. The rows are clustered according to the abundance distribution of each sequence across the samples. Thus, sequences with similar distributions are grouped.

The sequence abundance data was log transformed and clustered using Pearson correlation as the distance metric and Ward's method for hierarchical clustering. The clustering was performed using the software program PC-ORD. Inspection of the data revealed the organization of sequences into groups with one particular group showing a strong association with biogenic gas samples (FIG. 23). This presumptive consortium was comprised of 12 distinct sequences derived from three genera including *Acetobacterium*, *Bacteroidetes* and *Spirochaetes*. This consortium was labeled Consort-ABS1. The 12 sequences (the so-called "Consort-ABS1") are:

SEQ ID NO: 1, Acetobacterium
CACGCCGTAAACGATGAGTGCTAGGTGTTGGGGAGACTCAGTGCCGCAGC
TAACGCAATAAGCACTCCGCCTGGGGAGTACGACCGCAAGGTTGAAACTC
AAAGGAATTGACGGGGACCCGCACAAGCAGCGGAGCATGTGGTTTAATTC
GAAGCAACGCGAAGAACCTTACCAGGTCTTGACATCCTCTGACAATCTGA
GAGATCAGACTTTCCCTTCGGGGACAGAGAGACAGGTGGTGC SEQ ID NO: 2, Acetobacterium
CACGCCGTAAACGATGAGTGCTAGGTGTTGGGGAGACTCAGTGCCGCAGC
TAACGCAATAAGCACTCCGCCTGGGGAGTACGACCGCAAGGTTGAAACTC
AAAGGAATTGACGGGGACCCGCACAAGCAGCGGAGCATGTGGTTTAATTC
GAAGCAACGCGAAGAACCTTACCAGGTCTTGACATCCTCTGACAACCCAA
GAGATTGGGCTTTCCCTTCGGGGACAGAGAGACAGGTGGTGC SEQ ID NO: 3, Acetobacterium
CACGCCGTAAACGATGAGTGCTAGGTGTTGGGGAGACTCAGTGCCGCAGC
TAACGCAATAAGCACTCCGCCTGGGGAGTACGACCGCAAGGTTGAAACTC
AAAGGAATTGACGGGGACCCGCACAAGCAGCGGAGCATGTGGTTTAATTC
GAAGCAACGCGAAGAACCTTACCAGGTCTTGACATCCTCTGACAATCTGA
GAGATCAGACTTTTCCTTCGGGAACAGAGAGACAGGTGGTGC SEQ ID NO: 4, Acetobacterium
CACGCCGTAAACGATGAGTGCTAGGTGTTGGGGAGACTCAGTGCCGCAGC
TAACGCAATAAGCACTCCGCCTGGGGAGTACGACCGCAAGGTTGAAACTC
AAAGGAATTGACGGGGACCCGCACAAGCAGCGGAGCATGTGGTTTAATTC
GAAGCAACGCGAAGAACCTTACCAGGTCTTGACATCCTCTGACCATCTGA
GAGATCAGACTTTTCCTTCGGGAACAGAGAGACAGGTGGTGC SEQ ID NO: 5, Acetobacterium
CACGCCGTAAACGATGAGTGCTAGGTGTTGGGGAGACTCAGTGCCGCAGC
TAACGCAATAAGCACTCCGCCTGGGGAGTACGACCGCAAGGTTGAAACTC
AAAGGAATTGACGGGGACCCGCACAAGCAGCGGAGCATGTGGTTTAATTC
GAAGCAACGCGAAGAACCTTACCAGGTCTTGACATCCTCTGACCATCTGA
GAGATCAGACTTTCCCTTCGGGGACAGAGAGACAGGTGGTGC SEQ ID NO: 6, Acetobacterium
CACGCCGTAAACGATGAGTGCTAGGTGTTGGGGAGACTCAGTGCCGCAGC
TAACGCAATAAGCACTCCGCCTGGGGAGTACGACCGCAAGGTTGAAACTC
AAAGGAATTGACGGGGACCCGCACAAGCAGCGGAGCATGTGGTTTAATTC
GAAGCAACGCGAAGAACCTTACCAGGTCTTGACATCCTCTGACCACCCAA
GAGATTGGGCTTTCCCTTCGGGGACAGAGAGACAGGTGGTGC SEQ ID NO: 7, Acetobacterium
CACGCCGTAAACGATGAGTGCTAGGTGTTGGGGAGACTCAGTGCCGCAGC
TAACGCAATAAGCACTCCGCCTGGGGAGTACGACCGCAAGGTTGAAACTC
AAAGGAATTGACGGGGACCCGCACAAGCAGCGGAGCATGTGGTTTAATTC
GAAGCAACGCGAAGAACCTTACCAGGTCTTGACATCCTCTGACAATCCAA
GAGATTGGGCTTTCCCTTCGGGGACAGAGAGACAGGTGGTGC SEQ ID NO: 8, Bacteroides
CACGCAGTAAACGATGATTACTAGCTGTTTGCGATACAATGTAAGCGGCT
GAGCGAAAGCGTTAAGTAATCCACCTGGGGAGTACGTTCGCAAGAATGAA -continued

ACTCAAAGGAATTGACGGGGGCCCGCACAAGCGGAGGAACATGTGGTTTA

ATTCGATGATACGCGAGGAACCTTACCCGGGCTTGAAATGCATCTGACCG

GCCTTGAAAGAGGTTTTCCCTTCGGGGCAGATGTGTAGGTGCTGC

SEQ ID NO: 9, Spirochaetes
CGCACAGTAAACGATGTGCACCAGGTGGCGGGGGTAGAACCCCCGGTACC

GTAGCAAACGCATTAAGTGCACCGCCTGGGGAGTATGCTCGCAAGGGTGA

AACTCAAAGGAATTGACGGGGCCCGCACAAGCGGTGGAGCATGTGGTTT

AATTCGATGGTACGCGAGAAACCTTACCAGGGCTTGACATACACCGGAAG

CGCCGTGAAAGCGGCGTGCCGCTTGCGGCCGGTGAACAGGTGCTGC

SEQ ID NO: 10, Bacteroides
CACACAGTAAACGATGAATACTCGCTGTTTGCGATATACAGTAAGCGGCC

AAGCGAAAGCATTAAGTATTCCACCTGGGGAGTACGCCGGCAACGGTGAA

ACTCAAAGGAATTGACGGGGGCCCGCACAAGCGGAGGAACATGTGGTTTA

ATTCGATGATACGCGAGGAACCTTACCCGGGCTTGAATTGCAGAGGAACA

TAGTTGAAAGATTATGGCCGCAAGGTCTCTGTGAAGGTGCTGC

SEQ ID NO: 11, Bacteroides
CACACAGTAAACGATGAATACTCGCTGTTTGCGATATACAGTAAGCGGCC

AAGCGAAAGCATTAAGTATTCCACCTGGGGAGTACGCCGGCAACGGTGAA

ACTCAAAGGAATTGACGGGGGCCCGCACAAGCGGAGGAACATGTGGTTTA

ATTCGATGATACGCGAGGAACCTTACCCGGGCTTGAATTGCAGAGGAATA

TAGTTGAAAGATTATCGCCGCAAGGTCTCTGTGAAGGTGCTGC

SEQ ID NO: 12, Bacteroides
CACACAGTAAACGATGAATACTCGCTGTTTGCGATATACAGTAAGCGGCC

AAGCGAAAGCATTAAGTATTCCACCTGGGGAGTACGCCGGCAACGGTGAA

ACTCAAAGGAATTGACGGGGGCCCGCACAAGCGGAGGAACATGTGGTTTA

ATTCGATGATACGCGAGGAACCTTACCCGGGCTTGAATTGCAGAGGAATA

TAGTTGAAAGATTATAGCCGCAAGGTCTCTGTGAAGGTGCTGC.

To test whether Consort-ABS1 was capable of enhancing the rate of conversion of coal to methane, the consortium was assembled from colony purified isolates present in an in-house strain collection. The 12 16S rRNA gene sequences identified from the 454 sequence data that comprised the Consort-ABS1 consortium had 45 matches from the C600 strain collection with 100% identity and 100% coverage (Table 3). The strain ID numbers comprised: 314, 316, 323, 325, 331, 339, 357, 362, 368, 372, 386, 393, 462, 485, 557, 561, 571, 587, 591, 646, 649, 650, 661, 662, 669, 674, 675, 677, 679, 680, 682, 684, 686, 694, 696, 711, 712, 714, 717, 722, 724, 726, 733, 734, 741. According to one aspect of the invention, nucleic acid oligomers for the 16S rRNA gene, including primers with nucleotide sequences including SEQ ID NO. 1, 2, 3, 4, 5, 6, 7, 8, 9, 10, 11, or 12, may be used to identify strains in a consortium.

TABLE 3

Strain information from members of the Consort-ABS1 synthetic consortium

| C600 Strain | 454 V5V6 | Genus | SEQ ID NO |
|---|---|---|---|
| 368, 372, 646 | TXv5v6-0101700 | Acetobacterium | 1 |
| 650, 674, 722 | TXv5v6-0101090 | Acetobacterium | 2 |
| 316, 331, 325, 362, 537, 649 | TXv5v6-0101840 | Acetobacterium | 3 |
| 684, 714, 724 | TXv5v6-0102484 | Acetobacterium | 4 |
| 675, 679, 680 | TXv5v6-0102389 | Acetobacterium | 5 |
| 650, 674, 722 | TXv5v6-0102156 | Acetobacterium | 6 |
| 339, 357, 650, 674, 722 | TXv5v6-0101312 | Acetobacterium | 7 |
| 677 | TXv5v6-0028456 | Bacteroidetes | 8 |
| 314, 325, 557, 561, 571, 587, 591, 662, 686, 694, 696, 712, 733, 734 | TXv5v6-0005632 | Bacteroidetes | 12 |
| 661, 682, 711, 714, 717, 741 | TXv5v6-0005526 | Bacteroidetes | 10 |
| 323, 462, 669, 726 | TXv5v6-0005680 | Bacteroidetes | 11 |
| 485, 393, 386 | TXv5v6-0239816 | Spirochaetes | 9 |

Each of these strains was thawed from the strain library (stored at −80° C.), and patched out in an anaerobic chamber onto the following medium plate types:

Strains 571, 587, 591, 717, 722, 724, 726, 733, 734, and 741 on Anaerobic Agar;

Strains 314, 316, 323, 325, 331, 339, 357, 362, 462, 485, 646, 649, 650, 661, 662, 674, 675, 677, 679, 680, 682, 684, and 686 on *Brucella* Blood Agar Strains 368, 372, 386, 393, 537, 557, 561, 694, 696, 711, 712, and 714 on Tryptic Soy Agarose.

After 14 days of growth on solid media, the patches were picked in an anaerobic chamber and transferred to liquid media: Anaerobic Broth, *Brucella* Broth, and Tryptic Soy Broth. After 20 days of growth, a Consortium mixture was prepared by pipetting 300 μl of each strain into a sterile anaerobic conical, producing 9 ml of mixture. To this mix, 9 ml of a 2× freezing medium was added: 2×*Brucella* Broth, 30% glycerol, 0.05% sodium sulfide. The mix was then frozen at −80° C. for storage.

On the day of Sand Pack inoculation, 4 ml of the Consortium mixture was thawed and then washed via centrifugation to remove any residual freezing medium by centrifuging the mixture at 4° C., at 201×g for 20 minutes followed by removing and discarding the supernatant. The pellet was resuspended in 1 ml of production water by inverting several times. This preparation served as the inoculum for the Consort-ABS1 addition in the sandpack experiment.

Sandpack tubes were set up to test the effect of a synthetic consortium (Consort-ABS1) on the coal to methane conversion rate in gas well production water incubated with coal and other endogenous potential subsurface substrates comprising sandstone with organic debris and volcanic ash. This experiment would in effect be supplementing the native microbes present in the production water with the Consort-ABS1 consortium. Since Consort-ABS1 did not contain a methanogen a source of methylotrophic methanogens (*Methanolobus* sp.) was included in the experiment.

Approximately 17.8 g of U.S. Silica Company's ASTM graded sand was added to a sterile 15 ml polypropylene conical tube (22.88 g was added to each no carbon substrate controls). Approximately 0.167 g of each carbon substrate mixture (coal, volcanic ash, and sandstone with organic debris) were weighed out and added to the sand in each conical tube. To create the carbon substrate mixtures, coal, volcanic ash and organic debris each of which had been obtained from four different Cook Inlet core samples were combined. Each conical tube was vortexed for 10 sec to homogenize the carbon and sand mixture. Additional 3.5 g aliquots of sand were weighed into weigh paper packets for each of the conical tubes.

All conical tubes with the carbon and sand mixtures (as well as the all sand controls), the packets of sand, and 18×150 mm glass Balch tubes (Bellco No. 2048-00150) that were previously washed with Sparkleen 1, rinsed with deionized water and dried were brought into an anaerobic chamber filled with 5% $H_2$, and % $CO_2$, balanced with $N_2$. The caps to the conical tubes were unscrewed and loosely replaced in the chamber to allow gas exchange. These materials remained in the chamber for at least two days before assembly.

To assemble the sand pack tubes, each carbon and sand mixture was gently poured into a test tube in the chamber and an aliquot of sand was added to the top to create a top layer (approximately 1" height) with no carbon substrate. Each tube was capped with a rubber stopper, over which a metal cap was crimped. The assembled tubes were autoclaved on fast exhaust for 20 minutes and immediately brought back into the anaerobic chamber.

Sand Pack2—Cell Additions:

To maintain the same concentration of nutrient additions between all cell addition treatments, 45.5 ml of the standard nutrient additions solution described previously was mixed with 154.5 ml of sterile (0.2 um filtered) production water (40-3) for a final volume of 200 ml. The standard nutrient mix was assembled such that the final concentrations in the sandpack incubations would be: sodium phosphate, pH 7.5, 7.8 mM; NaCl—KCl, 100 mM; $NH_4Cl$, 5.6 mM; $MgCl_2$, 2 mM; and 1× trace metals and vitamin solution. Three sand pack tubes (with carbon substrates) were inoculated as no cell blanks with 5.5 ml each of only this mixture using the same method previously described. The remaining 183.5 ml of the production water and nutrient mixture was inoculated with 1.22 ml of cells (40-3) thawed anaerobically from frozen stock (previously stored at −80° C.) for a 150× cell dilution. Three sand pack tubes with carbon substrates and three tubes with only sand (no carbon) were inoculated with this production water with nutrients and endogenous cells (40-3).

The remaining inoculated production water with nutrients was split into seven aliquots of 17.5 ml each in sterile 50 ml conical tubes. Additional cells from different sources were added to each conical tube to create the various cell addition treatment inocula. To remove any freezing media, frozen stocks (−80° C.) of cell addition types were spun at 3000×g for 20 min. The supernatant was removed, and the cells were anaerobically resuspended in 1 ml of sterile (0.2 um filtered) production water (40-3). Cell additions grown in antibiotics were also washed and anaerobically resuspended in sterile production water. A 250 µl aliquot of the resuspended cells were removed and loaded into a 96 well plate. OD readings of each cell addition type (including the endogenous cells, 40-3) were taken at 550 nm on a Biotek Epoch plate reader. The volume of cells to add to each 17.5 ml aliquot was determined based on their OD reading using the following formula:

$$\frac{2 * OD(21-6) * 0.12 \text{ ml}}{OD(\text{cell addition})}$$

where 0.12 ml is the volume of the endogenous cells added per 17.5 ml aliquot (150× dilution). Based on the OD readings, the following volumes of resuspended cells were added to each 17.5 ml treatment aliquot, and inverted to mix:

| | |
|---|---|
| 'No Cell Additions': | None |
| 'Methanogens Only': | 0.14 ml Mgen1 and 0.23 ml Mgen2 |
| 'Consort-ABS1 + Methanogen' | 0.7 ml Consort-ABS1 and 0.14 ml Mgen1 and 0.23 Mgen2 |

Three sand pack tubes (with carbon substrates) were inoculated for each cell addition treatment using a venting method. In an anaerobic chamber, the tubes were opened and a 6" sterile spinal needle was gently pushed through the sand mixture to the bottom with its plug inside. The plug was removed, leaving the needle in the sand as a vent and 5.5 ml of the corresponding cell addition inocula mixture was added to the top of the sand with a 5 ml serological pipet. The liquid inocula slowly saturated the sand mixture from the top until it reached the bottom. Once saturated, the needle was slowly removed, leaving a thin layer of liquid at the top of the sand. The same needle was used for each replicate within a cell treatment. Once inoculated, the tubes were capped and crimped, the headspaces were replaced, and they were stored at 20° C. as previously described.

Description of Cell Additions

I. 40-3 are cells that are endogenous to the production water used in the sand pack experiments. The cells were isolated by centrifuging the production water, anaerobically, at 3000×g for 22 minutes at 4° C. The supernatant was removed and the cells were resuspended in standard freezing medium containing *Brucella* broth, 0.05% sodium sulfide, and 15% glycerol. They were then stored at (−80° C.) until needed.

II. Mgen1 is an enrichment culture that was cultured from production water from Beluga well (40-6). The previously frozen cells were inoculated into methanogen enrichment medium, MEM+trimethylamine+16 g/L NaCl, sodium sulfide, and antibiotics (vancomycin, streptomycin, kanamycin, penicillin G) and incubated for several months before it was determined that the culture was making methane. It has been sequenced using 454 sequencing technology and shown to contain a high proportion of *Methanolobus*. It was frozen until needed.

III. Mgen2 is a highly purified methanogen culture (that contains more than one species) derived from production water 40-3. The previously frozen cells from this Beluga well were inoculated into MEM+peptone+sodium acetate+methanol+trimethylamine+sodium formate+antibiotics (kanamycin, vancomycin, ampicillin)+sodium sulfide, and the culture in the serum vial was given a hydrogen overpressure. After a month the culture was shown to produce methane. An aliquot was then placed in a "Gellan Roll Vial" in order to isolate single colonies. The composition of the gellan roll vial was the same as the liquid culture except that no antibiotics were used and the gelling agent added was 0.7% gellan. A single colony was plucked from the vial after incubation for one month and it was resuspended in liquid medium of the same composition as described above. After two weeks this highly purified culture was shown to produce methane. This culture was used directly in the sand packs.

IV. Consort-ABS1: 12 sequences were identified from the 454 sequence data as clustering across multiple samples from biogenic gas wells when sorted by abundance, and were therefore selected as candidates for a Consortium mixture.

Figure 24:
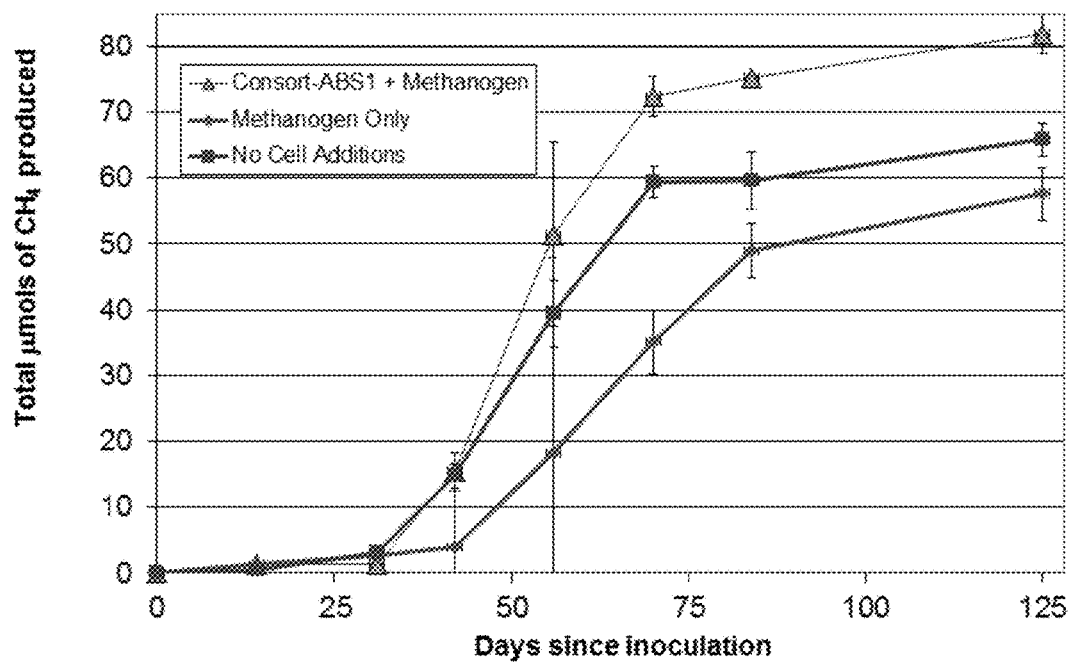
FIG. 24: graphically illustrates Methane production in sandpacks incubations supplemented with additional cells including the exemplary "Consort-ABS1" composition of the invention.

At various time points during incubation of the sand pack tubes, a portion of the headspace was removed to determine the amount of gas produced using a pressure transducer. The amount of methane produced was determined by gas chromatography analysis of headspace samples including a correction for the total volume of gas produced. The rate of conversion of coal to methane began to increase at 42 days in the Consort-ABS1 plus Methanogen and the No Cell Addition sand pack incubations (FIG. 24). Interestingly, incubations supplemented with Methanogens alone appeared to detract from the methanogenic rate. The highest coal to methane rates from any of the conditions tested were observed in the Consort-ABS1 plus Methanogens from 70 days onward and these differences were statistically significant.

Example 5

Figure 10:
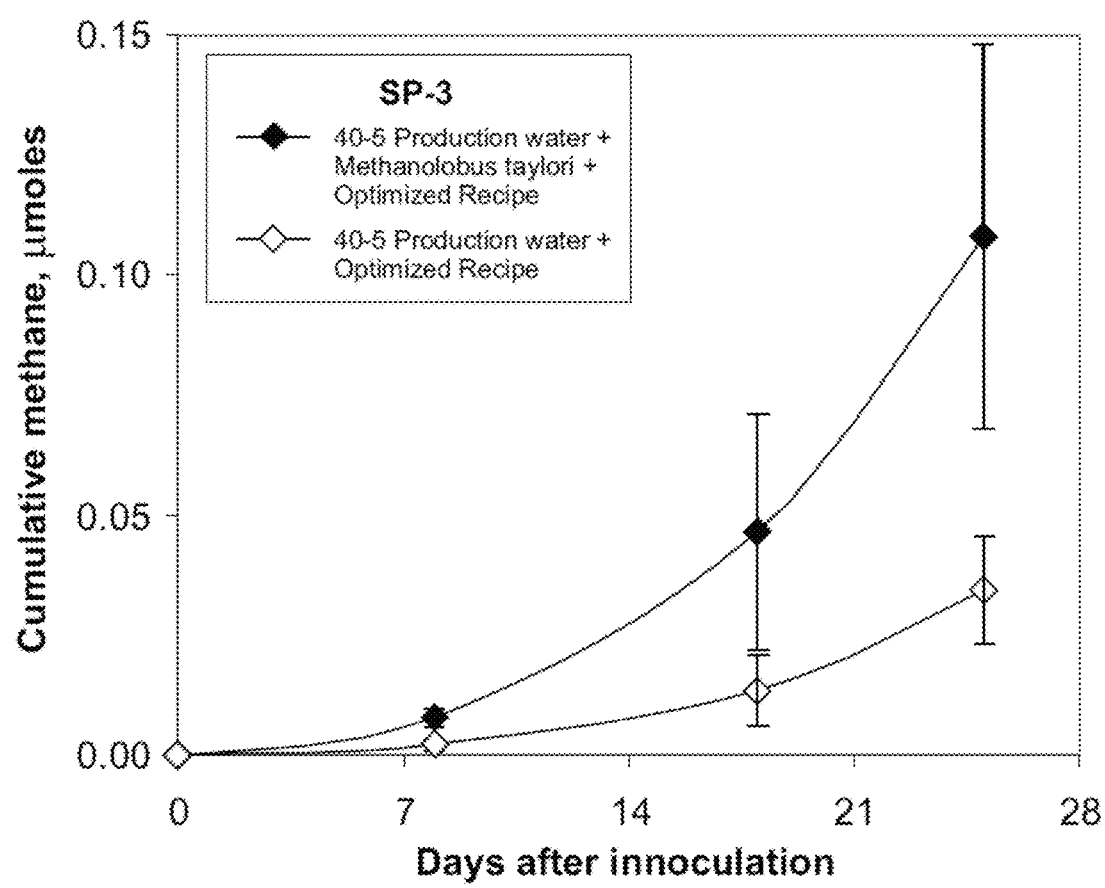
FIG. 10: graphically illustrates Introduction of a pure *Methanolobus* taylorii culture increases methane production in model sand pack incubations. Each data point represents a triplicate set of sand pack tubes.

Creating Injectates Comprised of Microbes Capable of Enhanced Methanogenic Degradation of Organic Substrates Microbial consortia derived from target (Cook Inlet) production water were selectively enriched with specific chemical compounds which are analogues to target subsurface organic matter (FIG. 10). This method allows relatively rapid growth of biomass in microbial consortia that could be re-injected, e.g. with the optimized nutrient mix. The coal/lignin-degrading consortium was derived from target gas field production water, and is composed of microorganisms that were enriched on lignin (SIGMA-ALDRICH), lignin monomers, and Cook Inlet gas field coal. The lignin monomers that were tested were: ferulic acid, tannic acid, quinic acid, and shikimic acid, which are representative compounds typical to low maturity coals, e.g., Beluga and Sterling formation organic matter thermal maturity averages at 0.33% of $R_0$.

To obtain the consortia used for inoculation into sand pack tubes, enrichment cultures were established previously, assayed for pressure and methane production, passaged into medium of the same composition, and then frozen at $-80°$ C. To prepare the parent cultures the lignin and lignin-like compounds were added to RAMM-Fresh medium (Shelton and Tiedje 1984) along with a mixture of coals. Final concentration for all lignin and lignin-like compounds combined was 50 mg/L. The seven rock types, originating from target basins were ground together using a mortar and pestle, and 0.9 g of the mixture was allocated anaerobically into each vial of RAMM-F. Production water (3-4 mL) from target sites, which had been kept anaerobic, was inoculated into the vials, and a nitrogen headspace was provided. The vials were incubated in the dark, shaking, at room temperature for several months. During the incubation the headspace gases were assayed and the production water-consortia that produced high volumes of methane gas were noted. These corresponded to the same production waters used in the sand pack experiments described herein. Aliquots of these cultures were inoculated into fresh medium of the same composition to obtain P1 cultures. These cultures were then incubated and monitored as described above. Frozen aliquots of the parent (P0) and passaged (P1) cultures were obtained by mixing the liquid cultures with 2× freezing medium (30% glycerol, 2×RAMM-F). The coal-degrading consortia used in the sand pack tubes was a frozen P1 aliquot (2 mL) that was thawed, and then added to RAMM-F medium, washed once, and resuspended in production water. The coal from the original coal/lignin enrichment was not removed. The amount of cells added was indeterminate.

Target Basin Production Water

Target basin (California) production water was collected and kept anaerobic until used for sand pack experiments. The sand pack tubes were assembled exactly as described in Example 3 except that for these experiments, California production water and endogenous microbes were amended with standard optimized nutrients at the concentrations described in Table 2. Cook Inlet coal/volcanic ash/sandstone with organic debris was used in these sand pack tubes. The coal-lignin consortium derived from Cook Inlet 40-5 production water, as described in Example 4, was added to enhance methanogenesis rate (FIG. 10b).

Identification of methanol-utilizing methanogenesis or "methylotrophic" conversion, provided new routes to increased biogenic gas production. Identification of the dominant gas production pathway given the combination of microbial organisms, hydrocarbon substrate, and formation water chemistry allows for increased biogas production rates, better utilization of reservoir hydrocarbons, greater overall biogenic gas production and a longer life for biogenic gas reservoirs.

Example 6

Biogasification Risk Analysis

Figure 12A:
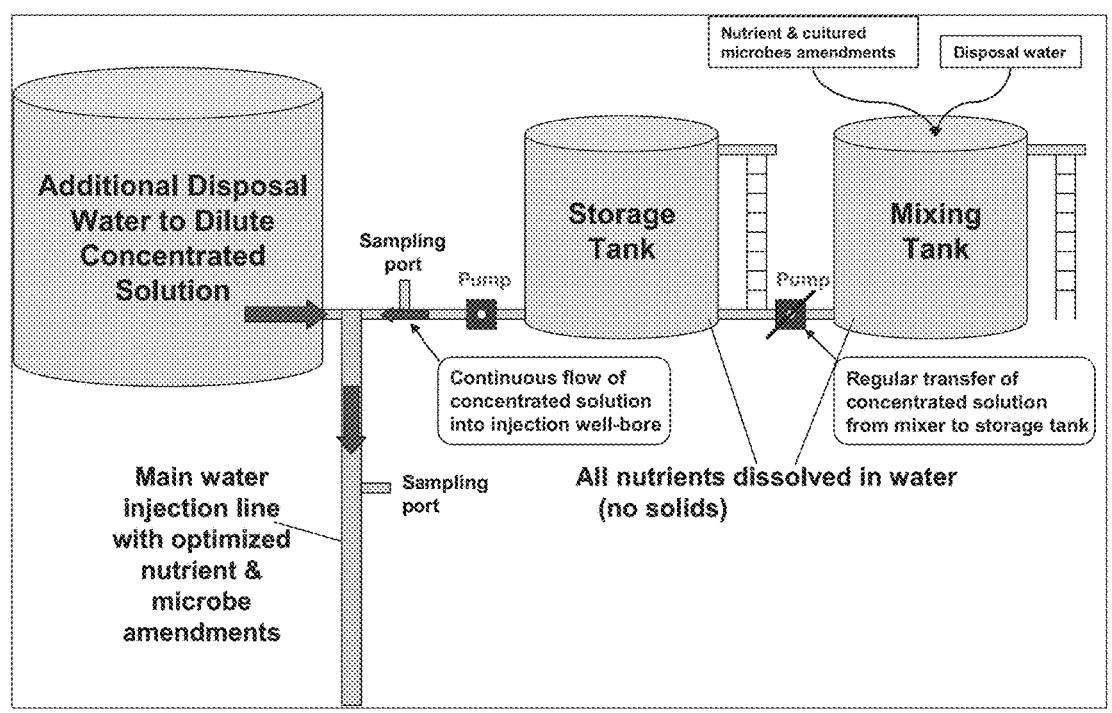
FIG. 12A and FIG. 12B: are Schematic representations of an exemplary method of the invention comprising nutrient and microbe injection in a field application.
Figure 12B:
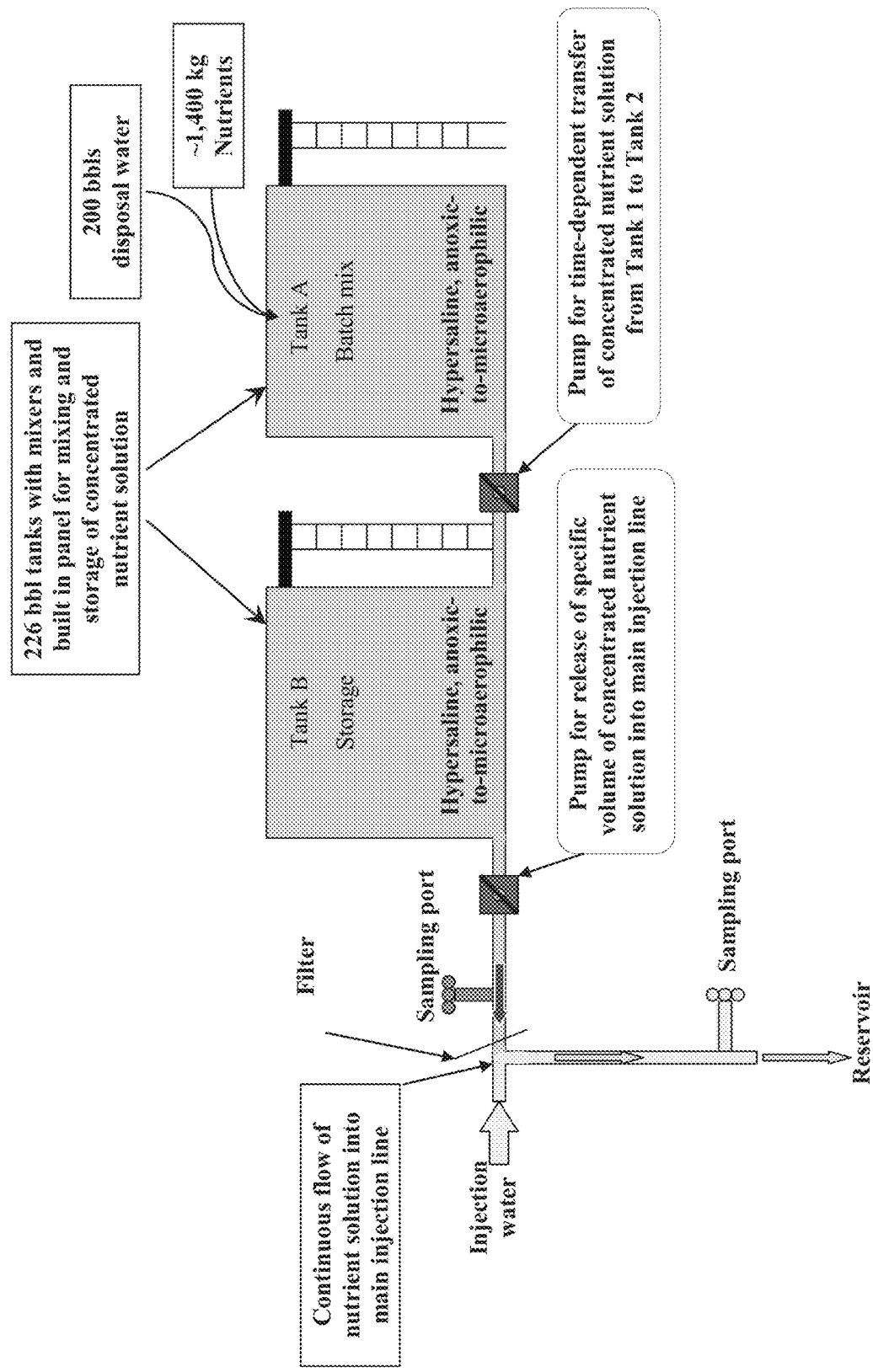
Figure 13:
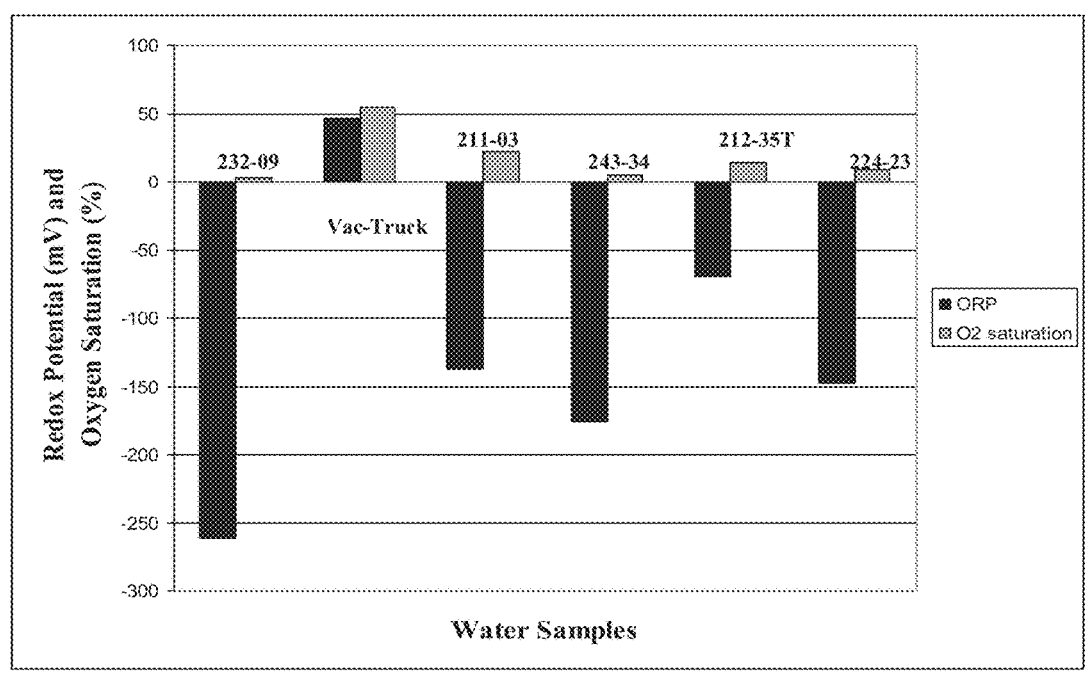
FIG. 13: graphically illustrates Field measurements of redox potential (black bars) and oxygen saturation (gray bars) of produced water from various producing wells and from the vacuum truck which collects water from all wells for disposal into injection well.
Figure 14A:
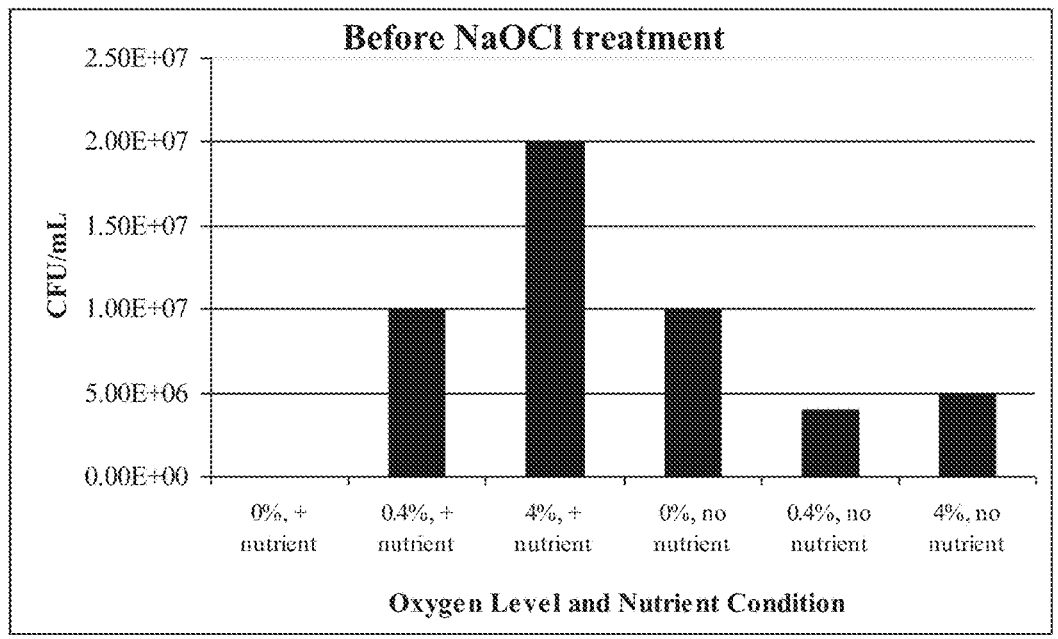
FIG. 14A and FIG. 14B: graphically illustrate Test results of effectiveness and concentration of sodium hypochlorite (NaOCl) required to control biomass formation in injection line and injection well-bore.
Figure 14B:
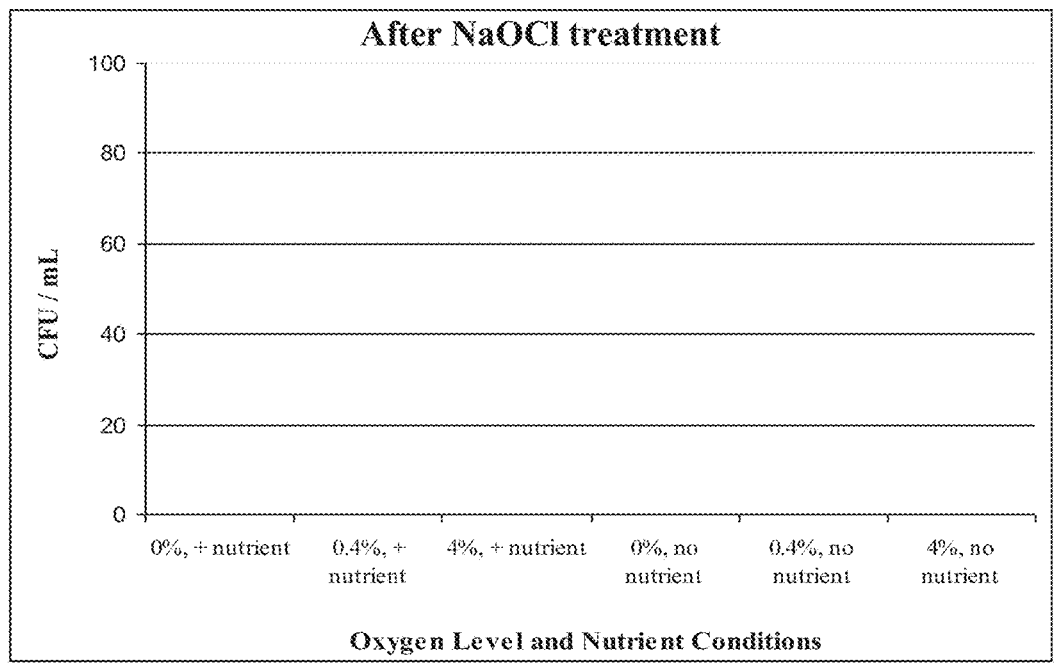
Figure 15A:
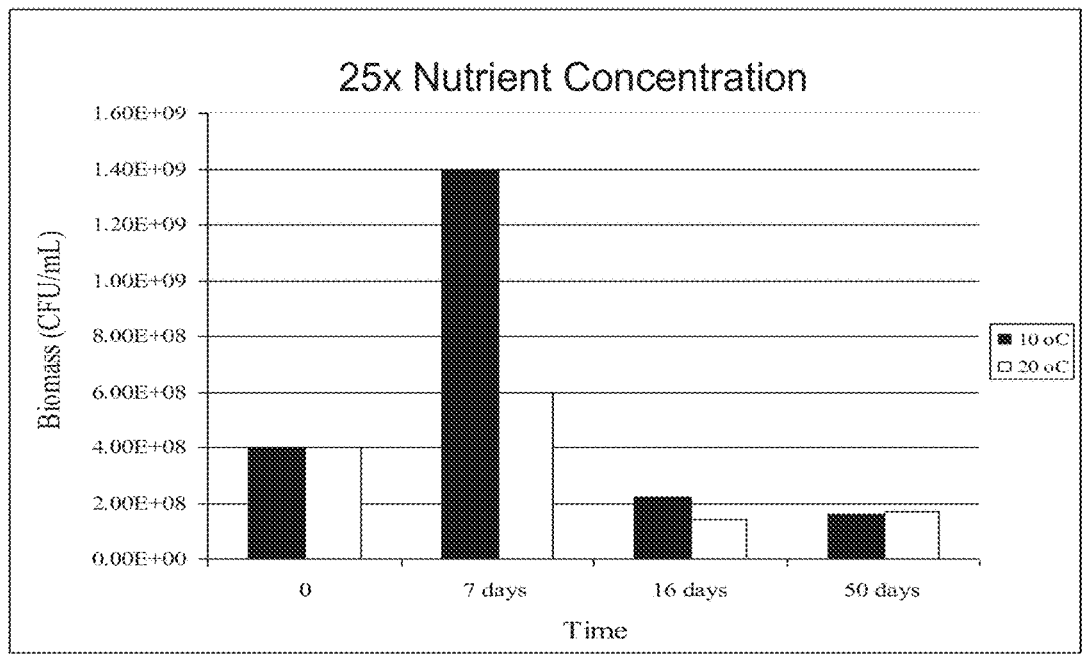
FIG. 15A and FIG. 15B: graphically illustrate Biomass development in an exemplary (1×) concentration nutrient recipe of the invention, and in an exemplary "excess (25×) concentration nutrient recipe" of the invention.
Figure 15B:
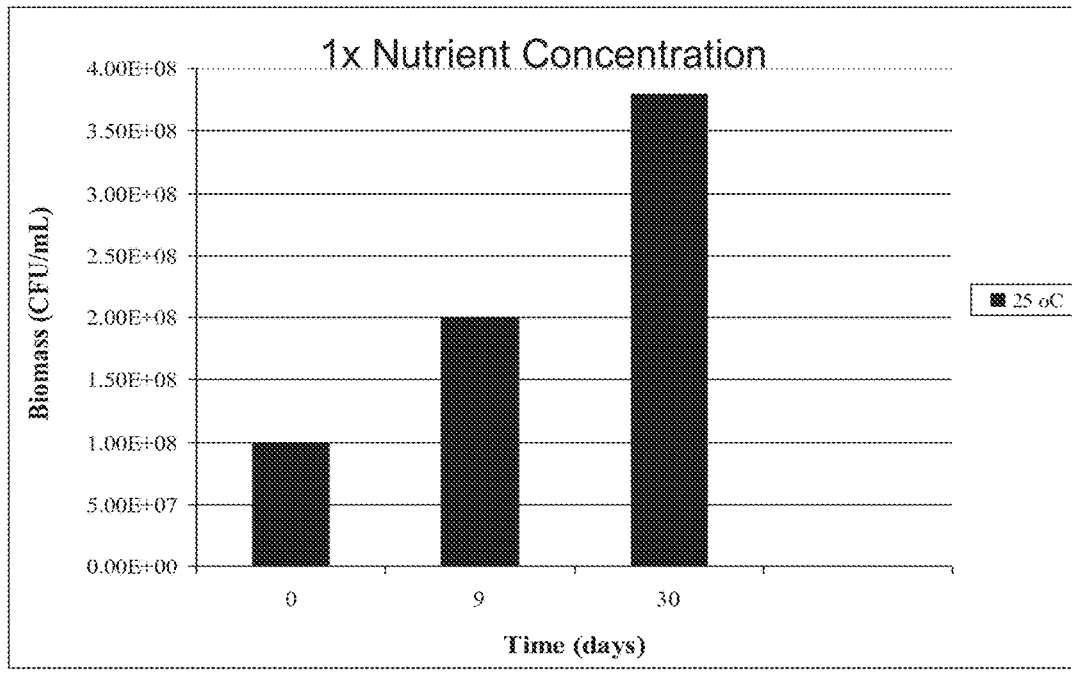

Applying a biogasification risk analysis process in the field (e.g. bioplugging and excess biomass development, oxygen-driven microbial corrosion in injection lines, biosludge development in injection tanks, inorganic scale formation, field-wide redox status of production/injection water, etc), was proposed in order to identify problems that could arise during field operations. A scheme for injection of the optimized nutrient recipe was also used to identify some of the potential problems (FIG. 12). The scheme is made up of 2 separate tanks (A and B). Tank A is to be used for mixing concentrated stock solution of the optimized nutrient recipe, while tank B is to be used for storing nutrient solution received from tank A. The scheme also includes ports for sample removal, and injection pumps to control flow of solutions exiting both tanks. According to the scheme, nutrient solution exiting tank B is to be mixed with injection water at appropriate ratio in order to achieve the desired concentration of nutrient components in the final mixture that is to be injected into the reservoir. Further, understanding of the travel length and the corresponding travel time of solution from the point of mixture to the point of entry into the reservoir helped clarify the likelihood of excess biomass formation, bioplugging, and oxygen-driven bio-corrosion along the injection line and in the well-bore. The potential for biological and inorganic sludge formation and accumulation in the mixing and storage tanks was evaluated. The tests carried out included chemical analysis of reagent samples, field-wide redox measurement; biomass control with sodium hypochlorite (NaOCl) solution; sludge treatment; as well as scale formation and modeling.

Figure 18:
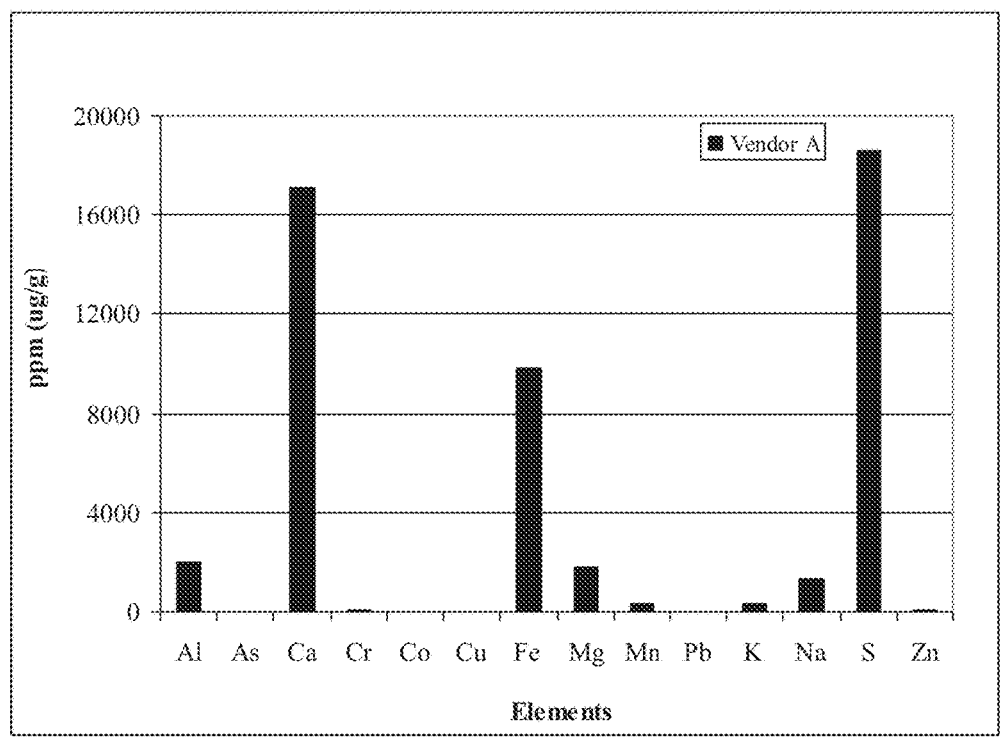
FIG. 18: graphically illustrates Level of trace compounds in monosodium phosphate from two different commercial vendors.
Figure 18:
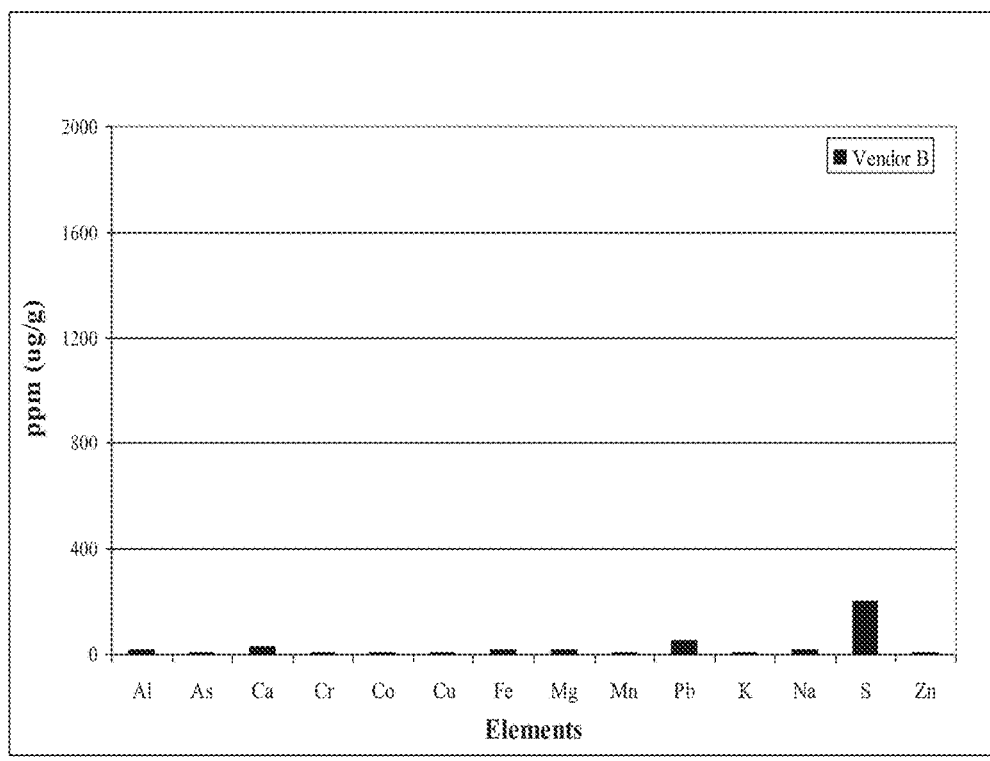

The purity of chemical reagents to be used for developing solution of nutrient recipe was confirmed by analyzing test samples of reagents that was obtained from selected commercial vendors. The analytical tests carried out include ion chromatography (IC), inductively coupled plasma mass spectrometry (ICP-MS), and inductively coupled plasma atomic emission spectroscopy (ICP-AES). The overall objective of the analysis is to determine the level of purity of the reagents, as well as identify level of certain elements (e.g. sulfur) in the reagents which may pose potential problems if introduced into the reservoir. This allows identification of the appropriate vendor supplying purer forms of the required chemical reagents (FIG. 18).

Figure 19:
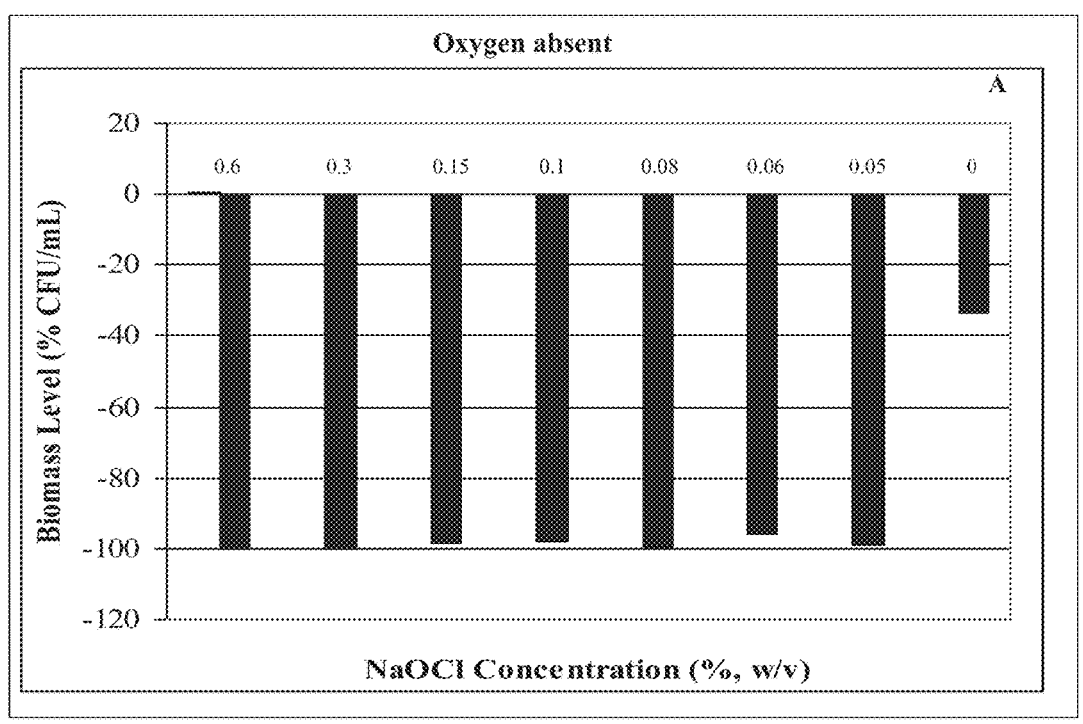
FIG. 19A and FIG. 19B: graphically illustrate the effect of NaOCl solution in absence (FIG. 19A) and presence (FIG. 19B) of oxygen on viability of microbial population. CFU/mL=Colony-forming units per milliliter.
Figure 19:
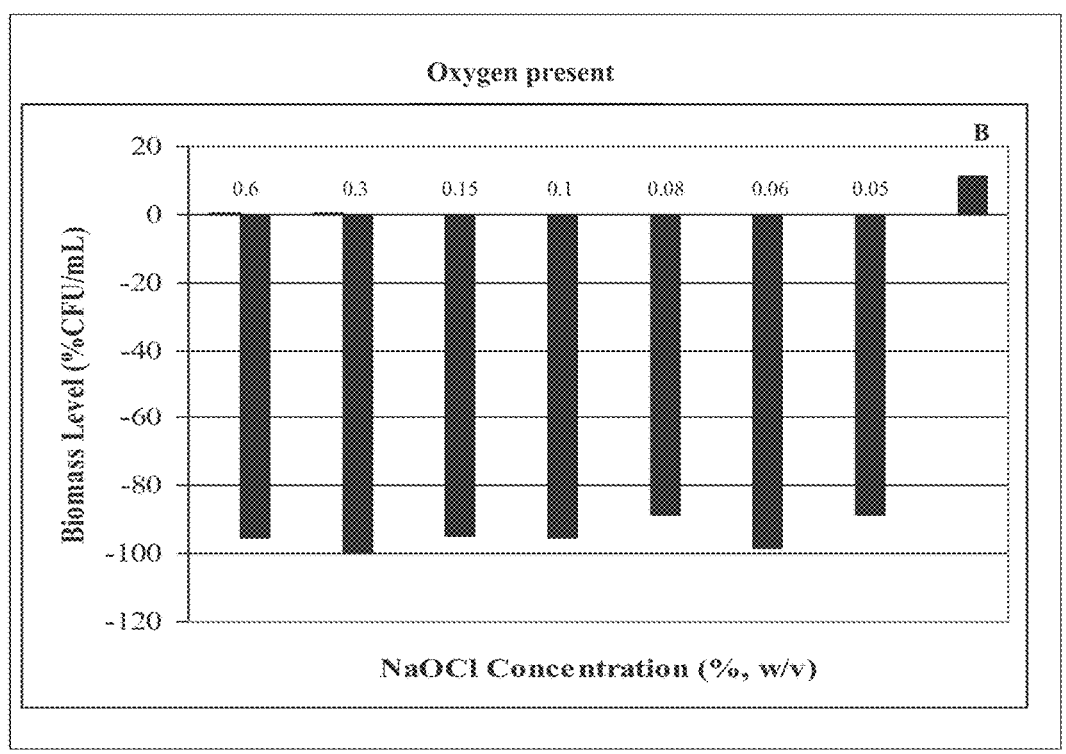

The procedures to test the effectiveness, and the minimum dose, of NaOCl that is required to eliminate biomass in the injection line and injection well-bore during the field biogasification process are the following. The initial population of microbes in production water, placed in tubes that were to be incubated under defined oxygen saturation conditions was determined either by direct counting of cells using a Petroff Hausser bacterial counting chamber, or by counting the colony forming units (CFU/mL) of microorganisms that developed on specialized media after incubation for specific period. The population of microbes that were present in the incubated tubes (also with added carbon source-coal and nutrient additions) was determined over time after methane was detected in the headspace of the tubes. Thereafter, the same tubes were amended with different concentrations (0.6%, 0.3%, 0.15%, 0.1%, 0.075%, 0.06%, 0.03% and 0%) of NaOCl solution followed by incubation of the tubes for 23 hours to allow the biomolecule-oxidizing action of the solution to come to appreciable completion. Immediately after this, the population of viable microbes (i.e. CFU/mL) in the NaOCl-amended tubes was determined by plating a specific volume of the culture on defined solid medium. All the concentrations of NaOCl solution that was tested were effective in inactivating microorganisms in the nutrient solution irrespective of the presence or absence of oxygen (FIG. 19A and FIG. 19B).

Figure 20:
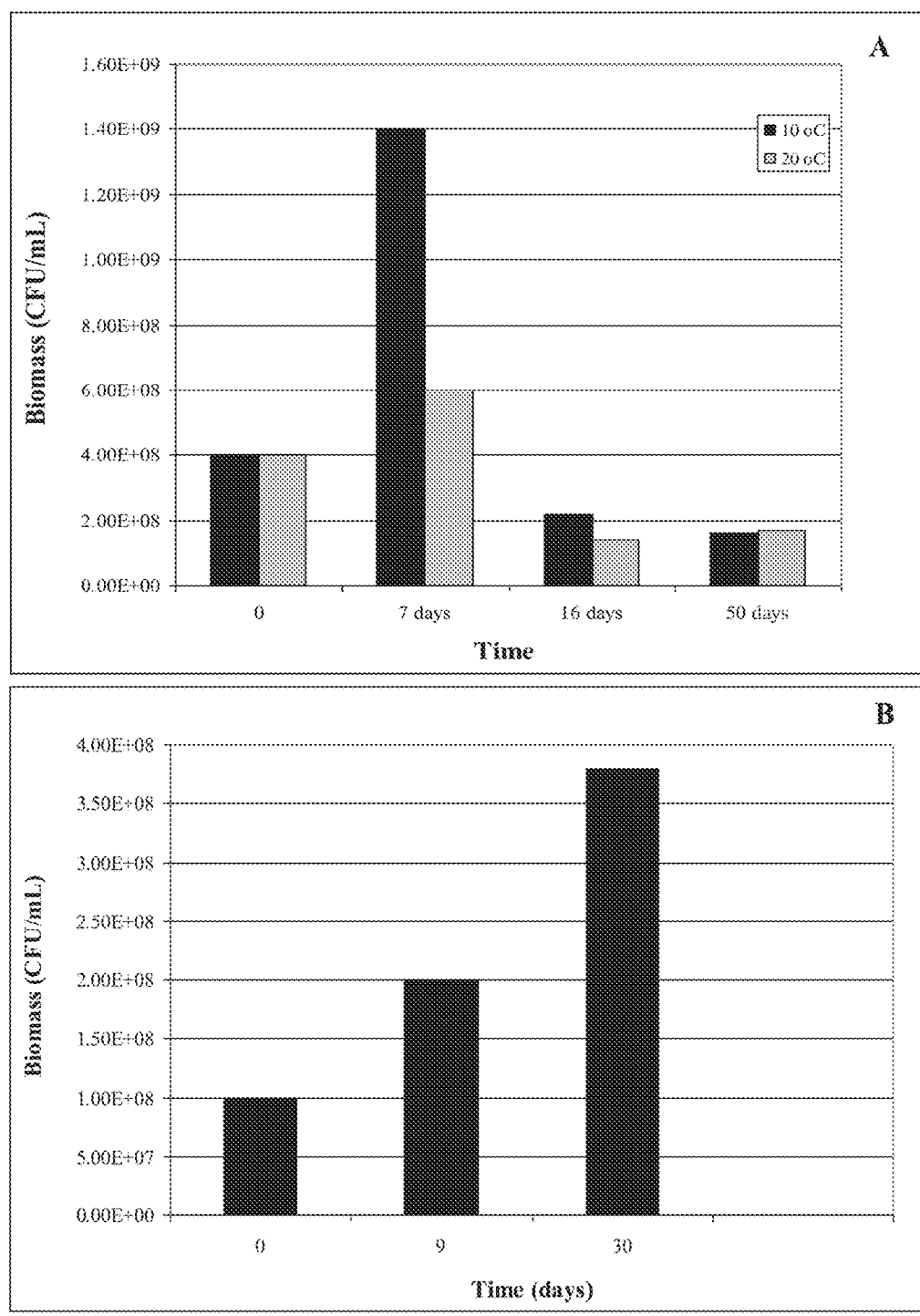
FIG. 20: graphically illustrates Development of biomass in (A) concentrated nutrient solution (25×) and (B) standard concentration of nutrient (1×). CFU/mL=Colony-forming units per milliliter.

The potential for biomass production and accumulation in nutrient solution in the mixing tank, storage tanks, and injection line was evaluated as follows. Production water was amended with specific concentrations of specially selected nutrients. To mimic the concentration to be used for the storage tanks, the production water was amended with excess concentration (i.e. 25×) of nutrients, while nutrients amended into production water at lower concentrations (1×) mimic the concentration of nutrients in solution entering the injection line. The nutrient-amended water was transferred into test tubes, and the initial population of microbes in the water in these tubes was determined. Thereafter, the tubes were incubated at 10, 20, or 25° C. for different periods (9 and 30 days for 1× concentration; 7, 16, and 28 and 50 days for 25× concentration) to allow growth of microbes and development of appropriate amount of biomass in the tubes if any. The population of microbes that developed after incubation was determined using the direct counting procedure (i.e. CFU/mL). Biomass levels dropped after 50 days of incubation in the concentrated 25× nutrient solution (FIG. 20) although there was an initial increase in biomass level after seven days. Biomass level in the 1× nutrients recipe increased over time (0-30 days), suggesting that the nutrient solution once in the injection line and injection well-bore may support the development of biomass in the zones.

Figure 21:
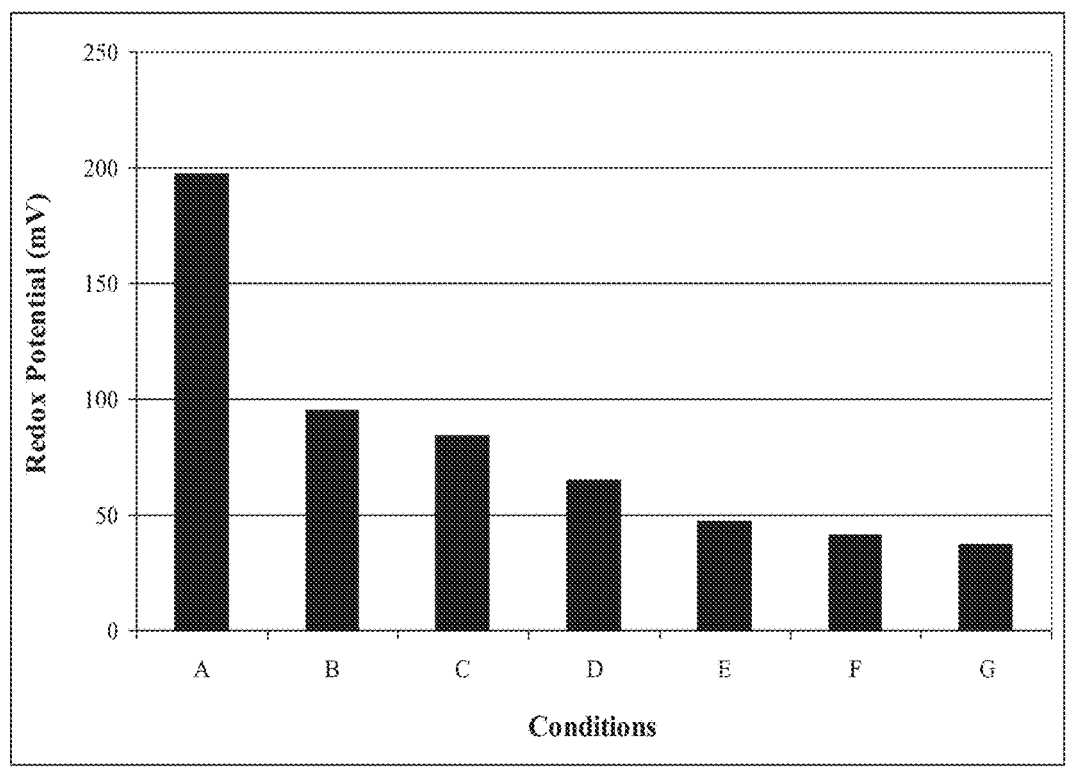
FIG. 21: graphically illustrates graphically illustrates Effect of oxygen-scavenging compounds on redox potential of produced water previously exposed to oxygen. mV=millivolts.

The effectiveness of any one or combination of compounds with an imine or quinone functional group to remove oxygen from oxygen-exposed production water was tested. The imine solutions may contain one or more imine oxygen scavengers including hydrazines, methylimines, ethylimines, propylimines, butylimines, diethylhydroxylamine (DEHA), alkeneimines like hydroxyalkylhydroxylamine, phenylenediamines, aminoguanidine, carbohydrazide, and the like. The quinone solutions may contain one or more quinone oxygen scavengers including hydroquinone, orthoquinone, semi quinone, pyrroloquinoline-quinone (PQQ), methylhydroquinone and the like. Other non-sulfur containing oxygen scavengers may also be used like aldehydes, carboxylic acids like acetic acid and tartronic acid, carbohydroxide, erythorbate, cobalts, methylethylketoxime (MEKO) and the like. The extent of oxygen removal was determined by measuring the change in redox potential of nutrient-amended (i.e. 1× concentration) production water that was previously exposed to atmospheric oxygen. The concentration of the oxygen scavenging compounds that was tested is shown in Table 4. The results from this test show that the compounds were effective in reducing oxygen saturation level in the produced water (FIG. 21A).

TABLE 4

Composition of produced water amended with two oxygen-scavenging compounds

| | Conditions | | | | | | |
|---|---|---|---|---|---|---|---|
| | A | B | C | D | E | F | G |
| Composition[a] | Water and nutrients | Water, nutrients, 34 mg of imine | Water, nutrients, 34 mg of imine + 1.9 mg of quinone | Water, nutrients, 68 mg of imine + 3.8 mg of quinone | Water, nutrients, 136 mg of imine + 7.4 mg of quinone | Water, nutrients, 170 mg of X + 9.3 mg of quinone | Water, nutrients, 204 mg of imine + 11.2 mg of quinone |

[a]Final concentration of imine and quinone in 1 L of aqueous nutrient solution.

Figure 22:
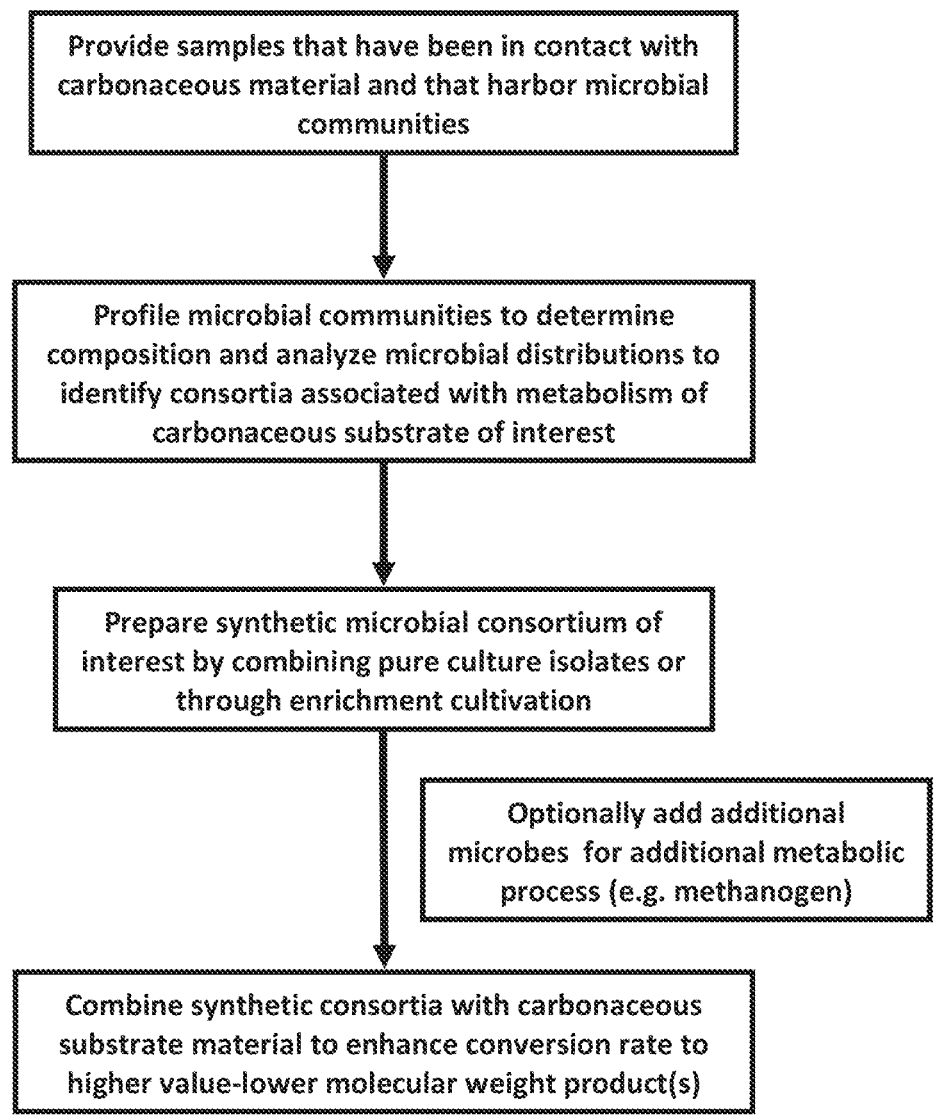
FIG. 22: is a Schema describing an exemplary method of the invention (or a method used to make a composition of the invention) comprising steps of finding, assembling and deploying a synthetic consortium of microbes.

Field measurement of redox potential (ORP) and oxygen saturation level, in produced water and injection water, determined if ORP and oxygen saturation level in the produced water and injection water vary in water obtained from wells or facilities across the field. Measurement was done using a YSI 6920 V2 sonde (YSI, Ohio, USA) which also allowed simultaneous evaluation of multiple parameters in water samples that were collected from the well-heads or water storage tanks directly. According to the information generated during the field sampling the ORP and oxygen saturation level vary across the field however water collected directly from the well-heads exhibits lower ORP and oxygen level in comparison to water collected from storage tanks receiving water from the respective wells. Water collected from vacuum trucks that are transferring produced water from producing wells to the injection well in the field had the highest ORP and oxygen level (FIG. 22 B).

The effectiveness of defined concentration of chemical reagents (NaOCl and acid) to act individually or complimentarily in dissolving sludge material that was collected from an on-site storage tank was determined by adding 10 mL of 6% NaOCl solution to ~2-3 g of sludge sample. This was then mixed by a vortex mixer for 30 sec. The mixture was then incubated at room temperature for 10, 30 or 60 min. Thereafter, the mixture was filtered through a pre-washed (using 10 mL of 6% NaOCl solution followed by 10 mL deionized water) and pre-weighed 50 µm filter. Then, 10 mL of deonized water was used to wash excess NaOCl solution. The filter and any residue that was left was then weighed. Alternatively, the filter with residue was exposed to 10 mL of 2N HCl for 10 minutes before filtration and washing with 10 mL deionized water. In all cases the amount of residue left on the filter after treatments was compared to the amount prior to treatment and the percent difference in weight was estimated (Table 5). Results show that NaOCl solution was very effective in dissolving sludge material and that treatment with acid (HCl solution) alone was not as effective. However, treatment of sludge with NaOCl prior to treatment with acid increased dissolution of the sludge materials, most likely due to increased accessibility of the inorganic particles that are trapped within the sludge to acid after NaOCl treatment.

TABLE 5

Effect of NaOCl solution and acid treatment on dissolution of tank derived sludge materials

| Incubation time (min) | Sludge Weight (g) | After NaOCl (Δg) | After NaOCl and HCl (Δg) | Total dissolved (%) |
|---|---|---|---|---|
| 10 | 2.52 | 0.331 | 0.293 | 88.4 |
| 30 | 2.26 | 0.174 | 0.166 | 92.6 |
| 60 | 2.80 | 0.120 | 0.107 | 96.2 |

Finally, the tendency for inorganic scale formation in a solution that contained specific volume of produced water and defined amount of nutrient recipe was determined by a combination of bench tests and chemical modeling of scale formation. The procedures include: thermodynamic prediction modeling using SCALECHEM™ 3.1 (OLI Systems) in order to calculate scale formation by the mixtures; analysis of solid filtrate collected by passing produced water through a 0.45 HV filter, and in which the solids were vacuum dried, weighed and subjected to FTIR and XRD/XRF in order to identify its composition; bottle tests using filtered (0.22 µm) produced water and nutrient recipe in which the major constituents in the recipe were added into the produced water followed by manual swirling of the mixture followed by incubation at stationary position for appropriate period and further analysis by inductively coupled plasma (ICP); bottle test at 80° F. by filtration of produced water with 0.45 µm and 0.22 µm filters, and, thereafter, ammonium phosphates and vitamin solution were equilibrated at 80° F. and then added into the produced water that was also equilibrated at a similar temperature to achieve the defined concentrations of nutrient components. The mixtures were then incubated overnight on a shaker (85 rpm) at 80° F. After that the mixtures were then filtered and analyzed by ICP in order to determine phosphate concentration in the solution; kinetics of generation of calcium phosphate solids at different initial calcium concentration was determined by kinetic turbidity measurement. Then 125 µL of the different concentrated stock solutions of calcium was added individually into 2.5 mL of synthetic produced water-nutrient solution placed in cuvettes. The absorbance of the mixtures was read at 500 nm with a VARIAN CARY™ UV-Vis 1000 Spectrophotometer. In all cases, samples in the cuvettes were stirred during incubation at 47 and 80° F.

Thermodynamic modeling showed that there is the likelihood for inorganic scale formation in produced water-recipe mixture, suggesting that the final composition of optimized nutrient recipe is determined after careful consideration of the composition of the scale forming compounds that precipitates in the mixture. This method predicted the most likely inorganic mineral scale based on the saturation index (SI) of the identified compounds. Calcium-containing compounds were identified as most likely inorganic mineral scale. In agreement with the result of thermodynamic prediction, addition of nutrients into the produced water led to depletion of calcium in the produced water-nutrient recipe mixture as determined by ICP. Results also shows precipitation of some calcium-containing compounds may cause depletion of other essential nutrients in the produced water-nutrient recipe mixture.

Example 7

Reservoir Simulation of Biogas

Figure 16:
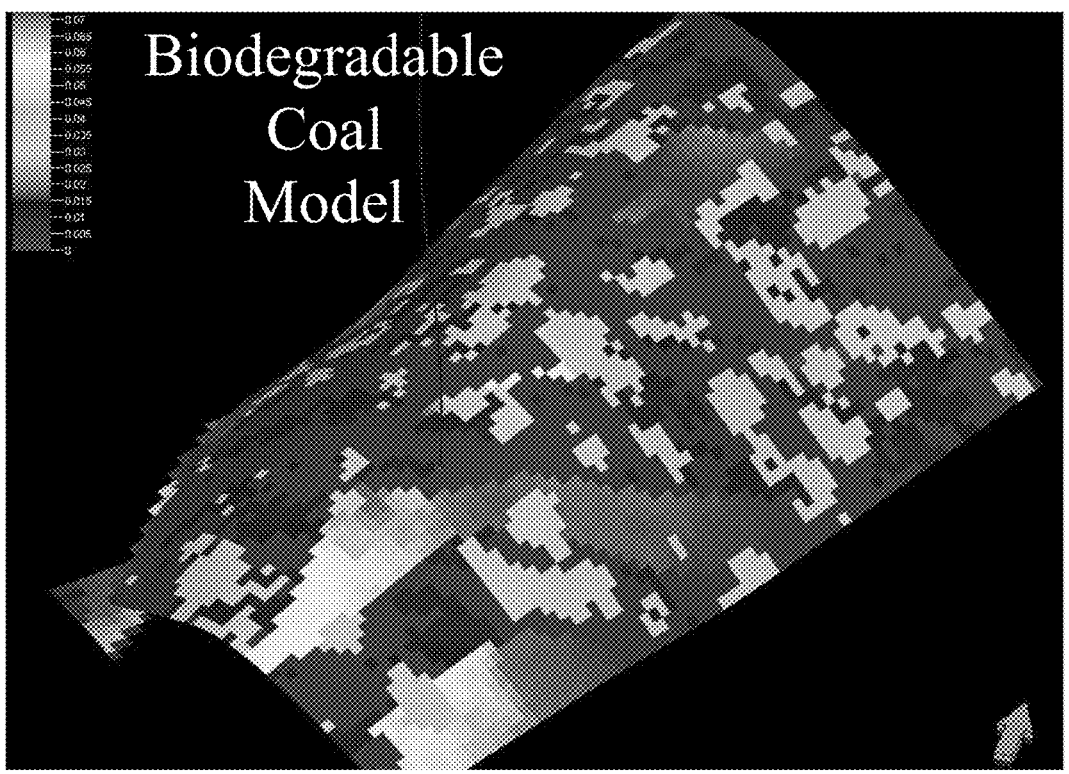
FIG. 16: A schematic illustration representation of a three-dimensional geocellular model showing the biodegradable coal fraction in one layer. Lighter color indicates a higher percentage of biodegradable coal. Arrow in picture points North. This model was used to simulate the volume and flow of biogenic gas generated from the addition of optimized nutrients and microbial additions.

Simulation of biogas in the sub-surface reservoir requires the ability to model the flow of nutrient & microbe amended fluids and methane through porous media, as well as the ability to represent microbial generation of methane through chemical reactions. To accomplish these tasks, computational modeling software was used, incorporating methane generation rates as derived from laboratory testing and a geocellular model which adequately represents the geologic variability inherent in the reservoir. The generation of methane from microbial processes is represented through a series of chemical reactions involving the following components: microbes, nutrients, and biodegradable coal volume in the sub-surface. Sub-surface microbe and nutrient volumes are determined from current conditions in the sub-surface, as analyzed from produced water samples, and assumed volumes of nutrient/microbe amendments to be injected into the sub-surface. Biodegradable coal volume in the sub-surface reservoir may be calculated from petrophysical interpretation of coals observed in well logs and total organic carbon (TOC) measurements of sub-surface core samples for each lithology/and/or facies expected to be contacted by injected fluids. Coal volume is then discounted based on the both the fraction of the coal that is biodegradable and on the accessibility of these biodegradable coals to microbes in the sub-surface, e.g., lithologies or facies with lower porosity or permeability will be difficult for microbes to move through, and, therefore, access the available organic matter, as compared to lithologies and/or facies with higher porosity/permeability (Table 6). The fraction of accessible biodegradable coal can then be populated throughout the geocellular model based on the lithology/facies distribution previously defined for that model (FIG. 16).

TABLE 6

Coal volumes

| Model Facies | Log-based coal, Vol. fraction | *Coal content (TOC-based) in disseminated form, Vol. fraction | Coal beds + disseminated coal, Vol. fraction | Permeability | Accessible coal fraction (based on perm.) | Bio-degradable coal fraction | Bio-degradable & accessible coal fraction | Bio-degradable coal Vol. % of rock |
|---|---|---|---|---|---|---|---|---|
| Flood plain | 0.260 | 0.046 | 0.306 | intermediate to very low | 0.50 | 0.250 | 0.125 | 3.829 |
| Abandoned channel | 0.100 | 0.046 | 0.146 | intermediate to low | 0.70 | 0.225 | 0.158 | 2.305 |
| Crevasse splay | 0.100 | 0.113 | 0.213 | intermediate | 0.75 | 0.225 | 0.169 | 3.600 |
| Channel belt | 0.060 | 0.005 | 0.065 | good | 0.90 | 0.200 | 0.180 | 1.176 |

*for abandoned channel fraction, floodplain was used because the 2 coaly shale samples/intervals are likely included in the log-derived coals (these have very high TOC)

Figure 17:
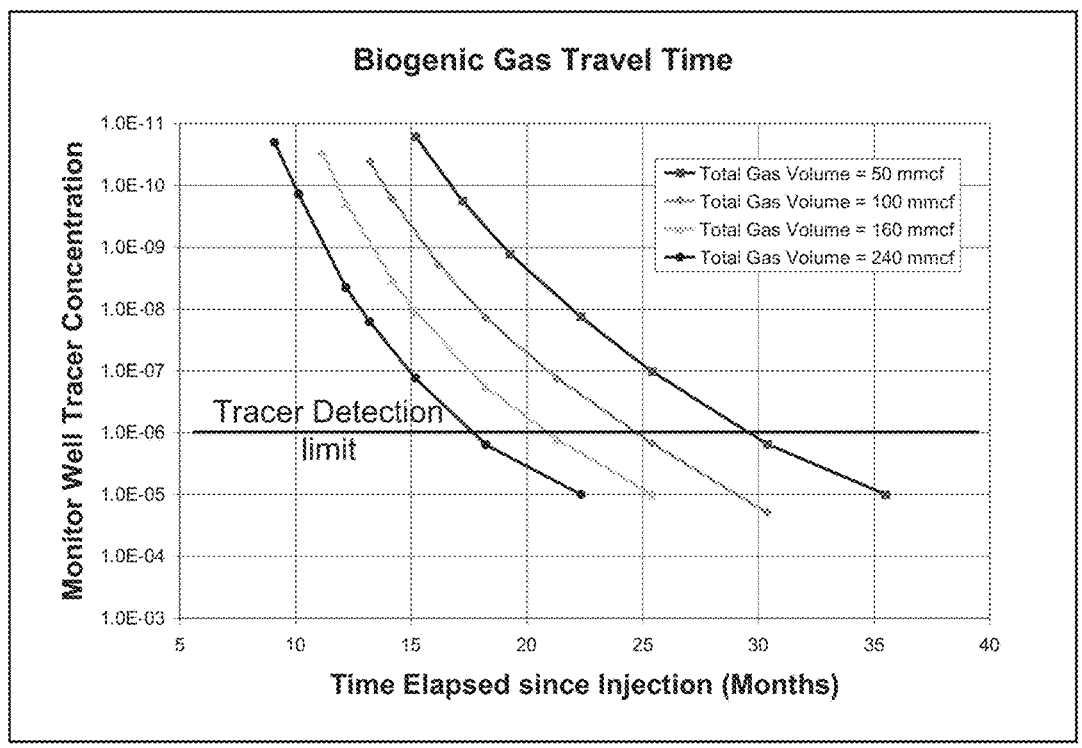
FIG. 17: graphically illustrates the results from simulation of multiple biogas generation rates/volumes using compositions and methods of the invention, showing tracer concentration observed at the monitoring well over time, starting at 5 months after start of gas injection. Travel time between injection well and monitor well is reduced with higher biogas generation rates/volumes.

The sub-surface simulation of biogas as described above is highly dependent on understanding how applicable the methane generation rates from laboratory testing are to the sub-surface. Given the large degree of uncertainty in this understanding, it is desirable to test multiple methane generation rates in order to understand the range of possible methane volumes generated and the travel time of methane generated near the injection well-bores to the producing and/or monitoring well-bores. In order to quickly test multiple scenarios, a simplified simulation approach can be used to mimic the simulation described above, while significantly decreasing the computer processing time required for simulation. For this simulation, a range of potential biogas generation rates in the sub-surface are calculated by upscaling the biogas generation rates observed in laboratory experiments to the estimated rock and fluid volumes expected in the sub-surface. These multiple rates may be further modified up or down by scaling factors to represent possible unknown conditions in the sub-surface and give a wider variation in potential outcomes. These various rates are then represented as gas injection rates into the injection well-bore. Simulation of methane flow from injection well-bore to producing/monitoring well-bores can then be done using standard flow simulation software. Adding a small volume of a gas isotope tracer (described below) to the gas injection then allows the gas travel time from injection well-bore to producing/monitoring wellbore to be quickly estimated for multiple biogas generation rates. The simulation results shown in FIG. 17 are based on an 18-month injection of gas at various rates, representing the total volume of biogas expected to be generated during the 18-month period. Once the tracer detection limit is established, the gas travel time from injection wellbore to producing/monitoring wellbore can be determined for the various biogas generation rates. This method can also be used to quickly test various reservoir properties with uncertainties that may also affect the gas movement through the reservoir. This will assist in identifying reservoir properties which may need further investigation to narrow key uncertainties and in determining the appropriate length of time necessary for monitoring to detect newly generated biogas.

Example 8

Mimicking of Coal Monomer

Modeling microbial growth in a reservoir is difficult because the subterranean carbon sources often have differing chemical compositions, limited surface area, microbial growth is restricted, and reaction conditions including pressures and temperatures are hard to replicate in vitro. In order to quickly identify growth factors that improve microbial growth in situ, a method of growing microbial cultures in vitro was required that both mimicked the subterranean formation and increased surface area to allow for faster reaction times. Monomers were identified for various subterranean carbonaceous formations that mimicked the chemical-bond structures present within the targeted formation substrate. In addition to water environment, microbial associations are likely to be partially controlled by the substrate chemistry.

Chemical compositions that mimic substrate chemistry are readily available and may be identified based on the structure and composition of the carbon compounds in the reservoir. In some examples the substrates are selected from syringic acid; syringic acid methyl ester; dimethyl phenol; 2,4-dimethyl phenol; guaiacol; protocatechuic acid; vanillic acid; isovanillic acid; caffeic acid; ferulic acid; isoferulic acid; dibenzofuran; 8-amino 2-naphthanol; 7-methoxy coumarin; biphenyl 4-methanol; 1,1'-biphenyl methyl; methoxy biphenyl; 3-methoxy biphenyl; dimethyl phenanthrene; dimethyl fluoranthene; 8,9-dimethyl fluoranthene; dimethyl-napththalene; dimethyl anthracene; acetylene; diacetylene; vinylacetylene; methyl naphthalene; trimethyl naphthalene; 7-ethyl-1,4-dimethylazulene; trimer-3-methoxy-4-benzyloxy-alpha-(2-methoxyphenoxy)-b-hydroxypropiophenone; composition derived from the basic structure of lignin or kerogen; or other hydrocarbons found in the subterranean carbonaceous formation. Addition of these substrates to an aqueous culture, sand-pack bioreactor, or as an additive to other growth media provides a method to identify microorganisms that will preferentially degrade a carbonaceous substrate, and/or generate biogas from the carbonaceous substrate.

TABLE 7

Carbonaceous formation properties

| Sample | Location(s) | Rank | Vitrinite Reflectance (% $R_o$) | Monomers |
|---|---|---|---|---|
| Coal A | Alaska | Lignite/sub-bituminous C | 0.33 | quinic acid, shikimic acid, pannic acid, ferulic acid |
| Coal B | Utah | High-volatile bituminous C | 0.56 | |
| Coal C | New Mexico | High-volatile bituminous A | 0.87 | syringic acid; dimethyl phenol; 8-amino 2-naphthanol; 7-methoxy coumarin; biphenyl 4-methanol; methoxy biphenyl; 1,1'-biphenyl methyl; dimethyl phenanthrene; dimethyl fluoranthene; and trimer-3-methoxy-4-benzyloxy-alpha-(2-methoxyphenoxy)-B-hydroxypropiophenone |
| Coal D | New Mexico | Medium-volatile bituminous | 1.10 | syringic acid; dimethyl phenol; 8-amino 2-naphthanol; 7-methoxy coumarin; biphenyl 4-methanol; methoxy biphenyl; 1,1'-biphenyl methyl; dimethyl phenanthrene; dimethyl fluoranthene; and trimer-3-methoxy-4-benzyloxy-alpha-(2-methoxyphenoxy)-B-hydroxypropiophenone |
| Peat | Europe, North America, New Zealand, Asia, Malaysia | Peat | <0.3 | humic, fibric, hemic, sapric syringic, quinic, shikimic, pannic, and/or ferulic acids, as well as compositions listed below |

TABLE 7

Carbonaceous formation properties

| Sample | Location(s) | Rank | Vitrinite Reflectance (% $R_o$) | Monomers |
|---|---|---|---|---|
| Coal | Europe, North America, Asia, Australia, India | Lignite | ~0.25-0.38 | Lignin carbonyl, carboxyl, amidic, ester, phenolic, alcoholic, ketone, aldehyde, benzenoid, paraffinic, naphthenic and aromatic hydrocarbon monomers |
| Coal | Wyoming | Sub-bitumous | ~0.38-0.6 | |
| Coal | Brazil, Illinois, Indiana | High-volatile bituminous | ~0.5-1.1 | |
| Coal | | Medium-volatile bituminous | ~1.1-1.5 | |
| Coal | | Low-volatile bituminous | ~1.5-1.9 | |
| Coal | | Semi-anthracite | ~1.9-2.75 | |
| Coal | | Anthracite | ~2.75-6.0 | |

The discussion of any reference is not an admission that it is prior art to the present invention, especially any reference that may have a publication date after the priority date of this application. At the same time, each and every claim below is hereby incorporated into this detailed description or specification as additional embodiments of the present invention.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

REFERENCES

All references, publications, patents, patent applications cited herein are hereby expressly incorporated by reference for all purposes. The discussion of any reference is not an admission that it is prior art to the present invention, especially any reference that may have a publication data after the priority date of this application. Incorporated references are listed again here for convenience:

1. U.S. Pat. Nos. 4,826,769, 4,845,034, 6,143,534, Menger et al., "Microbial process for producing methane from coal." Reliant Energy Inc. (1985).
2. U.S. Pat. No. 5,845,032, Srivastava and Walia, "Biological production of humic acid and clean 25 fuels from coal." (1998).
3. U.S. Pat. No. 5,424,195, Volkwein, "Method for in situ biological conversion of coal to methane." US Dept. Interior, (1990).
4. U.S. Pat. Nos. 5,670,345, 5,854,032, Srivastava and Walia, "Biological production of humic acid and clean fuels from coal" Arctech Inc., (1995).
5. U.S. Pat. No. 6,543,535, US2001045279, WO0168904, Converse et al., "Process for stimulating microbial activity in a hydrocarbon-bearing, subterranean formation." ExxonMobil Upstream Res. Co. (2000).
6. U.S. Pat. No. 6,613,520, US2002065609, US2004110183, WO0177392, Ashby "Methods for the survey and genetic analysis of populations." (2003).
7. U.S. Pat. Nos. 7,426,960, 7,640,978, 7,845,403, US2006254765, US2008299635, US2008289816, US2010101782, US2010300680, WO2006118570, WO2007089713, Pfeiffer et al., "Biogenic fuel gas generation in geologic hydrocarbon deposits." (2005)
8. U.S. Pat. No. 7,696,132, US2007261843, US2007295505, US2010190203, US2010248322, WO2007118094, WO2008157547, Pfeiffer, et al., "Chemical amendments for the stimulation of biogenic gas generation in deposits of carbonaceous matter." Luca Tech. LLC (2006).
9. U.S. Pat. No. 7,832,475, US2009246849, US2011027849, WO2007022122, Jin, et al., "Formation Pretreatment with Biogenic Methane Production Enhancement Systems." Univ. Wyoming Res. Corp. (2005).
10. US2004033557, WO0234931, Scott and Guyer, "Method of generating and recovering gas from subsurface formations of coal, carbonaceous shale and organic-rich shale." (2000).
11. US20070251146, WO2005115649, Larter, et al., "Process for Stimulating Production of Methane From Petroleum in Subterranean Formations." (2004).
12. US20100047793, WO2009140313, Toledo, et al. "Methods To Stimulate Biogenic Methane Production From Hydrocarbon-Bearing Formation." Synthetic Genomics Inc. (2004).
13. WO2010012093, Gates, et al. "Methods And Systems For Gas Production From A Reservoir." Profero Energy Inc. (2008).
14. Altschul, et al., "Gapped BLAST and PSI-BLAST: a new generation of protein database search programs." Nucleic Acids Res 25:3389-402 (1997).
15. Ashby, et al., "Serial analysis of rRNA genes and the unexpected dominance of rare members of microbial communities." Appl Environ Microbiol 73:4532-42 (2007).
16. Brooks, et al., "Controls on methane production in a tidal freshwater estuary and a peatland: methane production via acetate fermentation and $CO_2$ reduction." Biogeochemistry 62:19-37 (2003).
17. Budwill, "Microbial Methanogenesis and its Role in Enhancing Coalbed Methane Recovery." Canadian Society of Exploration Geophysicists Recorder, October 2003, 41-46 (2003).
18. Connon and Giovannoni, "High-Throughput Methods for Culturing Microorganisms in Very-Low-Nutrient Media Yield Diverse New Marine Isolates." Appl. Environ. Microbiol. 68(8): 3878-85 (2002).
19. Doerfert, et al., "*Methanolobus* zinderi sp. nov., a methylotrophic methanogen isolated from a deep subsurface coal seam." Int J Syst Evol Microbiol 59:1064-9 (2009).
20. Dolfing, et al., "Thermodynamic constraints on methanogenic crude oil biodegradation." ISME J 2:442-52 (2008).
21. Faiz and Hendry, "Microbial activity in Australian CBM reservoirs." Search and Discovery Article #80033 (2009)
22. Green, et al., "Characterization of a methanogenic consortium enriched from a coalbed well in the Powder River Basin." U.S.A. Int'l J. Coal Geology 76:34-45 (2008).
23. Margulies, et al., "Genome sequencing in microfabricated high-density picoliter reactors." Nature 437:376-80 (2005).
24. McInerney, et al., "Syntrophy in anaerobic global carbon cycles." Current opinion in biotechnology 20: 623-32 (2009).
25. Mochimaru, et al., "Methanogen Diversity in Deep Subsurface Gas-Associated Water at the Minami-Kanto Gas Field in Japan." Geomicrobiology Journal 24(2): 93-100 (2007).
26. Pace, "A molecular view of microbial diversity and the biosphere." Science 276: 734-40 (1997).
27. Roh, et al., "Metal reduction and iron biomineralization by a psychrotolerant Fe(III)-reducing bacterium, *Shewanella* sp. strain PV-4." Appl. Environ. Microbiol. 72:3236-44 (2006).
28. Sait, et al., "Cultivation of globally distributed soil bacteria from phylogenetic lineages previously only detected in cultivation-independent surveys." Environ Microbiol 4:654-66 (2002).
29. Schink, "Energetics of syntrophic cooperation in methanogenic degradation." Microbiol Mol Biol Rev 61:262-80 (1997).
30. Shelton and Tiedje "General method for determining anaerobic biodegradation potential." Appl Environ Microbiol 47: 850-7 (1984).
31. Strąpoć, et al. "Methane-Producing Microbial Community in a Coal Bed of the Illinois Basin." Appl. Environ. Microbiol. 74: 2424-32 (2008).
32. Venter, et al., "Environmental genome shotgun sequencing of the Sargasso Sea." Science 304: 66-74 (2004).
33. Whiticar, et al., "Biogenic methane formation in marine and freshwater environments: CO2 reduction vs. acetate fermentation—Isotope evidence." Geochimica et Cosmochimica Acta 50:693-709 (1986).
34. Zinder, Methanogens. In: Techniques in Microbial Ecology, Burlage, et al., Eds. J. Oxford University Press. pp. 113-36 (1998).

A number of embodiments of the invention have been described. Nevertheless, it will be understood that various modifications may be made without departing from the spirit and scope of the invention. Accordingly, other embodiments are within the scope of the following claims.

What is claimed is:

1. A method of enhancing a biochemical process, the method comprising:
   preparing a synthetic consortium by:
   (i) obtaining two or more samples from at least two different sources of biogenic material, wherein each sample comprises a plurality of microbes;
   (ii) determining a microbial composition of each sample, wherein an abundance of each observed microbe is recorded for each sample;
   (iii) performing a correlation analysis of the abundances among microbes in the samples;
   (iv) identifying at least two microbes from among the plurality of microbes, wherein the abundance correlation between the at least two microbes is greater than to other microbes in the samples; and
   (v) combining purified isolates of the at least two microbes to form the synthetic consortium;
   adding the synthetic consortium to a substrate comprising plant matter, wherein the abundances of the at least two microbes in the synthetic consortium are different than natural abundances of the at least two microbes in the substrate;
   wherein the at least two microbes participate in a common metabolic pathway of the biochemical process; and
   wherein the synthetic consortium increases a rate of the biochemical process of the plant matter relative to a rate of the biochemical process in absence of the synthetic consortium.

2. The method of claim 1, wherein the at least two microbes of the synthetic consortium are not native to the plant matter.

3. The method of claim 1, wherein adding the synthetic consortium to the plant matter supplements a native population of microbes with the at least two microbes of the synthetic consortium.

4. The method of claim 3, further comprising introducing a nutrient mix to the native population with the synthetic consortium, wherein the nutrient mix is added in a single bolus, a continuous process, or a pulsed process.

5. The method of claim 4, wherein the nutrient mix is designed to decrease an amount of native microbes that negatively affect the biochemical process.

6. The method of claim 4, wherein the nutrient mix comprises phosphorus, sulfur, nitrogen, potassium, sodium, chlorine, or a combination thereof.

7. The method of claim 1, wherein the synthetic consortium is a microbial additive to a growth medium.

8. The method of claim 1, wherein the synthetic consortium further comprises at least one additional microbe, and wherein a natural abundance of the at least one additional microbe in the substrate is not correlated with the natural abundances of the at least two microbes.

9. The method of claim 1, wherein the synthetic consortium comprises at least six different microbe strains obtained from purified cultures.

10. The method of claim 1, wherein the at least two microbes are bacteria or archaea.

11. The method of claim 1, wherein the biochemical process transforms the plant matter through a biochemical reaction.

12. The method of claim 1, wherein the plant matter is nutrient deficient.

13. The method of claim 1, wherein the synthetic consortium is selected for growth and metabolic performance under selected environmental conditions.

14. The method of claim 1, wherein the at least two microbes are selected to perform complementary steps of the metabolic pathway.

15. The method of claim 1, further comprising characterizing the plant matter.

16. The method of claim 1, wherein the at least two microbes comprises a first microbe and a second microbe, and an amount of the first microbe relative to an amount of the second microbe in the synthetic consortium is different than the natural abundance of the first microbe relative to the natural abundance of the second microbe in the substrate.

17. The method of claim 1, wherein performing the correlation analysis comprises determining a correlation of the abundances of the microbes of the plurality of microbes with an environmental parameter, wherein the environmental parameter comprises pH, salinity, or temperature.

18. The method of claim 1, wherein determining a microbial composition of each sample comprises genetic sequencing.

19. The method of claim 1, wherein determining the microbial composition of each sample comprises determining DNA sequences of at least a portion of 16S rRNA genes present in each sample and comparing the DNA sequences to a database.

20. The method of claim 1, wherein determining the microbial composition of each sample comprises determining a cell count of each microbe of the plurality of microbes.

21. The method of claim 1, wherein identifying the at least two microbes is an integrated process.

22. The method of claim 1, wherein performing the correlation analysis comprises use of hierarchical clustering algorithms.

23. A method of enhancing a biochemical process, the method comprising:
preparing a synthetic consortium by:
(i) obtaining two or more samples from at least two different sources of biogenic material, wherein each sample comprises a plurality of microbes;
(ii) determining a microbial composition of each sample, wherein an abundance of each observed microbe is recorded for each sample;
(iii) performing a correlation analysis of the abundances of microbes in the samples;
(iv) identifying at least two microbes from among the plurality of microbes, wherein the abundance correlation between the at least two microbes is greater than to other microbes in the samples; and
(v) combining purified isolates of the at least two microbes to form the synthetic consortium;
wherein abundances of the identified microbes in the synthetic consortium are different than the abundances recorded for each sample; and
wherein the at least two microbes participate in a common metabolic pathway of the biochemical process, such that, when added to a native microbial community of a substrate, the synthetic consortium increases a rate of the biochemical process of the substrate relative to a rate of the biochemical process in absence of the synthetic consortium.

24. The method of claim 23 wherein the substrate comprises one or more of organic matter, plant matter, or minerals.

25. The method of claim 23, wherein the at least two microbes of the synthetic consortium are not members of the native microbial community.

26. A method of enhancing a biochemical process, the method comprising:
adding a composition comprising a synthetic consortium to a nutrient-deficient substrate comprising plant matter to supplement a native population of microbes, wherein the synthetic consortium comprises at least two microbes, and abundances of the at least two microbes in the synthetic consortium are different than natural abundances of the at least two microbes in the nutrient-deficient substrate, the synthetic consortium being prepared by:
(i) obtaining two or more samples from sources of biogenic material, each sample comprising a plurality of microbes;
(ii) determining a microbial composition of each sample by genetic sequencing, wherein an abundance of each observed microbe is recorded for each sample;
(iii) performing a correlation analysis of the abundances among microbes in the samples according to an algorithm;
(iv) identifying the at least two microbes from among the plurality of microbes, wherein the abundance correlation between the at least two microbes is greater than to other microbes in the samples, and the at least two microbes are correlated with an environmental parameter associated with the two or more samples; and
(v) combining cultures of the at least two microbes to form the synthetic consortium;
wherein the at least two microbes participate in a common metabolic pathway of the biochemical process and are selected to perform complementary steps of the metabolic pathway;

wherein the synthetic consortium increases a rate of the biochemical process of the plant matter relative to a rate of the biochemical process in absence of the synthetic consortium; and wherein the synthetic consortium is a microbial additive selected for growth and metabolic performance under selected environmental conditions.

* * * * *